(12) United States Patent
Aebi et al.

(10) Patent No.: US 7,935,707 B2
(45) Date of Patent: May 3, 2011

(54) IMIDAZOLE DERIVATIVES

(75) Inventors: Johannes Aebi, Binningen (CH); Alfred Binggeli, Binningen (CH); Luke Green, Basel (CH); Guido Hartmann, Loerrach (DE); Hans P. Maerki, Basel (CH); Patrizio Mattei, Riehen (CH); Fabienne Ricklin, Hombourg (FR); Olivier Roche, Folgensbourg (FR)

(73) Assignee: Hoffman-La Roche Inc., Nutley, NJ (US)

( * ) Notice: Subject to any disclaimer, the term of this patent is extended or adjusted under 35 U.S.C. 154(b) by 136 days.

(21) Appl. No.: 12/215,104

(22) Filed: Jun. 25, 2008

(65) Prior Publication Data
US 2009/0012063 A1    Jan. 8, 2009

(30) Foreign Application Priority Data
Jul. 2, 2007 (EP) .................. 07111552

(51) Int. Cl.
A61K 31/4025 (2006.01)
A61K 31/4178 (2006.01)
A61K 31/497 (2006.01)
A61K 31/4468 (2006.01)
C07D 239/42 (2006.01)
C07D 401/14 (2006.01)
C07D 211/58 (2006.01)

(52) U.S. Cl. ........ 514/256; 514/275; 514/318; 514/326; 544/329; 544/333; 546/194; 546/208

(58) Field of Classification Search ............... 548/311.1; 514/252.13, 256, 317, 396; 546/193, 208; 544/242, 336, 359
See application file for complete search history.

(56) References Cited

U.S. PATENT DOCUMENTS

| | | | |
|---|---|---|---|
| 6,369,236 B1 | 4/2002 | Kleemann et al. | |
| 7,361,500 B2 | 4/2008 | Stett et al. | |
| 2003/0153067 A1 | 8/2003 | Steet et al. | |
| 2008/0153146 A1 | 6/2008 | Stett et al. | |

FOREIGN PATENT DOCUMENTS

| | | |
|---|---|---|
| DE | 198 32 428 | 1/2000 |
| JP | 54 41881 | 4/1979 |
| WO | WO 02/03058 | 1/2002 |
| WO | WO 03/037332 | 5/2003 |
| WO | WO 2004/052850 | 6/2004 |
| WO | WO 2005/080378 | 9/2005 |
| WO | WO 2006/014413 | 2/2006 |
| WO | WO 2006/089076 | 8/2006 |
| WO | WO 2006/089076 A2 * | 8/2006 |

OTHER PUBLICATIONS

Van Lommen G et al, *Bioorgnic & Med. Chem. Letters*, 15:3 (2005) 497-500 XP004739642.
Ohkubo M et al, *Chem.. and Pharma. Bull, Pharma Soc. of Japan*, 43:6 (1995) 947-954 XP002153139.

* cited by examiner

*Primary Examiner* — Yong Chu
*Assistant Examiner* — Alicia L Otton
(74) *Attorney, Agent, or Firm* — George W. Johnston; Patricia S. Rocha-Tramaloni

(57) ABSTRACT

The invention is concerned with novel imidazole derivatives of formula (I),

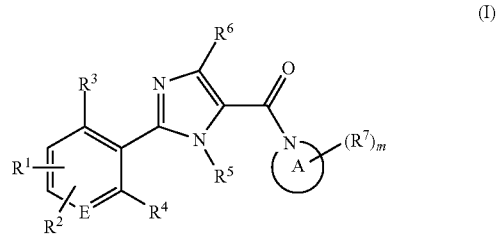

wherein

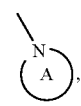

m, E, $R^1$, $R^2$, $R^3$, $R^4$, $R^5$, $R^6$ and $R^7$ are as defined in the description and in the claims, as well as physiologically acceptable salts thereof. These compounds are antagonists of CCR-2 receptor, CCR-5 receptor and/or CCR-3 receptor and can be used as medicaments.

14 Claims, No Drawings

IMIDAZOLE DERIVATIVES

PRIORITY TO RELATED APPLICATION(S)

This application claims the benefit of European Patent Application No. 07111552.1, filed Jul. 2, 2007, which is hereby incorporated by reference in its entirety.

SUMMARY OF THE INVENTION

There are provided compounds of the formula

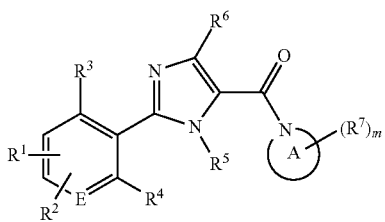

wherein

E, $R^1$, $R^2$, $R^3$, $R^4$, $R^5$, $R^6$, $R^7$ and m are as herein described.

BACKGROUND OF THE INVENTION

The compounds of formula (I) are CCR2 receptor (Chemokine Receptor 2/Monocyte chemotactic protein 1 receptor) antagonists and also CCR-5 receptor (Chemokine Receptor 5) and/or CCR-3 receptor (Chemokine Receptor 3) antagonists. Chemokines are a family of small, secreted proinflammatory cytokines functioning as chemoattractants for leukocytes. They promote trafficking of leukocytes from vascular beds into surrounding tissues in response to inflammatory signals. Chemotaxis starts upon chemokine binding to receptors (GPCRs) by initiating signalling pathways involving increased Ca-flux, inhibition of cAMP production, rearrangements of the cytoskeleton, activation of integrins and of cell motility processes and an increase in the expression of adhesion proteins.

Proinflammatory chemokines are considered to be involved in the development of atherosclerosis and other important diseases with inflammatory components like rheumatoid arthritis, asthma, multiple sclerosis, transplant rejection and ischemia reperfusion injury with specific prominent effects in nephropathy and peripheral vascular diseases. Monocyte Chemotactic protein 1 is considered to be the major stimulated chemokine mediating inflammatory processes in these diseases through the CCR2 receptor on monocytes and on some T lymphocytes. In addition MCP-1/CCR2 are in discussion to be related to the progression of the metabolic syndrome to more severe stages of obese and diabetic diseases.

CCR2 has also been linked to HIV infection, and consequently the course of autoimmune diseases, through its heterodimerization with CCR5 which has a role as coreceptor for viral entry into host cells.

Thus, CCR2 can be a target of a new medicine for treatment of peripheral vascular diseases, and more specifically for treatment of patients with critical limb ischemia. Furthermore, study results and experiences from the development of a new CCR2 medicine for this indication may facilitate a follow-up development for treatment of atherosclerosis. There is a large body of information from animal models of MCP-1 and CCR2 ko mice in wt or apoE−/− or LDL-R−/− backgrounds showing that the MCP-1/CCR2 pathway is essential for monocyte/macrophage recruitment, and also for intimal hyperplasia and the formation and stability of atherosclerotic lesions. In addition, numerous reports describe involvement of the MCP-1/CCR2 pathway in man post injury and in various inflammatory processes, including such in vascular beds.

The present invention provides the novel compounds of formula (I) which are CCR2 receptor antagonists, with some antagonist activity also at CCR-3 and CCR-5.

DETAILED DESCRIPTION OF THE INVENTION

The invention is concerned with novel imidazole derivatives of formula (I),

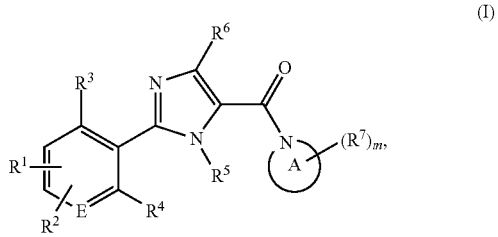

wherein

is a heterocyclyl, which is a non-aromatic mono-cyclic radical of four to eight ring atoms, in which one or two ring atoms are nitrogen atoms, the remaining ring atoms being carbon atoms;

E is N or CH, provided that $R^1$ or $R^2$ can attach to C, by replacing H;

$R^1$ and $R^2$ are independently hydrogen, halogen, $C_{1-6}$ alkoxy, $C_{1-6}$ alkyl, halo $C_{1-6}$ alkyl, halo $C_{1-6}$ alkoxy or optionally substituted heterocyclyl; provided that one of $R^1$ and $R^2$ is not hydrogen;

$R^3$ and $R^4$ are independently hydrogen, $C_{1-6}$ alkoxy, halo $C_{1-6}$ alkyl, halo $C_{1-6}$ alkoxy or halogen;

$R^5$ is $C_{1-6}$ alkyl, halo $C_{1-6}$ alkyl, $C_{3-7}$ cycloalkyl or $C_{3-7}$ cycloalkyl $C_{1-6}$ alkyl;

$R^6$ is hydrogen, $C_{1-6}$ alkyl, halo $C_{1-6}$ alkyl, trimethylsilanyl $C_{1-6}$ alkyl, heteroalkyl, $C_{2-6}$ alkenyl, $C_{2-6}$ alkynyl, hydroxy $C_{2-6}$ alkenyl, hydroxy $C_{2-6}$ alkynyl, $C_{1-6}$ alkoxy $C_{2-6}$ alkenyl, $C_{1-6}$ alkoxy $C_{2-6}$ alkynyl, trimethylsilanyl $C_{2-6}$ alkenyl, trimethylsilanyl $C_{2-6}$ alkynyl, $C_{1-6}$ alkoxy, halo $C_{1-6}$ alkoxy, heteroalkoxy, optionally substituted $C_{3-7}$ cycloalkyl, optionally substituted $C_{3-7}$ cycloalkyl $C_{1-6}$ alkyl, halogen, cyano, optionally substituted phenyl, optionally substituted heteroaryl, optionally substituted heterocyclyl or optionally substituted phenyl-methoxy-$C_{1-6}$ alkyl;

m is 0, 1, 2, 3 or 4;

$R^7$ is,
  a) when attached to a ring carbon atom, independently hydrogen, $C_{1-6}$ alkyl, halo $C_{1-6}$ alkyl, heteroalkyl, $C_{2-6}$ alkenyl, $C_{2-6}$ alkynyl, hydroxy $C_{2-6}$ alkenyl, hydroxy $C_{2-6}$ alkynyl, $C_{1-6}$ alkoxy $C_{2-6}$ alkenyl, $C_{1-6}$ alkoxy $C_{2-6}$ alkynyl, hydroxy, $C_{1-6}$ alkoxy, halo $C_{1-6}$ alkoxy, heteroalkoxy, halogen, cyano, optionally substituted phenyl, optionally substituted $C_{3-7}$ cycloalkyl, optionally substituted $C_{3-7}$ cycloalkyl $C_{1-6}$ alkyl, optionally substituted heteroaryl, optionally substituted heterocyclyl, optionally substituted phenyl-$C_{1-6}$ alkyl, optionally substituted heteroaryl-$C_{1-6}$ alkyl, optionally substituted heterocyclyl-$C_{1-6}$ alkyl, nitro, carboxy, formyl, acyl, $C_{1-6}$ alkoxycarbonyl, carbamoyl, mono- or di-$C_{1-6}$ alkyl substituted aminocarbonyl, $C_{1-6}$ alkylthio, $C_{1-6}$ alkylsulfinyl or $C_{1-6}$ alkylsulfonyl or amino optionally substituted by one or two substituents independently selected from the group consisting of $C_{1-6}$ alkyl, heteroalkyl, optionally substituted $C_{3-7}$ cycloalkyl and optionally substituted heterocyclyl; or when attached to a ring nitrogen atom, independently hydrogen, $C_{1-6}$ alkyl, halo $C_{1-6}$ alkyl, heteroalkyl, $C_{2-6}$ alkenyl, $C_{2-6}$ alkynyl, hydroxy $C_{2-6}$ alkenyl, hydroxy $C_{2-6}$ alkynyl, $C_{1-6}$ alkoxy $C_{2-6}$ alkenyl, $C_{1-6}$ alkoxy $C_{2-6}$ alkynyl, optionally substituted $C_{3-7}$ cycloalkyl or optionally substituted $C_{3-7}$ cycloalkyl $C_{1-6}$ alkyl, optionally substituted heterocyclyl or optionally substituted heterocyclyl $C_{1-6}$ alkyl;

provided that

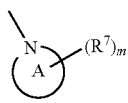

contains at least one nitrogen atom, which is not directly bonded to a carbonyl group or a heteroatom; and

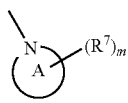

does not contain a nitrogen atom, which is directly bonded to a heteroatom; or a prodrug or a pharmaceutically acceptable salt thereof.

Preferably E is CH, provided that $R^1$ or $R^2$ can attach to C, by replacing H, and $R^1$ and $R^2$ are independently hydrogen, halogen, $C_{1-6}$ alkoxy, $C_{1-6}$ alkyl, halo $C_{1-6}$ alkyl or halo $C_{1-6}$ alkoxy.

Further, the invention is concerned with a process for the manufacture of the above compounds, pharmaceutical preparations which contain such compounds, the use of these compounds for the production of pharmaceutical preparations.

Unless otherwise indicated, the following definitions are set forth to illustrate and define the meaning and scope of the various terms used to describe the invention herein.

The term "heteroatom" means a nitrogen atom, an oxygen atom or a sulphur atom.

The term "halogen" or "halo" means fluorine, chlorine, bromine and iodine, with chlorine and fluorine being preferred in halo-alkyl groups and bromine and iodine being preferred for halo-aryl moieties.

The term "$C_{1-6}$ alkyl", alone or in combination with other groups, means a branched or straight-chain monovalent alkyl radical, having one to six carbon atoms. This term is further exemplified by such radicals as methyl, ethyl, n-propyl, isopropyl, n-butyl, s-butyl, t-butyl, $C_{1-4}$ alkyl or $C_{1-3}$ alkyl is more preferred.

The term "hydroxy $C_{1-6}$ alkyl" means $C_{1-6}$ alkyl substituted by one or more, preferably one hydroxy group(s).

The term "halo $C_{1-6}$ alkyl" means $C_{1-6}$ alkyl substituted by one or more same or different halogen atoms.

The term "$C_{1-6}$ alkylene", alone or in combination with other groups, means a branched or straight-chain saturated divalent hydrocarbon radical of one to six carbon atoms, such as methylene, ethylene, tetramethylethylene.

The term "$C_{3-7}$ cycloalkyl", alone or in combination with other groups, means a saturated monovalent mono-cyclic hydrocarbon radical of three to seven ring carbons, e.g., cyclopropyl, cyclobutyl, cyclohexyl.

The term "$C_{1-6}$ alkoxy", alone or in combination with other groups, means the group R'—O—, wherein R' is a $C_{1-6}$ alkyl.

The term "halo $C_{1-6}$ alkoxy", alone or in combination with other groups, means $C_{1-6}$ alkoxy substituted by one or more, preferably one to three halogens.

The term "$C_{2-6}$ alkenyl", alone or in combination with other groups, means a straight-chain or branched hydrocarbon residue comprising a carbon-carbon double bond, having two to six carbon atoms. This term is further exemplified by such radicals as ethenyl, 2-propenyl. The term "hydroxy $C_{2-6}$ alkenyl" or "$C_{1-6}$ alkoxy $C_{2-6}$ alkenyl" means $C_{2-6}$ alkenyl substituted one or more, preferably one or two hydroxy groups or $C_{1-6}$ alkoxy groups, respectively. Most preferred are hydroxy $C_{3-6}$ alkenyl and $C_{1-6}$ alkoxy $C_{3-6}$ alkenyl groups.

The term "$C_{2-6}$-alkynyl", alone or in combination with other groups, means a straight-chain or branched hydrocarbon residue comprising a carbon-carbon triple bond, having two to six carbon atoms. This term is further exemplified by such radicals as ethynyl, 2-propynyl.

The term "hydroxy $C_{2-6}$ alkynyl" or "$C_{1-6}$ alkoxy $C_{2-6}$ alkenyl" means $C_{2-6}$ alkynyl substituted by one or more, preferably one or two hydroxy groups or $C_{1-6}$ alkoxy groups, respectively. Most preferred are hydroxy $C_{3-6}$ alkynyl and $C_{1-6}$ alkoxy $C_{3-6}$ alkynyl groups.

The term "acyl" means R—C(O)—, in which R is $C_{1-6}$ alkyl, halo $C_{1-6}$ alkyl, $C_{3-7}$ cycloalkyl or $C_{3-7}$ cycloalkyl $C_{1-6}$ alkyl.

The term "heteroalkyl" means $C_{1-6}$ alkyl substituted by one or more substituents selected independently from the group consisting of nitro, hydroxy, cyano, $C_{1-6}$ alkoxy, formyl, acyl, carboxyl, $C_{1-6}$ alkylthio, $C_{1-6}$ alkyl sulfinyl, $C_{1-6}$ alkyl sulfonyl, carbamoyl, amino and mono- or di-$C_{1-6}$ alkyl substituted amino.

The term "heteroalkoxy" means $C_{1-6}$ alkoxy substituted by one or more substituents selected independently from the group consisting of nitro, hydroxy, cyano, $C_{1-6}$ alkoxy, formyl, acyl, carboxyl, $C_{1-6}$ alkylthio, $C_{1-6}$ alkyl sulfinyl, $C_{1-6}$ alkyl sulfonyl, carbamoyl, amino and mono- or di-$C_{1-6}$ alkyl substituted amino.

The term "heterocyclyl" means non-aromatic mono-cyclic radicals of four to seven ring atoms, in which one to three ring atoms are heteroatoms independently selected from N, O and $S(O)_n$ (where n is an integer from 0 to 2), the remaining ring atoms being C.

The term "heteroaryl" means an aromatic mono-cyclic radical of 5 or 6 ring atoms, having one to three ring heteroatoms independently selected from N, O, and S, the remaining ring atoms being C.

The term "optionally substituted $C_{3-7}$ cycloalkyl" means $C_{3-7}$ cycloalkyl optionally substituted by one to three substituents independently selected from the group consisting of $C_{1-6}$ alkyl, halo $C_{1-6}$ alkyl, heteroalkyl, $C_{2-6}$ alkenyl, $C_{2-6}$ alkynyl, hydroxy $C_{2-6}$ alkenyl, hydroxy $C_{2-6}$ alkynyl, $C_{1-6}$ alkoxy $C_{2-6}$ alkenyl, $C_{1-6}$ alkoxy $C_{2-6}$ alkynyl, hydroxy, $C_{1-6}$ alkoxy, halo $C_{1-6}$ alkoxy, heteroalkoxy, $C_{3-7}$ cycloalkyl, $C_{3-7}$ cycloalkyl $C_{1-6}$ alkyl, halogen, cyano, nitro, amino, mono- or di-$C_{1-6}$ alkyl substituted amino, carboxy, formyl, acyl, $C_{1-6}$ alkoxycarbonyl, carbamoyl, mono- or di-$C_{1-6}$ alkyl substituted aminocarbonyl, $C_{1-6}$ alkylthio, $C_{1-6}$ alkylsulfinyl, $C_{1-6}$ alkylsulfonyl and —NHCO—$C_{1-6}$ alkyl.

The term "optionally substituted phenyl" means a phenyl optionally substituted by one to three substituents independently selected from the group consisting of $C_{1-6}$ alkyl, halo $C_{1-6}$ alkyl, heteroalkyl, $C_{2-6}$ alkenyl, $C_{2-6}$ alkynyl, hydroxy $C_{2-6}$ alkenyl, hydroxy $C_{2-6}$ alkynyl, $C_{1-6}$ alkoxy $C_{2-6}$ alkenyl, $C_{1-6}$ alkoxy $C_{2-6}$ alkynyl, hydroxy, $C_{1-6}$ alkoxy, halo $C_{1-6}$ alkoxy, heteroalkoxy, $C_{3-7}$ cycloalkyl, $C_{3-7}$ cycloalkyl $C_{1-6}$ alkyl, halogen, cyano, nitro, amino, mono- or di-$C_{1-6}$ alkyl substituted amino, carboxy, formyl, acyl, $C_{1-6}$ alkoxycarbonyl, carbamoyl, mono- or di-$C_{1-6}$ alkyl substituted aminocarbonyl, $C_{1-6}$ alkylthio, $C_{1-6}$ alkylsulfinyl, $C_{1-6}$ alkylsulfonyl and —NHCO—$C_{1-6}$ alkyl.

The term "optionally substituted heterocyclyl" means a heterocyclyl optionally substituted by one to three substituents independently selected from the group consisting of $C_{1-6}$ alkyl, halo $C_{1-6}$ alkyl, heteroalkyl, $C_{2-6}$ alkenyl, $C_{2-6}$ alkynyl, hydroxy $C_{2-6}$ alkenyl, hydroxy $C_{2-6}$ alkynyl, $C_{1-6}$ alkoxy $C_{2-6}$ alkenyl, $C_{1-6}$ alkoxy $C_{2-6}$ alkynyl, hydroxy, $C_{1-6}$ alkoxy, halo $C_{1-6}$ alkoxy, heteroalkoxy, $C_{3-7}$ cycloalkyl, $C_{3-7}$ cycloalkyl $C_{1-6}$ alkyl, halogen, cyano, nitro, amino, mono- or di-$C_{1-6}$ alkyl substituted amino, carboxy, formyl, acyl, $C_{1-6}$ alkoxycarbonyl, carbamoyl, mono- or di-$C_{1-6}$ alkyl substituted aminocarbonyl, $C_{1-6}$ alkylthio, $C_{1-6}$ alkylsulfinyl, $C_{1-6}$ alkylsulfonyl and —NHCO—$C_{1-6}$ alkyl.

The term "optionally substituted heteroaryl" means a heteroaryl optionally substituted by one to three substituents independently selected from the group consisting of $C_{1-6}$ alkyl, halo $C_{1-6}$ alkyl, heteroalkyl, $C_{2-6}$ alkenyl, $C_{2-6}$ alkynyl, hydroxy $C_{2-6}$ alkenyl, hydroxy $C_{2-6}$ alkynyl, $C_{1-6}$ alkoxy $C_{2-6}$ alkenyl, $C_{1-6}$ alkoxy $C_{2-6}$ alkynyl, hydroxy, $C_{1-6}$ alkoxy, halo $C_{1-6}$ alkoxy, heteroalkoxy, $C_{3-7}$ cycloalkyl, $C_{3-7}$ cycloalkyl $C_{1-6}$ alkyl, halogen, cyano, nitro, amino, mono- or di-$C_{1-6}$ alkyl substituted amino, carboxy, formyl, acyl, $C_{1-6}$ alkoxycarbonyl, carbamoyl, mono- or di-$C_{1-6}$ alkyl substituted aminocarbonyl, $C_{1-6}$ alkylthio, $C_{1-6}$ alkylsulfinyl, $C_{1-6}$ alkylsulfonyl and —NHCO—$C_{1-6}$ alkyl.

The term, "$C_{1-6}$ alkylsulfonyl", "$C_{1-6}$ alkylsulfinyl" and "$C_{1-6}$ alkylthio", alone or combination with other groups, means $C_{1-6}$ alkyl-$SO_2$—, $C_{1-6}$ alkyl-SO— and $C_{1-6}$ alkyl-S—, respectively. Preferred radicals for the chemical groups whose definitions are given above are those specifically exemplified in Examples.

Compounds of formula (I) can form pharmaceutically acceptable acid addition salts. Examples of such pharmaceutically acceptable salts are salts of compounds of formula (I) with physiologically compatible mineral acids, such as hydrochloric acid, hydrobromic acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts.

"Optional" or "optionally" means that the subsequently described event or circumstance may but need not occur, and that the description includes instances where the event or circumstance occurs and instances in which it does not. For example, "aryl group optionally substituted with an alkyl group" means that the alkyl may but need not be present, and the description includes situations where the aryl group is substituted with an alkyl group and situations where the aryl group is not substituted with the alkyl group.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

Compounds that have the same molecular formula but differ in the nature or sequence of bonding of their atoms or the arrangement of their atoms in space are termed "isomers." Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of formula (I) can possess one or more asymmetric centers. Unless indicated otherwise, the description or naming of a particular compound in the specification and claims is intended to include both individual enantiomers and mixtures, racemic or otherwise, thereof, as well as individual epimers and mixture thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

While the broadest definition of this invention is described before, certain compounds of formula (I) are preferred.

i) In the compounds of formula (I),

is preferably pyrrolidin-1-yl, piperidin-1-yl or [1,4]diazepan-1-yl, more preferably piperidin-1-yl.

ii) In the compounds of formula (I), m is preferably 1.

iii) In the compounds of formula (I), $R^7$ is preferably hydroxy $C_{1-6}$ alkyl, mono- or di-$C_{1-6}$ alkyl substituted amino or optionally substituted heterocyclyl, more preferably optionally substituted heterocyclyl, especially pyrrolidin-1-yl or 2-hydroxymethyl-pyrrolidin-1-yl.

iv) In the compounds of formula (I),

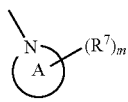

is preferably 4-pyrrolidin-1-yl-piperidin-1-yl or 4-(2-hydroxymethyl-pyrrolidin-1-yl)-piperidin-1-yl.

v) In the compounds of formula (I), $R^1$ and $R^2$ is preferably hydrogen, $C_{1-6}$ alkyl, halo $C_{1-6}$ alkyl or halo $C_{1-6}$ alkoxy and the other is $C_{1-6}$ alkyl, halo $C_{1-6}$ alkyl or halo $C_{1-6}$ alkoxy. More preferably one of $R^1$ and $R^2$ is hydrogen and the other is $C_{1-6}$ alkyl, such as n-hexyl, halo $C_{1-6}$ alkyl, such as trifluoromethyl or halo $C_{1-6}$ alkoxy, such as trifluoromethoxy.

vi) In the compounds of formula (I), $R^3$ and $R^4$ are preferably independently hydrogen or $C_{1-6}$ alkoxy, more preferably both $R^3$ and $R^4$ are hydrogen.

vii) In the compounds of formula (I), $R^5$ is preferably $C_{1-6}$ alkyl, more preferably methyl.

viii) In the compounds of formula (I), $R^6$ is preferably hydrogen, $C_{1-6}$ alkyl, trimethylsilanyl $C_{1-6}$ alkyl, heteroalkyl, $C_{2-6}$ alkenyl, $C_{2-6}$ alkynyl, hydroxy $C_{2-6}$ alkenyl, hydroxy $C_{2-6}$ alkynyl, $C_{1-6}$ alkoxy $C_{2-6}$ alkenyl, $C_{1-6}$ alkoxy $C_{2-6}$ alkynyl, trimethylsilanyl $C_{2-6}$ alkenyl, trimethylsilanyl $C_{2-6}$ alkynyl, optionally substituted $C_{3-7}$ cycloalkyl, optionally substituted $C_{3-7}$ cycloalkyl-$C_{1-6}$ alkyl, halogen, cyano, optionally substituted phenyl, optionally substituted heteroaryl, optionally substituted heterocyclyl or optionally substituted phenylmethoxy-$C_{1-6}$ alkyl, more preferably hydrogen, $C_{1-6}$ alkyl, heteroalkyl, $C_{2-6}$ alkynyl, hydroxy $C_{2-6}$ alkynyl or $C_{1-6}$ alkoxy $C_{2-6}$ alkynyl, trimethylsilanyl $C_{2-6}$ alkynyl, optionally substituted $C_{3-7}$ cycloalkyl, halogen, cyano, optionally substituted phenyl, optionally substituted heteroaryl or optionally substituted phenyl-$C_{1-6}$ methoxy-$C_{1-6}$ alkyl, furthermore preferably $R^6$ is $C_{2-6}$ alkynyl, halogen, cyano or optionally substituted heteroaryl, especially $R^6$ is pyridinyl, pyrimidinyl, iodo, ethynyl or cyano.

ix) A preferred compound of the invention is a compound of formula (I), which is

[2-(3-Hexyl-phenyl)-3-methyl-5-pyrimidin-5-yl-3H-imidazol-4-yl]-(4-pyrrolidin-1-yl-piperidin-1-yl)-methanone,

[5-Iodo-3-methyl-2-(3-trifluoromethoxy-phenyl)-3H-imidazol-4-yl]-(4-pyrrolidin-1-yl-piperidin-1-yl)-methanone,

[3-Methyl-5-pyrimidin-5-yl-2-(3-trifluoromethoxy-phenyl)-3H-imidazol-4-yl]-(4-pyrrolidin-1-yl-piperidin-1-yl)-methanone,

[3-Methyl-5-pyrimidin-5-yl-2-(3-trifluoromethyl-phenyl)-3H-imidazol-4-yl]-(4-pyrrolidin-1-yl-piperidin-1-yl)-methanone,

[5-Ethynyl-3-methyl-2-(3-trifluoromethyl-phenyl)-3H-imidazol-4-yl]-(4-pyrrolidin-1-yl-piperidin-1-yl)-methanone, 1-Methyl-5-(4-pyrrolidin-1-yl-piperidine-1-carbonyl)-2-(3-trifluoromethoxy-phenyl)-1H-imidazole-4-carbonitrile,

[3-Methyl-5-pyridin-4-yl-2-(3-trifluoromethoxy-phenyl)-3H-imidazol-4-yl]-(4-pyrrolidin-1-yl-piperidin-1-yl)-methanone,

[2-(3-Hexyl-phenyl)-5-iodo-3-methyl-3H-imidazol-4-yl]-[4-(2-hydroxymethyl-pyrrolidin-1-yl)-piperidin-1-yl]-methanone,

[4-(2-Hydroxymethyl-pyrrolidin-1-yl)-piperidin-1-yl]-[5-iodo-3-methyl-2-(3-trifluoromethoxy-phenyl)-3H-imidazol-4-yl]-methanone,

[4-(2-Hydroxymethyl-pyrrolidin-1-yl)-piperidin-1-yl]-[3-methyl-5-pyrimidin-5-yl-2-(3-trifluoromethoxy-phenyl)-3H-imidazol-4-yl]-methanone or

[4-(2-Hydroxymethyl-pyrrolidin-1-yl)-piperidin-1-yl]-[3-methyl-5-pyridin-4-yl-2-(3-trifluoromethoxy-phenyl)-3H-imidazol-4-yl]-methanone,

[3-Cyclopropyl-5-pyrimidin-5-yl-2-(3-trifluoromethyl-phenyl)-3H-imidazol-4-yl]-(4-pyrrolidin-1-yl-piperidin-1-yl)-methanone,

[3-Methyl-5-pyrimidin-5-yl-2-(4-trifluoromethoxy-phenyl)-3H-imidazol-4-yl]-(4-pyrrolidin-1-yl-piperidin-1-yl)-methanone,

[3-Cyclopropyl-5-pyridin-3-yl-2-(4-trifluoromethoxy-phenyl)-3H-imidazol-4-yl]-(4-pyrrolidin-1-yl-piperidin-1-yl)-methanone,

[3-Cyclopropyl-5-pyridin-3-yl-2-(4-trifluoromethoxy-phenyl)-3H-imidazol-4-yl]-[4-((S)-2-hydroxymethyl-pyrrolidin-1-yl)-piperidin-1-yl]-methanone,

[3-Cyclopropyl-5-pyrimidin-5-yl-2-(4-trifluoromethoxy-phenyl)-3H-imidazol-4-yl]-(4-pyrrolidin-1-yl-piperidin-1-yl)-methanone,

[5-(2-Amino-pyrimidin-5-yl)-3-cyclopropyl-2-(4-trifluoromethoxy-phenyl)-3H-imidazol-4-yl]-(4-pyrrolidin-1-yl-piperidin-1-yl)-methanone,

[5-(6-Amino-pyridin-3-yl)-3-cyclopropyl-2-(4-trifluoromethoxy-phenyl)-3H-imidazol-4-yl]-(4-pyrrolidin-1-yl-piperidin-1-yl)-methanone,

[3-Cyclopropyl-5-(1H-[1,2,4]triazol-3-yl)-2-(4-trifluoromethoxy-phenyl)-3H-imidazol-4-yl]-(4-pyrrolidin-1-yl-piperidin-1-yl)-methanone,

[3-Cyclopropyl-5-(1H-pyrazol-4-yl)-2-(4-trifluoromethoxy-phenyl)-3H-imidazol-4-yl]-(4-pyrrolidin-1-yl-piperidin-1-yl)-methanone,

[3-Cyclopropyl-5-(1H-[1,2,3]triazol-4-yl)-2-(4-trifluoromethoxy-phenyl)-3H-imidazol-4-yl]-(4-pyrrolidin-1-yl-piperidin-1-yl)-methanone,

[3-Cyclopropyl-5-(2-hydroxy-pyridin-4-yl)-2-(4-trifluoromethoxy-phenyl)-3H-imidazol-4-yl]-(4-pyrrolidin-1-yl-piperidin-1-yl)-methanone or

[3-Cyclopropyl-5-pyrimidin-5-yl-2-(4-trifluoromethoxy-phenyl)-3H-imidazol-4-yl]-[4-((S)-2-hydroxymethyl-pyrrolidin-1-yl)-piperidin-1-yl]-methanone.

General Synthetic Procedures

The compounds of formula (I) can be manufactured by methods known in the art, by the methods given below, by the methods given in the examples or by analogous methods. Appropriate reaction conditions for the individual reaction steps are known to a person skilled in the art. Starting materials are either commercially available or are known or can be prepared by methods given below or by methods described in the examples, or by methods known in the art. The syntheses of the compounds of general formula (I) are described in scheme 4, scheme 5 and scheme 6. Schemes 1-3 describe the synthesis of intermediates.

Aldehydes 1 (scheme 1) are known or can be prepared by methods known in the art, e.g. aldehydes with substituents equal to an alk-1-ynyl group can be prepared from aldehydes carrying bromo or iodo functions by reaction with an alk-1-yne under Sonogashira reaction conditions: treatment with copper (I) iodide and tetrakis-(triphenylphosphine)-palladium(0) in piperidine between room temperature and about 100° C. Optionally any substituent present in aldehyde 1 can be modified at any step of the synthesis, e.g. by hydrogenation of a double or a triple bond to a single bond. Imidazoles 2 can then be formed from aldehydes 1 by treatment with aqueous glyoxal and aqueous ammonium hydroxide in methanol preferably around 0° C. (step a).

Scheme 1

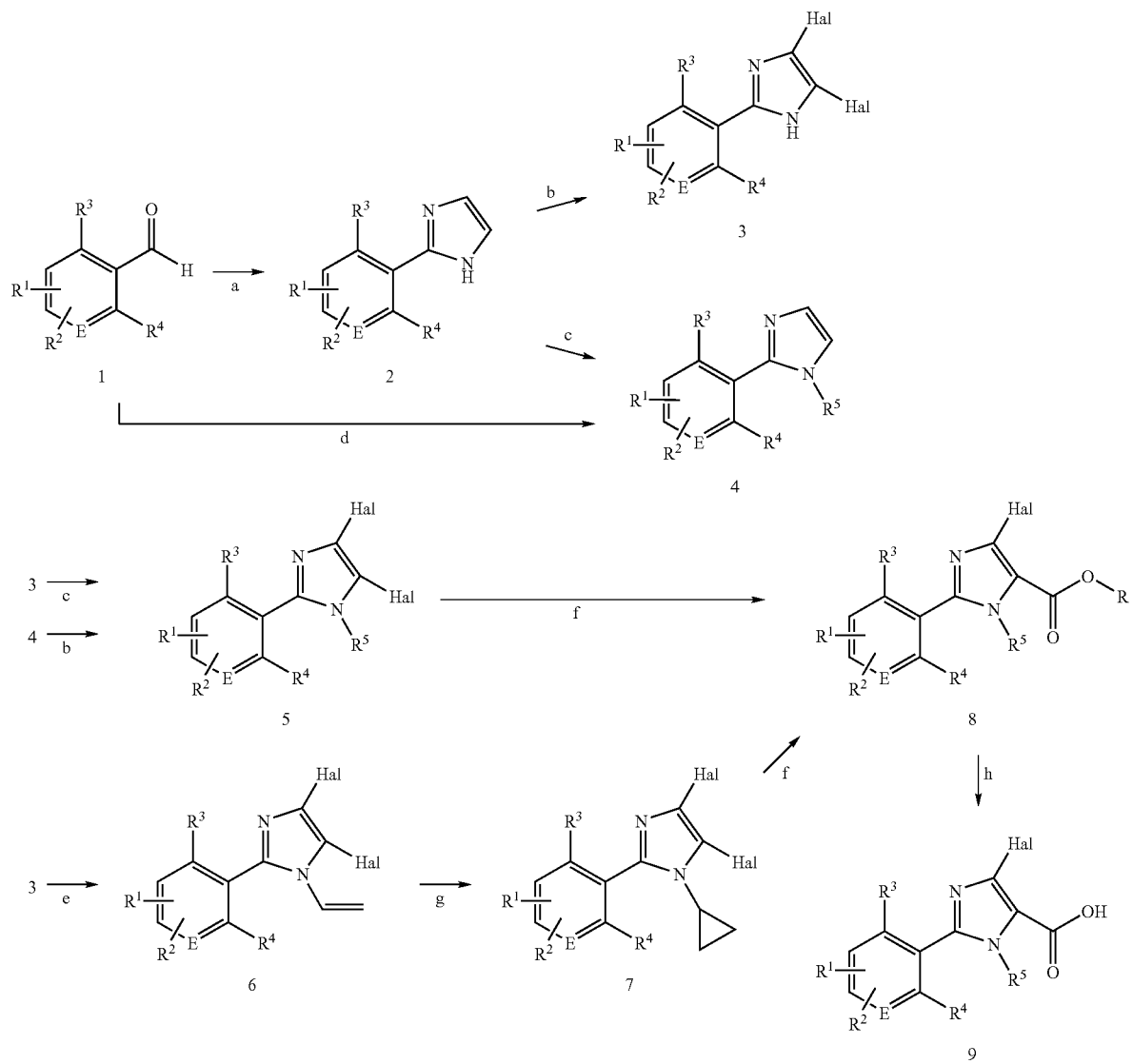

(In scheme 1, Hal, E, $R^1$, $R^2$, $R^3$, $R^4$ and $R^5$ are as defined before. R is $C_{1-6}$ alkyl.)

Di-halogenation of imidazoles 2 or 4 to dihalo-imidazoles 3 or 5 can be performed e.g. with iodine and silver sulfate in ethanol around RT, with N-chlorosuccinimide in a solvent, such as acetonitrile, at a temperature around 50° C. [Pringle, W. C.; Peterson, J. M.; Xie, L.; Ge, P.; Gao, Y.; Ochterski, J. W.; Lan, J. PCT Int. Appl. (2006) WO 2006089076 A2] or with bromine in a solvent like chloroform preferably at RT (step b). N-Alkylation of imidazoles 2 or 3 can be performed e.g. with an alkyl halide or an alkyl alkane- or aryl sulfonate with the help of a base, such as sodium hydride or potassium carbonate, in a solvent, such as N,N-dimethylformamide, preferably between 0° C. and about 140° C. (depending on the reactivity of the alkylating agent used) and gives N-alkyl imidazoles 4 or 5 (step c). Alternatively, substituted imidazoles 4 can directly be prepared from aldehydes 1 by treatment with aqueous glyoxal and either aqueous ammonium hydroxide or ammonium acetate, chloride or carbonate and a primary amine in a solvent, such as methanol or ethanol, in a temperature range between about 0° C. and the reflux temperature of the solvents [Matsuoka, Y.; Ishida, Y.; Sasaki, D.; Saigo, K. Tetrahedron (2006), 62(34), 8199-8206] (step d).

N-vinyl imidazoles 6 can be prepared by reaction of imidazoles 3 with 1,2-dibromoethane and 50% NaOH, tetrabutylammonium bromide, preferably under reflux conditions [Seley, K. L.; Januszczyk, P.; Hagos, A.; Zhang, L.; Dransfield, D. T. J. Med. Chem. 2000, 43, 4877-4883] or with toluene-4-sulfonic acid 2-chloro-ethyl ester in N,N-dimethylformamide in the presence of potassium carbonate preferably around 120° C. (alkylation followed by elimination) (step e). Cyclopropanation of N-vinyl imidazoles 6 can then be performed e.g. with diethyl zinc and chloro-iodo-methane or di-iodo-methane preferably in a solvent, such as dichloroethane, or in solvent mixtures of dichloroethane and dimethoxyethane in a temperature range between –15° C. and RT [in analogy to Maligres, P. E.; Waters, M. M.; Lee, J.; Reamer, R. A.; Askin, D.; Ashwood, M. S.; Cameron, M. J. Org. Chem. 2002, 67, 1093-1101 and Vu, T. C.; Brzozowski, D. B.; Fox, R.; Godfrey, J. D., Jr.; Hanson, R. L.; Kolotuchin, S. V.; Mazzullo, J. A., Jr.; Patel, R. N.; Wang, J.; Wong, K.; Yu, J.; Zhu, J.; Magnin, D. R.; Augeri, D. J.; Hamann, L. G. PCT Int. Appl. (2004), WO 2004052850 A2] (step g). Treatment of dihalo-imidazoles 5 or 7 either with n-butyl lithium (preferably at −78° C.) or an alkyl Grignard reagent (preferably between −50° C. and RT) in a solvent, such as tetrahydrofuran, gives metallated intermediates carrying the metal atom at the imidazole carbon atom adjacent to the substituted imidazole nitrogen atom [Butz, R. H. J.; Lindell, S. D. *Synthesis and Chemistry of 4,5-Dimagnesioimidazole Dianions. J. Org. Chem.* 2002, 67, 2699-2701]. Such intermediates then form adducts 8 or 9 when reacted with dialkyl carbonates or carbon dioxide, respectively, at temperatures between −78° C. and RT in case of lithiation or between −50° C. and RT or elevated temperatures in case of the imidazole magnesium adducts (step f). Esters 8 can then be saponified e.g. by use of lithium hydroxide in tetrahydrofuran/methanol/water at RT or elevated temperature to give acids 9 (step h).

Scheme 2

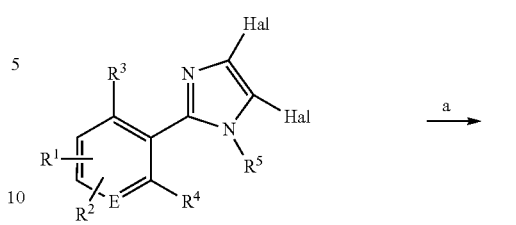

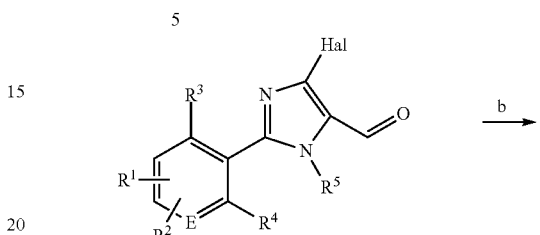

(In scheme 2, Hal, E, $R^1$, $R^2$, $R^3$, $R^4$ and $R^5$ are as defined before.)

Alternatively to the synthesis described in scheme 1, dihalo-arly imidazoles 5 can be prepared from trihalo-imidazoles 12 and aryl boronic acid derivatives 11 ($R^i$ is independently hydrogen, $C_{1-6}$ alkyl or both $R^i$'s together form a $C_{1-6}$ alkylene group) and a catalyst, such as tetrakis-(triphenylphosphine)-palladium(0), in a solvent, such as toluene, N,N-dimethylformamide, and a mixture thereof, and an aqueous or non-aqueous base in a temperature range preferably between 80° C. and 100° C. as e.g. described in [Pringle, W. C.; Peterson, J. M.; Xie, L.; Ge, P.; Gao, Y.; Ochterski, J. W.; Lan, J. PCT Int. Appl. (2006) WO 2006089076 A2] (step a).

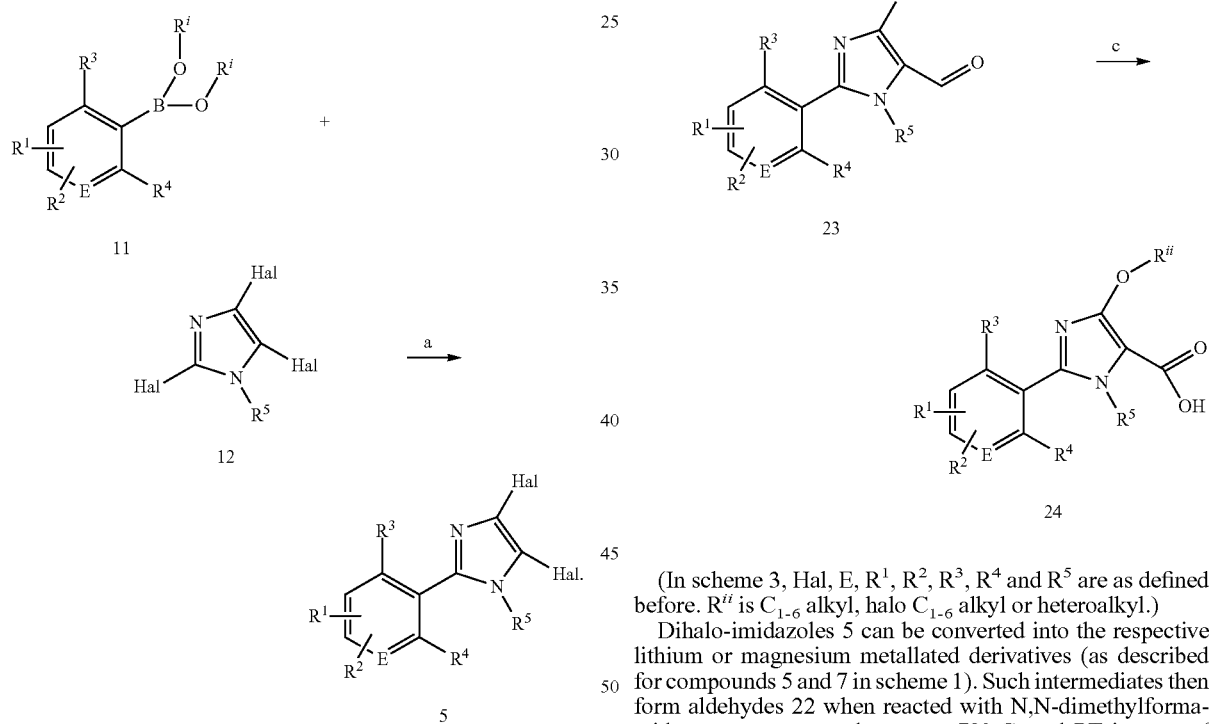

Scheme 3

(In scheme 3, Hal, E, $R^1$, $R^2$, $R^3$, $R^4$ and $R^5$ are as defined before. $R^{ii}$ is $C_{1-6}$ alkyl, halo $C_{1-6}$ alkyl or heteroalkyl.)

Dihalo-imidazoles 5 can be converted into the respective lithium or magnesium metallated derivatives (as described for compounds 5 and 7 in scheme 1). Such intermediates then form aldehydes 22 when reacted with N,N-dimethylformamide, at temperatures between −78° C. and RT in case of lithiation or between −50° C. and RT or elevated temperatures in case of the imidazole magnesium adducts (step a). Treatment of aldehydes 22 (preferably using aldehydes 22 with halogen equal to chlorine or bromine) with a sodium or potassium alcoholate or with an alcohol in the presence of a base, such as sodium hydroxide, in a temperature range between about 80° C. and about 140° C. gives ether compounds 23 [Kleemann, H-W.; Lang, H. J.; Schwark, J-R.; Petry, S.; Weichert, A. *Ger. Offen.* (2000), DE 19832428 A1](step b). Aldehydes 23 can then be oxidized to acids 24 e.g. with sodium chlorite, sodium dihydrogenphosphate-dihydrate in tert-butanol/water 2:1 in the presence of 2-methyl-2-butene preferably at room temperature, with silver nitrate, sodium hydroxide in acetonitrile/water or with manganese(IV) oxide, sodium cyanide in methanol/acetic acid giving the methyl ester that can be saponified subsequently (step c).

Scheme 4
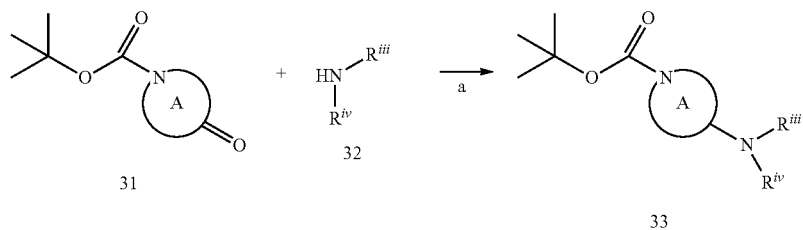
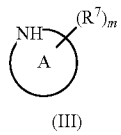
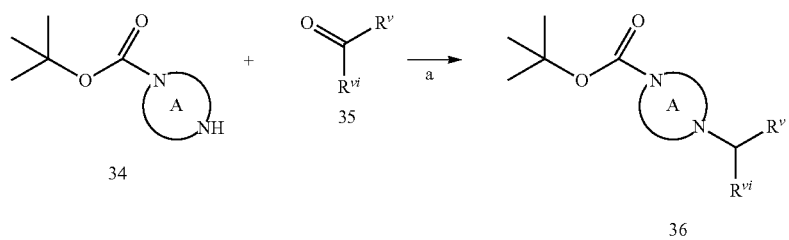
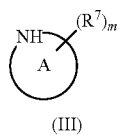
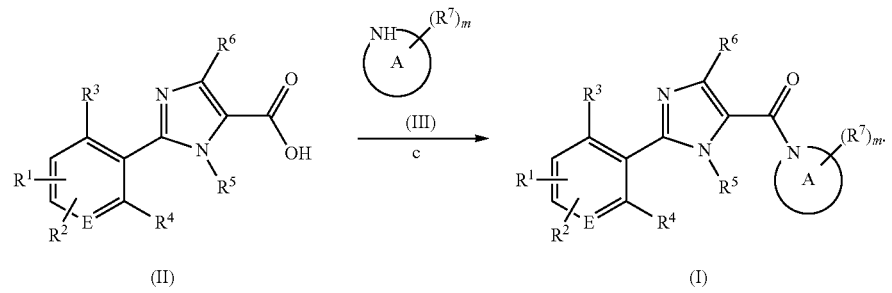

(In scheme 4,

m, E, $R^1$, $R^2$, $R^3$, $R^4$, $R^5$, $R^6$ and $R^7$ are as defined before.

is heterocyclyl, which is a non-aromatic mono-cyclic radical of four to eight ring atoms, in which two ring atoms are nitrogen atoms, the remaining ring atoms being carbon atoms. $R^{iii}$ and $R^{iv}$ are independently hydrogen, $C_{1-6}$ alkyl, heteroalkyl, optionally substituted $C_{3-7}$ cycloalkyl or optionally substituted heterocyclyl or

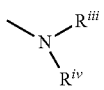

is optionally substituted heterocyclyl.

is $C_{1-6}$ alkyl, halo $C_{1-6}$ alkyl, heteroalkyl, $C_{2-6}$ alkenyl, $C_{2-6}$ alkynyl, hydroxy $C_{2-6}$ alkenyl, hydroxy $C_{2-6}$ alkynyl, $C_{1-6}$ alkoxy $C_{2-6}$ alkenyl, $C_{1-6}$ alkoxy $C_{2-6}$ alkynyl, optionally substituted $C_{3-7}$ cycloalkyl or optionally substituted $C_{3-7}$ cycloalkyl $C_{1-6}$ alkyl, optionally substituted heterocyclyl or optionally substituted heterocyclyl $C_{1-6}$ alkyl.)

Secondary amines (III) (scheme 4) are known, can be prepared by the methods known in the art or the methods described in the examples or can be prepared e.g. by reductive amination of ketones 31 with secondary amines 32 or by reductive amination of secondary amines 34 with ketones 35 e.g. by using sodium triacetoxy-borohydride, sodium cyanoborohydride or borane-pyridine complex as reagents in the presence of acetic acid and potentially a base, such as trietylamine, in a solvent, such as 1,2-dichloro-ethane, at temperatures around RT (step a). Such a reductive amination leads to Boc-protected adducts 33 or 36 which are subsequently deprotected by well established procedures as e.g. trifluoro-acetic acid with or without an additional solvent or alcoholic hydrogen chloride to give secondary amines (III) (step b). Imidazole carboxylic acids (II) can then be coupled with secondary amines (III) by coupling methods, such as use of O-(7-azabenzotriazol-1-yl)-1,1,3,3-tetramethyluronium hexafluorophosphate (HATU), triethyl amine in N,N-dimethylformamide or by reaction of the imidazole carboxylic acids (II) first with 2-chloro-4,6-dimethoxy-[1,3,5]triazine and N-methylmorpholine in acetonitrile followed by addition of the secondary amines (III) (0° C. to RT) (step c).

Scheme 5

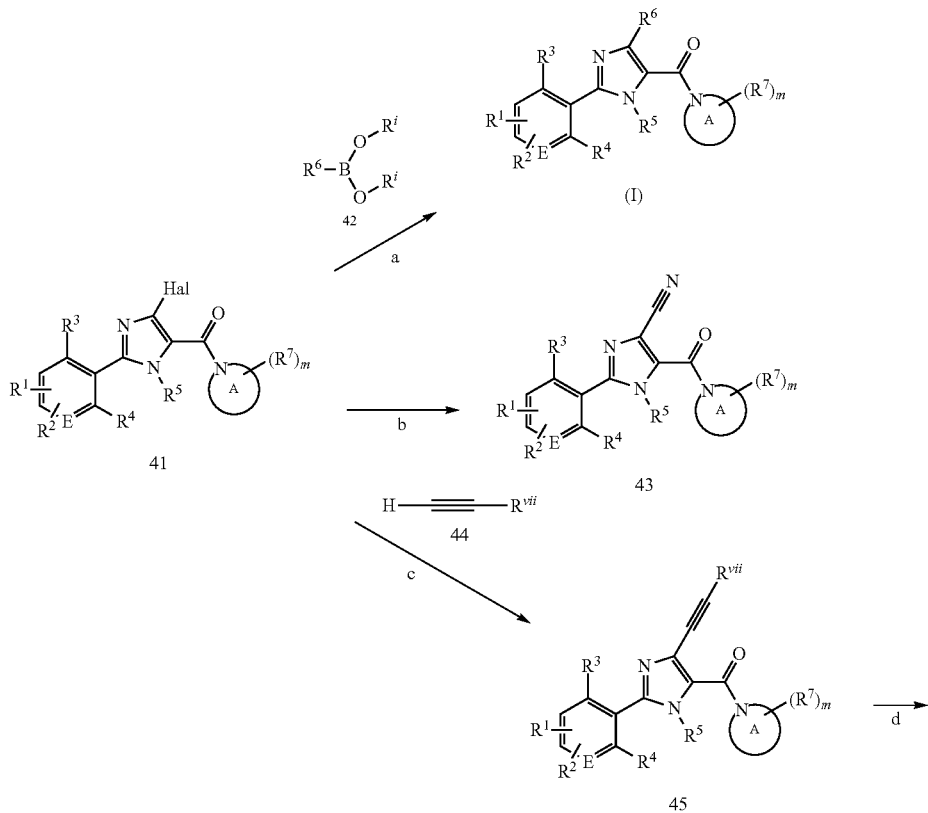

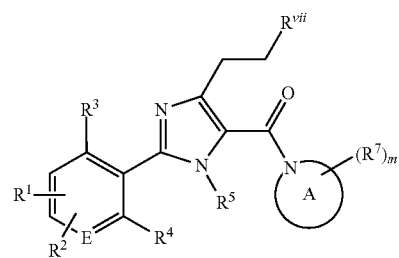

46

(In scheme 5,

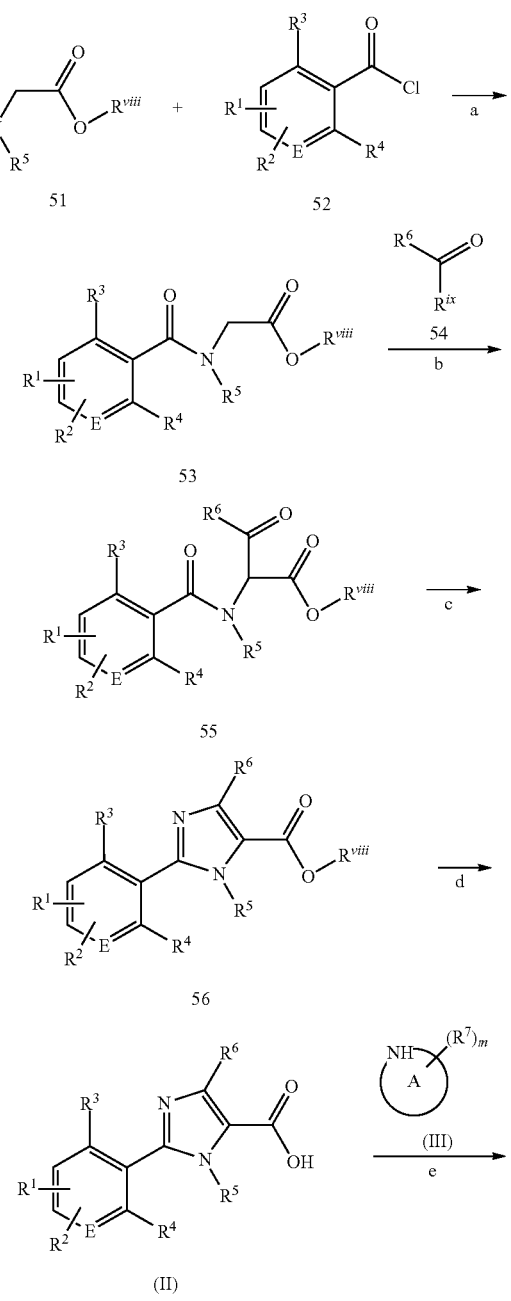

m, E, $R^1$, $R^2$, $R^3$, $R^4$, $R^5$, $R^6$ and $R^7$ are as defined before. $R^{vii}$ is $C_{1-4}$ alkyl, halo $C_{1-4}$ alkyl, heteroalkyl, optionally substituted $C_{3-7}$ cycloalkyl, optionally substituted $C_{3-7}$ cycloalkyl $C_{1-4}$ alkyl, optionally substituted benzyloxymethyl, optionally substituted benzyloxymethyl-$C_{1-4}$ alkyl, wherein heteroalkyl means $C_{1-4}$ alkyl substituted by one or more substituents selected independently from the group consisting of hydroxy, $C_{1-6}$ alkoxy, $C_{1-6}$ alkylthio or di-$C_{1-6}$ alkyl substituted amino.)

Substituted imidazoles (I), 43, 45 and 46 (scheme 5) can be prepared from haloimidazoles 41 by methods well known in the art. Suzuki coupling with boronic acids 42 in the presence of a catalyst, such as tetrakis-(triphenylphosphine)-palladium, and in the presence of a base, such as potassium phosphate, in a solvent, such as toluene or N,N-dimethylformamide, in a temperature range preferably between about 70° C. and about 130° C. gives imidazoles (I) ($R^i$ is independently hydrogen, $C_{1-6}$ alkyl or both $R^i$'s together form a $C_{1-6}$ alkylene group) (step a). Coupling with zinc cyanide in the presence of tetrakis-(triphenylphosphine)-palladium in a solvent, such as N,N-dimethylformamide, in a temperature range preferably between 130° C. and 150° C. gives cyanoimidazoles 43 (step b). Sonogashira coupling with a reagent 44 containing a terminal acetylene function in the presence of copper(I) iodide, tetrakis-(triphenylphosphine)-palladium, tetrabutylammonium iodide and triethylamine, preferably in a solvent, such as N,N-dimethylformamide, in a temperature range preferably between 50° C. and 80° C. gives imidazoles 45 carrying an acetylenic substituent (step c). The triple bond in the acetylenic substituent can optionally be reduced to a single bond by hydrogenation using e.g. $PtO_2$ as catalyst (step d). Optionally, $R^{vii}$ can be further modified: e.g. an $R^{vii}$ moiety carrying a hydroxyl function can be reacted with a benzylic halide in the presence of a base, such as sodium hydride in a solvent, such as N,N-dimethylformamide, in a temperature range preferably between 0° C. and 50° C. in order to attach a benzylic ether function.

-continued

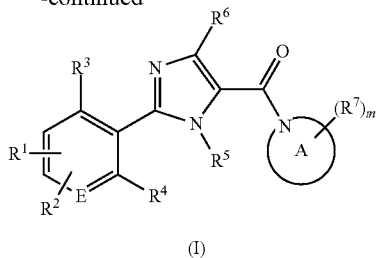

(I)

(In scheme 6,

m, E, $R^1$, $R^2$, $R^3$, $R^4$, $R^5$, $R^6$ and $R^7$ are as defined before. $R^{viii}$ is $C_{1-4}$ alkyl, $R^{ix}$ is halogen, imidazole-1yl or —O-(pyrrolidine-2,5-dione-1yl).

Alternatively, substituted imidazoles (I) can be prepared by a reaction sequence as depicted in scheme 6. Glycine esters 51 are reacted with acid chlorides 52 in solvents like dichloromethane in the presence of a base like saturated sodium hydrogen carbonate solution preferably at room temperature to give acyl glycine compounds 53 (step a). Enolates of acyl glycine compounds 53, optionally obtained by reaction with lithium hexamethyldisilazide at temperatures between −78° C. and −30° C. can be condensed with activated acid derivatives 54 preferably in a temperature range between −30° C. and room temperature to give intermediates 55 (step b). Intermediates 55 react with ammonium-trifluoroacetate at a temperature around 110° C. to form imidazole esters 56 (step c). Saponification of imidazole esters 56, e.g. with sodium hydroxide in ethanol at reflux, gives acids (II) (step d), which can be coupled with amines (III) to amides (I) as described in scheme 4 (step c).

In addition to the reaction steps explicitly described in schemes 1-6, optionally, additional well established synthetic structural modifications can be performed at any substituent at any stage of the syntheses described, as e.g. introduction and removal of protective groups.

As described above, the compounds of formula (I) are CCR-2 receptor antagonists, with some antagonist activity also at CCR-3 and CCR-5. These compounds consequently prevent migration of various leukocyte populations through the blockade of CCR-2 stimulation. They therefore can be used for the treatment and/or prevention of inflammatory and/or allergic diseases, such as peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable Bowel Disease, Crohns' disease, multiple sclerosis, neuropathic pain, atherothrombosis and/or burns/ulcers in Diabetes/CLI, and asthma. Prevention and/or treatment of inflammatory diseases, particularly peripheral arterial occlusive diseases or atherothrombosis is the preferred indication.

The invention therefore also relates to pharmaceutical compositions comprising a compound as defined above and a pharmaceutically acceptable excipient.

The invention likewise embraces compounds as described above for use as therapeutically active substances, especially as therapeutically active substances for the treatment and/or prophylaxis of inflammatory and/or allergic diseases, particularly as therapeutically active substances for the treatment and/or prophylaxis of peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable Bowel Disease, Crohns' disease, multiple sclerosis, neuropathic pain, atherothrombosis, burns/ulcers in Diabetes/CLI, and allergy, asthma.

The invention also relates to the use of compounds as described above for the preparation of medicaments for the therapeutic and/or prophylactic treatment of inflammatory and/or allergic diseases, particularly for the therapeutic and/or prophylactic treatment of peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable Bowel Disease, Crohns' disease, multiple sclerosis, neuropathic pain, atherothrombosis, burns/ulcers in Diabetes/CLI, and asthma. Such medicaments comprise a compound as described above.

The invention also relates to the process and the intermediates for manufacturing the compounds of formula (I) as well as the process for manufacturing the intermediates. CCR-2 receptor antagonistic activity by the compounds of the present invention can be demonstrated by the following assays.

Receptor Binding Assay

Binding assays were done with membranes from CHOK1-CCR2B-A5 cells (Euroscreen) stably overexpressing the human CCR2B.

Membranes were prepared by homogenizing the cells in 10 mM Tris pH 7.4, 1 mM EDTA, 0.05 mM benzamidine, leupeptin 6 mg/L and separating the debris at 1000 g. The membranes were then isolated at 100000 g in 50 mM Tris pH 7.4, $MgCl_2$ 10 mM, EGTA 1 mM, glycerol 10%, benzamidine 0.05 mM, leupeptine 6 mg/l.

For binding, CCR2 antagonist compounds were added in various concentrations in 50 mM HEPES pH 7.2, 1 mM $CaCl_2$, 5 mM $MgCl_2$, 0.5% BSA, 0.01% $NaN_3$, together with 100 pM $^{125}$I-MCP-1 (PerkinElmer, 2200 Ci/mmol) to about 5 fMol CCR2 membranes and incubated for 1 hour at room temperature. For unspecific control 57.7 nM MCP-1 (R&D Systems or prepared at Roche) was added. Membranes were harvested through GF/B (glass fiber filter; PerkinElmer) plates, equilibrated with 0.3% polyethylenimine; 0.2% BSA, air dried and binding was determined by counting in a topcounter (NXT Packard). Specific binding was defined as total binding minus nonspecific binding and typically represents about 90-95% of the total binding. Antagonist activity is indicated as inhibitor concentration required for 50% inhibition ($IC_{50}$) of specific binding.

Calcium Mobilization Assay

CHOK1-CCR2B-A5 cells (from Euroscreen) stably overexpressing the human chemokine receptor 2 isoform B were cultured in Nutrient Hams F12 medium supplemented with 5% FBS, 100 U/ml penicillin, 100 μg/ml streptomycin, 400 μg/ml G418 and 5 μg/ml puromycin. For the assay cells were grown overnight in 384-well black clear flat bottom polystyrene plates (Costar) at 37° C. at 5% $CO_2$. After washing with DMEM, 20 mM Hepes, 2.5 mM probenecid, 0.1% BSA (DMEM assay buffer) cells were loaded with 4 μM Fluo-4 in the same DMEM assay buffer for 2 hours at 30° C. Excess dye was removed and cells were washed with DMEM assay buffer. 384-well compound plates were prepared with DMEM assay buffer/0.5% DMSO with or without various concentrations of test compounds. Usually compounds were tested for agonist and antagonist activity.

Test compounds were added to the assay plate and agonist activity was monitored as fluorescence for 80 seconds with a FLIPR (488 nm excitation; 510-570 nm emission; Molecular Devices). After 20-30 min. of incubation at 30° C., 20 nM MCP-1 (R&D; Roche) was added and fluorescence was monitored again for 80 seconds. Increases in intracellular calcium are reported as maximum fluorescence after agonist exposure minus basal fluorescence before exposure. Antagonist activity is indicated as inhibitor concentration required for 50% inhibition of specific calcium increases.

The compounds of general formula (I) exhibit IC50 values in the Ca mobilisation assay or in the receptor binding assay of 0.1 nM to 10 µM, preferably 1 nM to 1.5 µM for CCR2. The following table shows measured values in the calcium mobilization assay for some selected compounds of the present invention.

| Example | IC50(µM) | Example | IC50(µM) |
|---------|----------|---------|----------|
| 1       | 0.12     | 25      | 0.071    |
| 3       | 0.13     | 36      | 0.018    |
| 13      | 0.035    | 22      | 0.090    |
| 18      | 0.075    | 46      | 0.16     |

The compounds of formula (I) and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula (I).

The following Examples serve to illustrate the present invention in more detail. They are, however, not intended to limit its scope in any manner.

EXAMPLES

Abbreviations

AcOH=Acetic acid, BOC=t-Butyloxycarbonyl, BuLi=Butyllithium, CDI=1,1-carbonyldiimidazole, $CH_2Cl_2$=dichloromethane, DCE=1,2-dichloroethane, DIBALH=Di-i-butylaluminium hydride, DCC=N,N'-Dicyclohexylcarbodiimide, DMA=N,N-Dimethylacetamide, DMAP=4-Dimethylaminopyridine, DMF=N,N-Dimethylformamide, EDCI=N-(3-Dimethylaminopropyl)-N'-ethylcarbodiimide hydrochloride, EtOAc=Ethylacetate, EtOH=Ethanol, $Et_2O$=Diethylether, $Et_3N$=Triethylamine, eq=Equivalents, HATU=O-(7-azabenzotriazol-1-yl)-1,1,3,3-tetramethyluronium hexafluorophosphate, HOBT=1-Hydroxybenzo-triazole, Huenig's base=$iPr_2NEt$=N-Ethyl diisopropylamine, LAH=Lithium aluminium hydride, LDA=Lithium diisopropylamide, $LiBH_4$=Lithium borohydride, MeOH=Methanol, NaI=Sodium iodide, Red-Al=Sodium bis(2-methoxyethoxy)aluminium hydride, RT=room temperature, TBDMSCI=t-Butyldimethylsilyl chloride, TFA=Trifluoroacetic acid, THF=Tetrahydrofurane, quant=quantitative.

General Remarks

All reactions were performed under argon.

Intermediate 1

2-(3-Hexyl-phenyl)-5-iodo-3-methyl-3H-imidazole-4-carboxylic acid

A) 3-Hex-1-ynyl-benzaldehyde

A solution of 10.0 g (54.05 mmol) of 3-bromo-benzaldehyde in 150 ml of piperidine was treated at RT with 1.029 g (5.40 mmol) of copper(I)iodide and 6.246 g (5.40 mmol) of tetrakis-(triphenylphosphine)-palladium and the mixture was then warmed up to 60° C. After 10 min, a solution of 9.30 ml=6.66 g (81.07 mmol) of hex-1-yne in 150 ml of piperidine was added drop by drop during 1 hour. After 30 min, the oil bath temperature was steadily increased to 80° C. The reaction mixture was then stirred at 80° C. for 15 hours and subsequently cooled down to RT. The solvent was evaporated and the residue poured into crashed ice, acidified with HCl (37%) to pH 2-3 and extracted twice with EtOAc; the organic phases were washed with water, dried over magnesium sulfate, filtered and evaporated. The residue was purified by flash column chromatography (n-heptane/EtOAc 1:0 to 97:3) to give 8.78 g (87%) of the title compound as yellow oil. MS: 186.2 ($M^+$).

B) 2-(3-Hex-1-ynyl-phenyl)-1H-imidazole

A solution of 8.60 g (46.17 mmol) of 3-hex-1-ynyl-benzaldehyde in 200 ml of MeOH was treated with 60.47 ml=55.02 g (392.5 mmol) of ammonium hydroxide (25% in water) and cooled down to 0° C. Then, 34.29 ml=43.55 g (300 mmol) of glyoxal solution (40% in water) was added to this mixture drop by drop between 0° C. and 8° C. Then, the reaction was kept at 0° C. for 68 hours and subsequently poured into crashed ice and extracted four times with EtOAc; the organic phases were washed with water, dried over magnesium sulfate, filtered and evaporated. The residue was purified by flash column chromatography ($CH_2Cl_2$/MeOH 1:0 to 96:4) to give 5.33 g (51%) of the title compound as light brown solid. MS: 225.2 ($MH^+$).

C) 2-(3-Hexyl-phenyl)-1H-imidazole

A solution of 6.15 g (27.4 mmol) of 2-(3-hex-1-ynyl-phenyl)-1H-imidazole in 140 ml of MeOH was treated with 1.46 g (1.4 mmol) of Pd—C (10%) and hydrogenated with $H_2$ (1 bar) at RT for 1 hour. After removal the catalyst by filtration, the solvent was evaporated. The residue was purified by flash column chromatography ($CH_2Cl_2$/MeOH 1:0 to 98:2) to give 5.92 g (95%) of the title compound as light brown solid. MS: 229.2 ($MH^+$).

D) 2-(3-Hexyl-phenyl)-4,5-diiodo-1H-imidazole

A solution of 5.60 g (24.52 mmol) of 2-(3-hexyl-phenyl)-1H-imidazole in 250 ml of MeOH or EtOH was treated with 8.265 g (26.24 mmol) of silver sulphate, followed by addition of 13.072 g (51.5 mmol) of iodine in small portions between 22° C. and 25° C. After 1 hour, ca. 6 ml of sodium thiosulfate solution (0.1 molar in water) was added, until the color of the reaction mixture changed from dark brown to yellow. The mixture was then poured into crashed ice and extracted twice with EtOAc; the organic phases were washed with water, dried over magnesium sulfate, filtered and evaporated. The residue was purified by flash column chromatography ($CH_2Cl_2$) to give 8.45 g (72%) of the title compound as light yellow solid. MS: 480.9 ($MH^+$).

E) 2-(3-Hexyl-phenyl)-4,5-diiodo-1-methyl-1H-imidazole

A solution of 8.45 g (17.6 mmol) of 2-(3-hexyl-phenyl)-4,5-diiodo-1H-imidazole in 150 ml of DMF was treated at 0° C. with 0.806 g (18.5 mmol) of sodium hydride (55% dispersion in mineral oil); 15 min later, a solution of 1.52 ml=3.47 g (24.2 mmol) of iodomethane in 25 ml of DMF was added drop by drop at 0° C. After 2 hours, the reaction mixture was poured into crashed ice and extracted twice with EtOAc; the organic phases were washed with water, dried over magnesium sulfate, filtered and evaporated. The residue was purified by flash column chromatography (n-heptane/EtOAc 1:0 to 4:1) to give 7.52 g (87%) of the title compound as light red oil. MS: 495.1 ($MH^+$).

F) 2-(3-Hexyl-phenyl)-5-iodo-3-methyl-3H-imidazole-4-carboxylic acid

A solution of 7.27 g (14.7 mmol) of 2-(3-hexyl-phenyl)-4,5-diiodo-1-methyl-1H-imidazole in 150 ml of THF was cooled down to −75° C.; then, 11.95 ml (19.1 mmol) of an n-butyl lithium solution (1.6 molar in n-hexane) was added drop by drop below −70° C. 30 min later, the reaction mixture was treated with an excess of solid carbon dioxide and subsequently warmed up to RT. It was then poured into crashed ice and extracted twice with EtOAc; the organic phases were washed with water, dried over magnesium sulfate, filtered and evaporated. The residue was purified by flash column chromatography ($CH_2Cl_2$/MeOH 1:0 to 4:1) to give 2.97 g (49%) of the title compound as light red oil. MS: 411.2 ($[M-H]^-$).

Intermediate 2

((R)-1-Piperidin-4-yl-pyrrolidin-2-yl)-methanol di-hydrochloride

A) 4-((R)-2-Hydroxymethyl-pyrrolidin-1-yl)-piperidine-1-carboxylic acid tert-butyl ester A solution of 5.98 g (30.0 mmol) of 4-oxo-piperidine-1-carboxylic acid tert-butyl ester and 3.55 ml=3.64 g (36.0 mmol) of (R)-(−)-pyrrolidin-2-yl-methanol in 60.0 ml of EtOH was treated with 60.0 ml of 1,2-dichloroethane, followed by 4.50 ml (36 mmol) of borane-pyridine complex (8 molar). Then, 4.46 ml=4.68 g (78.0 mmol) of acetic acid was added to this solution. After stirring at RT for 16 hours, the reaction mixture was poured into crashed ice; then, the pH was adjusted to 9-10 with sodium carbonate solution and the mixture was extracted twice with EtOAc; the combined organic phases were washed with water, dried over $MgSO_4$, filtered and evaporated. The residue was purified by flash column chromatography ($CH_2Cl_2$/MeOH 1:0 to 8:2) to give 7.69 g (90%) of the title compound as light yellow oil. MS: 285.1 ($MH^+$).

B) ((R)-1-Piperidin-4-yl-pyrrolidin-2-yl)-methanol di-hydrochloride

A solution of 8.80 g (30.9 mmol) of 4-((R)-2-hydroxymethyl-pyrrolidin-1-yl)-piperidine-1-carboxylic acid tert-butyl ester in 200 ml of EtOH was treated at RT with 15.5 ml (62.0 mmol) of hydrochloric acid in 1,4-dioxane (4 molar) and the mixture was heated up to 100° C. After two hours, the solvents were evaporated and the residue was re-crystallized from MeOH/MeCN and $Et_2O$ to give 6.53 g (82%) of the title compound as off-white solid. MS: 185.1 ($MH^+$).

Intermediate 3

1-Cyclopropylmethyl-4,5-diiodo-2-(3-trifluoromethyl-phenyl)-1H-imidazole

A suspension of 3.712 g (8.0 mmol) of 4,5-diiodo-2-(3-trifluoromethyl-phenyl)-1H-imidazole (prepared in analogy to the procedures described for intermediates 1B and 1D by i) transformation of 3-trifluoromethyl-benzaldehyde into 2-(3-trifluoromethyl-phenyl)-1H-imidazole; ii) iodination of 2-(3-trifluoromethyl-phenyl)-1H-imidazole to give 4,5-diiodo-2-

(3-trifluoromethyl-phenyl)-1H-imidazole), 0.266 g (1.6 mmol) of potassium iodide and 3.317 g (24 mmol) of potassium carbonate in 50 ml of DMF was treated at RT with 0.95 ml=1.35 g (10.0 mmol) of 1-(bromomethyl)cyclopropane; then reaction mixture was warmed up to 120° C. After washed with water, dried over magnesium sulfate, filtered and evaporated. The residue was purified by flash column chromatography (n-heptane/EtOAc 1:0 to 4:1) to give 2.63 g (63%) of the title compound as light red oil. MS: 518.7 ($MH^+$).

Intermediate 4

1-Cyclopropyl-4,5-diiodo-2-(3-trifluoromethyl-phenyl)-1H-imidazole

A) 1-Cyclopropyl-2-(3-trifluoromethyl-phenyl)-1H-imidazole 8.17 ml=6.62 g (113.6 mmol) of cyclopropylamine and 8.90 g (113.6 mmol) of ammonium acetate were added to a solution of 6.80 g (37.9 mmol) of 3-(trifluoromethyl)benzaldehyde in 60 ml of MeOH and the reaction mixture was cooled down to 0° C. While stirring, 9.59 ml=16.49 g (113.6 mmol) of glyoxal solution (40% in water) was added and then the reaction was warmed up to 50° C. After cooling down to RT, the solvents were evaporated and the residue dissolved in water and $Et_2O$. The reaction mixture was extracted three times with $Et_2O$; the organic phases were washed with water, dried over magnesium sulfate, filtered and evaporated. The residue was purified by flash column chromatography ($CH_2Cl_2$) to give 1.96 g (21%) of the title compound as light red oil. MS: 253.1 ($MH^+$).

B) 1-Cyclopropyl-4,5-diiodo-2-(3-trifluoromethyl-phenyl)-1H-imidazole

A solution of 2.45 g (9.71 mmol) of 1-cyclopropyl-2-(3-trifluoromethyl-phenyl)-1H-imidazole in 100 ml of EtOH was treated with 3.27 g (10.39 mmol) of silver sulphate, followed by addition of 5.18 g (20.4 mmol) of iodine in small portions between 22° C. and 25° C. After 3 hours, ca. 12 ml of sodium thiosulfate solution (0.1 molar in water) was added, until the color of the reaction mixture changed from dark brown to yellow. The mixture was then poured into crashed ice and extracted three times with EtOAc; the organic phases were washed with water, dried over magnesium sulfate, filtered and evaporated. The residue was purified by flash column chromatography (n-heptane/EtOAc 9:1 to 85:5) to give 1.96 g (40%) of the title compound as colorless oil. MS: 504.9 ($MH^+$).

Intermediate 5

4,5-Dibromo-2-(3-trifluoromethoxy-phenyl)-1H-imidazole

To a suspension of 9.40 g (41.2 mmol) of 2-(3-trifluoromethoxy-phenyl)-1H-imidazole (example 19) in 300 ml of $CHCl_3$ was added a solution of 4.23 ml=13.17 g (82.4 mmol) of bromine in $CHCl_3$ (100 ml). After stirring at RT for 3 hours, the reaction mixture was poured into crashed ice and the phases were separated. The organic phase was dried over magnesium sulfate, filtered and evaporated. The residue was purified by flash column chromatography ($CH_2Cl_2$) to give 7.60 g (48%) of the title compound as colorless amorphous solid. MS: 384.8 ($MH^+$, 2Br, lowest mass peak).

Intermediate 6

Benzoic acid(S)-1-piperidin-4-yl-pyrrolidin-2-ylmethyl ester

A) 4-((S)-2-Hydroxymethyl-pyrrolidin-1-yl)-piperidine-1-carboxylic acid tert-butyl ester A solution of 10.0 g (50.2 mmol) of 4-oxo-piperidine-1-carboxylic acid tert-butyl ester and 6.00 ml=6.15 g (60.2 mmol) of (S)-(−)-pyrrolidin-2-yl-methanol in 100.0 ml of EtOH was treated with 100.0 ml of 1,2-dichloroethane, followed by 7.53 ml (60.2 mmol) of borane-pyridine complex (8 molar). Then, 7.46 ml=7.84 g (130.5 mmol) of acetic acid was added to this solution. After stirring at RT for 16 hours, the reaction mixture was poured into crashed ice; then, the pH was adjusted to 9-10 with sodium carbonate solution and the mixture was extracted twice with EtOAc; the combined organic phases were washed with water, dried over $MgSO_4$, filtered and evaporated. The residue was purified by flash column chromatography ($CH_2Cl_2$/MeOH 1:0 to 9:1) to give 10.4 g (73%) of the title compound as light yellow oil. MS: 285.1 ($MH^+$).

B) 4-((S)-2-Benzoyloxymethyl-pyrrolidin-1-yl)-piperidine-1-carboxylic acid tert-butyl ester 3.35 g (11.8 mmol) of 4-((S)-2-hydroxymethyl-pyrrolidin-1-yl)-piperidine-1-carboxylic acid tert-butyl ester was dissolved in 55 ml of THF at RT and treated with 0.57 g (13.0 mmol) of sodium hydride (55% in mineral oil). 1.68 ml=2.03 g (14.1 mmol) of benzoyl chloride was added drop by drop and stirring continued for 2 hours. The reaction mixture was then poured into crashed ice and extracted three times with EtOAc; the organic phases were washed with water, dried over magnesium sulfate, filtered and evaporated. The residue was purified by flash column chromatography ($CH_2Cl_2$/MeOH 1:0 to 95:5) to give 2.80 g (61%) of the title compound as yellow oil. MS: 389.3 ($MH^+$).

C) Benzoic acid(S)-1-piperidin-4-yl-pyrrolidin-2-ylmethyl ester

To a solution of 2.78 g (7.2 mmol) of 4-((S)-2-benzoyloxymethyl-pyrrolidin-1-yl)-piperidine-1-carboxylic acid tert-butyl ester in 80 ml of $CH_2Cl_2$ was added 5.83 ml of TFA (90% in water) drop by drop. After 16 hours, the reaction mixture was poured into crashed ice; then, the pH was adjusted to 9-10 with sodium carbonate solution and the mixture was extracted three times with $CH_2Cl_2$; the organic phases were washed with water, dried over magnesium sulfate, filtered and evaporated. The residue was purified by flash column chromatography [$CH_2Cl_2$ (sat. with $NH_3$) and MeOH 1:0 to 9:1] to give 1.96 g (95%) of the title compound as yellow oil. MS: 289.1 ($MH^+$).

Intermediate 7

3-Cyclopropyl-5-methyl-2-(4-trifluoromethoxy-phenyl)-3H-imidazole-4-carboxylic acid A) Cyclopropylamino-acetic acid ethyl ester To a solution of 10 g (0.18 mol) of cyclopropylamine in 50 ml of EtOH was added 7 g (0.04 mol) of ethylbromoacetate and the reaction stirred for 1 h. The reaction was then evaporated to dryness, redissolved in $CH_2Cl_2$ washed with water, dried over sodium sulfate and concentrated to afford 6 g (quant.) of the title compound as a colorless oil. MS: 144.1 (MH$^+$).

B) [Cyclopropyl-(4-trifluoromethoxy-benzoyl)-amino]-acetic acid ethyl ester

To a vigorously stirred solution of 4.9 g (34 mmol) of cyclopropylamino-acetic acid ethyl ester in 50 ml of CH$_2$Cl$_2$ and 25 ml of saturated sodium hydrogen carbonate was added a solution of 8.4 g (37 mmol) of 4-(trifluoromethoxy)benzoyl chloride in 10 ml of CH$_2$Cl$_2$ and the reaction stirred for 1 h. The organic phase was then separated, dried with sodium sulfate and concentrated. Purification by flash column chromatography [n-heptane/EtOAc 1:9 to 3:7] afforded 8.9 g (80%) of the title compound as a colorless oil. MS: 332.1 (MH$^+$).

C) 2-[Cyclopropyl-(4-trifluoromethoxy-benzoyl)-amino]-3-oxo-butyric acid ethyl ester To a solution of 6.6 ml (1 M in THF, 7 mmol) of lithium hexamethyldisilylazide cooled to −78° C. under Ar was added, drop wise, a solution of 2.0 g (6 mmol) of [cyclopropyl-(4-trifluoromethoxy-benzoyl)-amino]-acetic acid ethyl ester in 10 ml of THF. The mixture was stirred for 1 h before 0.7 g of acetic anhydride was added and the mixture was allowed to reach room temperature. After 2 h the reaction was diluted with EtOAc, washed with saturated ammonium chloride solution, the organic phase dried with sodium sulfate and concentrated. Purification by flash column chromatography [n-heptane/EtOAc 1:9 to 3:7] afforded 0.3 g (13%) of the title compound as a colorless oil. MS: 374.2 (MH$^+$).

D) 3-Cyclopropyl-5-methyl-2-(4-trifluoromethoxy-phenyl)-3H-imidazole-4-carboxylic acid ethyl ester To 0.15 g (0.4 mmol) of 2-[cyclopropyl-(4-trifluoromethoxy-benzoyl)-amino]-3-oxo-butyric acid ethyl ester in 5 ml of MeOH was added 0.2 g (1.5 mmol) of ammonium trifluoroacetate. The MeOH was evaporated and the residue heated to 110° C. for 4 h. The cooled residue was partitioned between saturated sodium hydrogen carbonate solution and CH$_2$Cl$_2$. The organic phase was dried with sodium sulfate and concentrated. Purification by flash column chromatography [n-heptane/EtOAc 3:7 to 1:1] afforded 0.1 g (73%) of the title compound as a colorless solid. MS: 355.2 (MH$^+$).

E) 3-Cyclopropyl-5-methyl-2-(4-trifluoromethoxy-phenyl)-3H-imidazole-4-carboxylic acid To 0.1 g (0.3 mmol) of 3-cyclopropyl-5-methyl-2-(4-trifluoromethoxy-phenyl)-3H-imidazole-4-carboxylic acid ethyl ester in 3 ml of EtOH was added 61 microliters of 6 M sodium hydroxide solution (0.4 mmol) and the mixture heated to reflux for 6 h. The solvent was then evaporated, 1M hydrochloric acid solution was added and the resulting precipitate was isolated by filtration, affording 0.06 g (62%) of the title compound as a white solid. MS: 327.1 (MH$^+$).

Intermediate 8

3-Cyclopropyl-5-pyridin-3-yl-2-(4-trifluoromethoxy-phenyl)-3H-imidazole-4-carboxylic acid sodium salt

A) 2-[Cyclopropyl-(4-trifluoromethoxy-benzoyl)-amino]-3-oxo-3-pyridin-3-yl-propionic acid ethyl ester To solution of 12.7 ml (1 M in THF, 13 mmol) of lithium hexamethyldisilylazide cooled to −78° C. under Ar was added, drop wise, a solution of 3.8 g (12 mmol) of [cyclopropyl-(4-trifluoromethoxy-benzoyl)-amino]-acetic acid ethyl ester (intermediate 7B) in 20 ml of THF. The mixture was brought to −30° C. and stirred for 1 h. Separately, 0.6 g (5 mmol) of nicotinic acid was added to 0.8 g (5 mmol) of 1,1-carbonyl diimidazole in 10 ml of CH$_2$Cl$_2$ and the mixture stirred for 1 h after which time it was concentrated to dryness. The crude residue was re-dissolved in 10 ml of THF under Ar and cooled to −30° C. The enolate solution of intermediate 7B (described above) was then added by cannula to the crude imidazolide solution and the mixture was allowed to reach room temperature. After 2 h the reaction was diluted with EtOAc, washed with saturated ammonium chloride solution, the organic phase dried with sodium sulfate and concentrated. Purification by flash column chromatography [n-heptane/EtOAc 1:1] afforded 1.2 g (58%) of the title compound as an orange oil. MS: 437.2 (MH$^+$).

B) 3-Cyclopropyl-5-pyridin-3-yl-2-(4-trifluoromethoxy-phenyl)-3H-imidazole-4-carboxylic acid ethyl ester To 1.2 g (3 mmol) of 2-[cyclopropyl-(4-trifluoromethoxy-benzoyl)-amino]-3-oxo-3-pyridin-3-yl-propionic acid ethyl ester in 10 ml of EtOH was added 1.4 g (11 mmol) of ammonium trifluoroacetate. The EtOH was evaporated and the residue heated to 110° C. for 4 h. The cooled residue was partitioned between saturated sodium hydrogen carbonate solution and CH$_2$Cl$_2$. The organic phase was dried with sodium sulfate and concentrated. Purification by flash column chromatography [n-heptane/EtOAc 3:7 to 1:1] afforded 0.9 g (80%) of the title compound as a colorless solid. MS: 418.2 (MH$^+$).

C) 3-Cyclopropyl-5-pyridin-3-yl-2-(4-trifluoromethoxy-phenyl)-3H-imidazole-4-carboxylic acid sodium salt To 0.9 g (2 mmol) 3-cyclopropyl-5-pyridin-3-yl-2-(4-trifluoromethoxy-phenyl)-3H-imidazole-4-carboxylic acid ethyl ester in 5 ml of EtOH was added 0.4 ml of 6 M sodium hydroxide solution (2 mmol) and the mixture heated to reflux for 6 h. The solvent was then evaporated, affording 1.0 g (quant.) of the title compound as a white solid. MS: 390.1 (MH$^+$).

Intermediate 9

3-Cyclopropyl-5-(6-hydroxy-pyridin-3-yl)-2-(4-trifluoromethoxy-phenyl)-3H-imidazole-4-carboxylic acid

A) 3-(6-Benzyloxy-pyridin-3-yl)-2-[cyclopropyl-(4-trifluoromethoxy-benzoyl)-amino]-3-oxo-propionic acid ethyl ester The title compound, a colorless oil (1.5 g, 62%), was prepared in analogy to intermediate 8A by reaction of [cyclopropyl-(4-trifluoromethoxy-benzoyl)-amino]-acetic acid ethyl ester (intermediate 7B) with 6-(benzyloxy)nicotinic acid. MS: 543.2 (MH$^+$).

B) 3-Cyclopropyl-5-(6-hydroxy-pyridin-3-yl)-2-(4-trifluoromethoxy-phenyl)-3H-imidazole-4-carboxylic acid ethyl ester To 1.4 g (3 mmol) of 3-(6-benzyloxy-pyridin-3-yl)-2-[cyclopropyl-(4-trifluoromethoxy-benzoyl)-amino]-3-oxo-propionic acid ethyl ester in 5 ml of EtOH was added 1.4 g (10 mmol) of ammonium trifluoroacetate. The EtOH was evaporated and the residue heated to 110° C. for 16 h. The cooled residue was partitioned between saturated sodium hydrogen carbonate solution and $CH_2Cl_2$. The organic phase was dried with sodium sulfate and concentrated. The crude reside was re-dissolved in 10 ml of EtOH, a generous spatula of 10% palladium on activated charcoal was added, and the mixture stirred under an atmosphere of hydrogen for 1 h. The mixture was then filtered over Hyflo and concentrated. Purification by flash column chromatography [MeOH/EtOAc 4:96 to 1:9] afforded 0.8 g (70%) of the title compound as a colorless solid. MS: 434.2 ($MH^+$).

C) 3-Cyclopropyl-5-(6-hydroxy-pyridin-3-yl)-2-(4-trifluoromethoxy-phenyl)-3H-imidazole-4-carboxylic acid To 0.8 g (1.8 mmol) of 3-cyclopropyl-5-(6-hydroxy-pyridin-3-yl)-2-(4-trifluoromethoxy-phenyl)-3H-imidazole-4-carboxylic acid ethyl ester in 3 ml of EtOH was added 0.6 ml of 6 M sodium hydroxide solution (3.8 mmol) and the mixture was heated to reflux for 16 h. The solvent was then evaporated, 1M hydrochloric acid solution was added and the resulting precipitate was isolated by filtration, affording 0.7 g (94%) of the title compound as a white solid. MS: 406.1 ($MH^+$).

Intermediate 10

3-Cyclopropyl-5-(2-methylsulfanyl-pyrimidin-5-yl)-2-(4-trifluoromethoxy-phenyl)-3H-imidazole-4-carboxylic acid sodium salt A) 2-[Cyclopropyl-(4-trifluoromethoxy-benzoyl)-amino]-3-(2-methylsulfanyl-pyrimidin-5-yl)-3-oxo-propionic acid ethyl ester The title compound, a colorless oil (0.7 g, 32%), was prepared in analogy to intermediate 8A by reaction of [cyclopropyl-(4-trifluoromethoxy-benzoyl)-amino]-acetic acid ethyl ester (intermediate 7B) with 2-methylsulfanyl-pyrimidine-5-carboxylic acid (Arukwe, J.; Undheim, K. *Acta Chem. Scand. Ser. B;* 1986; 764-767). MS: 484.2 ($MH^+$).

B) 3-Cyclopropyl-5-(2-methylsulfanyl-pyrimidin-5-yl)-2-(4-trifluoromethoxy-phenyl)-3H-imidazole-4-carboxylic acid ethyl ester The title compound was prepared from 2-[cyclopropyl-(4-trifluoromethoxy-benzoyl)-amino]-3-(2-methylsulfanyl-pyrimidin-5-yl)-3-oxo-propionic acid ethyl ester in direct analogy to intermediate 8B, by reaction with ammonium trifluoroacetate. MS: 465.1 ($MH^+$).

C) 3-Cyclopropyl-5-(2-methylsulfanyl-pyrimidin-5-yl)-2-(4-trifluoromethoxy-phenyl)-3H-imidazole-4-carboxylic acid sodium salt The title compound was prepared from 3-cyclopropyl-5-(2-methylsulfanyl-pyrimidin-5-yl)-2-(4-trifluoromethoxy-phenyl)-3H-imidazole-4-carboxylic acid ethyl ester in analogy to example 8C. MS: 437.1 ($MH^+$).

Intermediate 11

[3-Cyclopropyl-5-(6-dibenzylamino-pyridin-3-yl)-2-(4-trifluoromethoxy-phenyl)-3H-imidazol-4-yl]-(4-pyrrolidin-1-yl-piperidin-1-yl)-methanone A) 2-[Cyclopropyl-(4-trifluoromethoxy-benzoyl)-amino]-3-(6-dibenzylamino-pyridin-3-yl)-3-oxo-propionic acid ethyl ester The title compound, a colorless oil (0.7 g, 32%), was prepared in analogy to intermediate 8A by reaction of [cyclopropyl-(4-trifluoromethoxy-benzoyl)-amino]-acetic acid ethyl ester (intermediate 7B) with 6-dibenzylamino-nicotinic acid (Aminopyridines. *Jpn. Kokai Tokkyo Koho* (1979), JP54041881). MS: 632.3 ($MH^+$).

B) 3-Cyclopropyl-5-(6-dibenzylamino-pyridin-3-yl)-2-(4-trifluoromethoxy-phenyl)-3H-imidazole-4-carboxylic acid ethyl ester The title compound was prepared from 2-[cyclopropyl-(4-trifluoromethoxy-benzoyl)-amino]-3-(6-dibenzylamino-pyridin-3-yl)-3-oxo-propionic acid ethyl ester in direct analogy to intermediate 8B, by reaction with ammonium trifluoroacetate. MS: 613.2 ($MH^+$).

C) 3-Cyclopropyl-5-(6-dibenzylamino-pyridin-3-yl)-2-(4-trifluoromethoxy-phenyl)-3H-imidazole-4-carboxylic acid sodium salt The title compound was prepared from 3-cyclopropyl-5-(6-dibenzylamino-pyridin-3-yl)-2-(4-trifluoromethoxy-phenyl)-3H-imidazole-4-carboxylic acid ethyl ester in analogy to the procedure described for intermediate 8C. MS: 585.2 ($MH^+$).

D) [3-Cyclopropyl-5-(6-dibenzylamino-pyridin-3-yl)-2-(4-trifluoromethoxy-phenyl)-3H-imidazol-4-yl]-(4-pyrrolidin-1-yl-piperidin-1-yl)-methanone To a solution of 0.12 g (0.2 mmol) of 3-cyclopropyl-5-(6-dibenzylamino-pyridin-3-yl)-2-(4-trifluoromethoxy-phenyl)-3H-imidazole-4-carboxylic acid sodium salt and 0.03 g (0.2 mmol) of 4-pyrrolidin-1-yl-piperidine in 1 ml of DMF was added 83 microliters (0.6 mmol) of triethylamine and 0.08 g (0.2 mmol) of HATU. The mixture was stirred for 1 h after which time it was evaporated to dryness, the residue was partitioned between $CH_2Cl_2$ and saturated sodium hydrogen carbonate solution, the organic phase was dried with sodium sulfate and concentrated. Purification by flash column chromatography [MeOH/$CH_2Cl_2$ 5:95] afforded 0.1 g (79%) of the title compound as a colorless solid. MS: 721.3 ($MH^+$).

Intermediate 12

[5-(1-Benzyl-1H-[1,2,4]triazol-3-yl)-3-cyclopropyl-2-(4-trifluoromethoxy-phenyl)-3H-imidazol-4-yl]-(4-pyrrolidin-1-yl-piperidin-1-yl)-methanone A) 1-Benzyl-1H-[1,2,4]triazole-3-carboxylic acid ethyl ester To 1.3 g (10 mmol) of methyl-1H-1,2,4-triazole-3-carboxylate in 15 ml of DMF was added 2.8 g (20 mmol) of potassium carbonate and 1.9 g (11 mmol) of benzyl bromide. The mixture was stirred for 16 h after which time it was filtered and evaporated to dryness. Purification by flash col- B) 1-Benzyl-1H-[1,2,4]triazole-3-carboxylic acid To 1.2 g (6 mmol) of 1-benzyl-1H-[1,2,4]triazole-3-carboxylic acid ethyl ester in 10 ml of EtOH was added 1.4 ml (8 mmol) of 6 M sodium hydroxide solution. The mixture was stirred for 16 h after which time it was concentrated; then, 1 M hydrochloric acid solution was added and the resulting precipitate filtered affording 1.1 g (99%) of the title compound. MS: 204.1 (MH$^+$).

C) 3-(1-Benzyl-1H-[1,2,4]triazol-3-yl)-2-[cyclopropyl-(4-trifluoromethoxy-benzoyl)-amino]-3-oxo-propionic acid ethyl ester The title compound, a colorless oil (1.1 g, 50%), was prepared in analogy to intermediate 8A by reaction of [cyclopropyl-(4-trifluoromethoxy-benzoyl)-amino]-acetic acid ethyl ester (intermediate 7B) with 1-benzyl-1H-[1,2,4]triazole-3-carboxylic acid. MS: 517.2 (MH$^+$).

D) 5-(1-Benzyl-1H-[1,2,4]triazol-3-yl)-3-cyclopropyl-2-(4-trifluoromethoxy-phenyl)-3H-imidazole-4-carboxylic acid ethyl ester The title compound was prepared from 3-(1-benzyl-1H-[1,2,4]triazol-3-yl)-2-[cyclopropyl-(4-trifluoromethoxy-benzoyl)-amino]-3-oxo-propionic acid ethyl ester in direct analogy to intermediate 8B, by reaction with ammonium trifluoroacetate. MS: 498.2 (MH$^+$).

E) 5-(1-Benzyl-1H-[1,2,4]triazol-3-yl)-3-cyclopropyl-2-(4-trifluoromethoxy-phenyl)-3H-imidazole-4-carboxylic acid The title compound was prepared from 5-(1-benzyl-1H-[1,2,4]triazol-3-yl)-3-cyclopropyl-2-(4-trifluoromethoxy-phenyl)-3H-imidazole-4-carboxylic acid ethyl ester in analogy to intermediate 9C. MS: 468.2 (M-H$^-$).

F) [5-(1-Benzyl-1H-[1,2,4]triazol-3-yl)-3-cyclopropyl-2-(4-trifluoromethoxy-phenyl)-3H-imidazol-4-yl]-(4-pyrrolidin-1-yl-piperidin-1-yl)-methanone The title compound was prepared from 5-(1-benzyl-1H-[1,2,4]triazol-3-yl)-3-cyclopropyl-2-(4-trifluoromethoxy-phenyl)-3H-imidazole-4-carboxylic acid in analogy to intermediate 11D. MS: 606.2 (MH$^+$).

Intermediate 13

[5-(1-Benzyl-1H-pyrazol-4-yl)-3-cyclopropyl-2-(4-trifluoromethoxy-phenyl)-3H-imidazol-4-yl]-(4-pyrrolidin-1-yl-piperidin-1-yl)-methanone A) 3-(1-Benzyl-1H-pyrazol-4-yl)-2-[cyclopropyl-(4-trifluoromethoxy-benzoyl)-amino]-3-oxo-propionic acid ethyl ester The title compound, a colorless oil (0.9 g, 41%), was prepared in analogy to intermediate 8A by reaction of [cyclopropyl-(4-trifluoromethoxy-benzoyl)-amino]-acetic acid ethyl ester (intermediate 7B) with 1-benzyl-1H-pyrazole-4-carboxylic acid (Kalla R. V.; Elzein E.; Perry T.; Li X.; Palle V.; Varkhedkar V.; Gimbel A.; Maa T.; Zeng D.; Zablocki J. *Journal of Medicinal Chemistry* (2006), 49(12), 3682-92) .MS: 516.1 (MH$^+$).

B) 5-(1-Benzyl-1H-pyrazol-4-yl)-3-cyclopropyl-2-(4-trifluoromethoxy-phenyl)-3H-imidazole-4-carboxylic acid ethyl ester The title compound was prepared from 3-(1-benzyl-1H-pyrazol-4-yl)-2-[cyclopropyl-(4-trifluoromethoxy-benzoyl)-amino]-3-oxo-propionic acid ethyl ester in direct analogy to intermediate 8B, by reaction with ammonium trifluoroacetate. MS: 497.2 (MH$^+$).

C) 5-(1-Benzyl-1H-pyrazol-4-yl)-3-cyclopropyl-2-(4-trifluoromethoxy-phenyl)-3H-imidazole-4-carboxylic acid The title compound was prepared from 5-(1-benzyl-1H-pyrazol-4-yl)-3-cyclopropyl-2-(4-trifluoromethoxy-phenyl)-3H-imidazole-4-carboxylic acid ethyl ester in analogy to intermediate 9C. MS: 469.1 (MH$^+$).

D) 5-(1-Benzyl-1H-pyrazol-4-yl)-3-cyclopropyl-2-(4-trifluoromethoxy-phenyl)-3H-imidazol-4-yl]-(4-pyrrolidin-1-yl-piperidin-1-yl)-methanone The title compound was prepared from 5-(1-benzyl-1H-pyrazol-4-yl)-3-cyclopropyl-2-(4-trifluoromethoxy-phenyl)-3H-imidazole-4-carboxylic acid in analogy to intermediate 11D. MS: 605.3 (MH$^+$).

Intermediate 14

[5-(1-Benzyl-1H-[1,2,3]triazol-4-yl)-3-cyclopropyl-2-(4-trifluoromethoxy-phenyl)-3H-imidazol-4-yl]-(4-pyrrolidin-1-yl-piperidin-1-yl)-methanone A) 1-Benzyl-1H-[1,2,3]triazole-4-carboxylic acid The title compound was prepared from 1-benzyl-1H-[1,2,3]triazole-4-carboxylic acid methyl ester (Kacprzak, K. *Synlett* (2005), (6), 943-946) in analogy to intermediate 12B. MS: 204.1 (MH$^+$).

B) 3-(1-Benzyl-1H-[1,2,3]triazol-4-yl)-2-[cyclopropyl-(4-trifluoromethoxy-benzoyl)-amino]-3-oxo-propionic acid ethyl ester The title compound, a colorless oil (0.6 g, 27%), was prepared in analogy to intermediate 8A by reaction of [cyclopropyl-(4-trifluoromethoxy-benzoyl)-amino]-acetic acid ethyl ester (intermediate 7B) with 1-benzyl-1H-[1,2,3]triazole-4-carboxylic acid. MS: 517.1 (MH$^+$).

C) 5-(1-Benzyl-1H-[1,2,3]triazol-4-yl)-3-cyclopropyl-2-(4-trifluoromethoxy-phenyl)-3H-imidazole-4-carboxylic acid ethyl ester The title compound was prepared from 3-(1-benzyl-1H-[1,2,3]triazol-4-yl)-2-[cyclopropyl-(4-trifluoromethoxy-benzoyl)-amino]-3-oxo-propionic acid ethyl ester in direct analogy to intermediate 8B, by reaction with ammonium trifluoroacetate. MS: 498.1 (MH⁺).

D) 5-(1-Benzyl-1H-[1,2,3]triazol-4-yl)-3-cyclopropyl-2-(4-trifluoromethoxy-3H-imidazole-4-carboxylic acid The title compound was prepared from 5-(1-benzyl-1H-[1,2,3]triazol-4-yl)-3-cyclopropyl-2-(4-trifluoromethoxy-phenyl)-3H-imidazole-4-carboxylic acid ethyl ester in analogy to intermediate 9C. MS: 470.1 (MH⁺).

E) [5-(1-Benzyl-1H-[1,2,3]triazol-4-yl)-3-cyclopropyl-2-(4-trifluoromethoxy-phenyl)-3H-imidazol-4-yl]-(4-pyrrolidin-1-yl-piperidin-1-yl)-methanone The title compound was prepared from 5-(1-benzyl-1H-[1,2,3]triazol-4-yl)-3-cyclopropyl-2-(4-trifluoromethoxy-phenyl)-3H-imidazole-4-carboxylic acid in analogy to intermediate 11D. MS: 606.2 (MH⁺).

Intermediate 15

3-Cyclopropyl-5-methyl-2-(3-morpholin-4-yl-5-trifluoromethyl-phenyl)-3H-imidazole-4-carboxylic acid A) (tert-Butoxycarbonyl-cyclopropyl-amino)-acetic acid ethyl ester To 5.5 g (38 mmol) of cyclopropylamino-acetic acid ethyl ester (intermediate 7A) in 50 ml of CH₂Cl₂ was added 8.0 g (38 mmol) of Boc anhydride and the mixture was stirred for 1 h. Evaporation of the solvent and purification by filtration through a plug of silica gel (eluent EtOAc/n-heptane 1:1) afforded 8.8 g (94%) of the title compound as a colorless oil. MS: 244.1 (MH⁺).

B) 2-(tert-Butoxycarbonyl-cyclopropyl-amino)-3-oxo-butyric acid ethyl ester

To solution of 63 ml (1 M in THF, 63 mmol) of lithium hexamethyldisilylazide cooled to –78° C. under Ar was added, drop wise, a solution of 7.3 g (30 mmol) of (tert-butoxycarbonyl-cyclopropyl-amino)-acetic acid ethyl ester in 10 ml of THF. The mixture was brought to –40° C. and stirred for 1 h. 2.3 ml (30 mmol) of acetyl chloride was then added and the mixture allowed to reach room temperature over 1 h after which time the reaction was quenched by addition to 10% citric acid solution. The mixture was then extracted with EtOAc, dried with sodium sulfate and concentrated. Purification by flash column chromatography [n-heptane/EtOAc 1:9 to 2:8] afforded 5.8 g (67%) of the title compound as colorless oil, partially contaminated with the starting material. MS: 286.1 (MH⁺).

C) 2-Cyclopropylamino-3-oxo-butyric acid ethyl ester hydrochloride salt

To 6.4 g (23 mmol) of 2-(tert-butoxycarbonyl-cyclopropyl-amino)-3-oxo-butyric acid ethyl ester was added 10 ml of 4M hydrochloric acid in dioxane and the mixture stirred for 2 h. Diethyl ether was then added and 3.5 g (70%) of product was isolated by filtration. MS: 186.0 (MH⁺).

D) 3-Morpholin-4-yl-5-trifluoromethyl-benzoic acid

The title compound was prepared from 3-morpholin-4-yl-5-trifluoromethyl-benzoic acid ethyl ester (Belfield, A. J.; Brown, G. R.; Foubister, A. J.; Ratcliffe, P. D. *Tetrahedron* (1999), 55(46), 13285-13300) in analogy to intermediate 12B. MS: 274.0 (M-H⁻).

E) 3-Cyclopropyl-5-methyl-2-(3-morpholin-4-yl-5-trifluoromethyl-phenyl)-3H-imidazole-4-carboxylic acid ethyl ester To 0.4 g (2 mmol) of 2-cyclopropylamino-3-oxo-butyric acid ethyl ester hydrochloride salt, 0.6 g (2 mmol) of 3-morpholin-4-yl-5-trifluoromethyl-benzoic acid, 0.4 g (2 mmol) of EDCI and 0.3 g (2 mmol) of HOBT was added 2 ml of DMF and 0.6 ml (4 mmol) of triethylamine. The mixture was stirred for 3 h after which time the solvent was removed by evaporation; the residue was then re-dissolved in EtOAc, washed with 10% citric acid solution, saturated sodium hydrogen carbonate solution, dried with sodium sulfate and re-concentrated to afford 0.8 g (93%) of crude 2-[cyclopropyl-(3-morpholin-4-yl-5-trifluoromethyl-benzoyl)-amino]-3-oxo-butyric acid ethyl ester. This material was re-dissolved in 5 ml of EtOH and 1 g (8 mmol) of ammonium trifluoroacetate was added. The solvent was evaporated and the residue heated to 130° C. for 16 h. The cooled residue was partitioned between saturated sodium hydrogen carbonate solution and CH₂Cl₂. The organic phase was dried with sodium sulfate and concentrated. Purification by flash column chromatography [n-heptane/EtOAc 6:4] afforded 0.4 g (55%) of the title compound as colorless solid. MS: 424.2 (MH⁺).

F) 3-Cyclopropyl-5-methyl-2-(3-morpholin-4-yl-5-trifluoromethyl-phenyl)-3H-imidazole-4-carboxylic acid The title compound was prepared from 3-cyclopropyl-5-methyl-2-(3-morpholin-4-yl-5-trifluoromethyl-phenyl)-3H-imidazole-4-carboxylic acid ethyl ester in analogy to intermediate 9C. MS: 396.2 (MH⁺).

Intermediate 16

3-Cyclopropyl-5-furan-2-yl-2-(4-trifluoromethoxy-phenyl)-3H-imidazole-4-carboxylic acid A) 3-Cyclopropyl-5-furan-2-yl-2-(4-trifluoromethoxy-phenyl)-3H-imidazole-4-carbo-xylic acid ethyl ester Under argon, a solution of 1.071 g (3.23 mmol) of [cyclopropyl-(4-trifluoromethoxy-benzoyl)-amino]-acetic acid ethyl ester (intermediate 7B) in 10.0 ml of THF was added drop by drop to 3.5 ml of LiHMDS (solution 1M in THF, 3.5 mmol) cooled to –70° C. The reaction mixture was stirred for 10 min at –70° C. and for 1 hour at –30° C. Then, a solution of 0.167 g (1.28 mmol) of furan-2-carbonyl chloride in 10.0 ml of THF was added drop wise at –30° C. and the reaction mixture was stirred for 1 hour at –30° C. and then allowed to reach RT over 2 hours. The brown solution was partitioned between a sat. NH₄Cl solution and EtOAc. The organic phases were washed with brine and the aqueous phases were extracted with EtOAc. The organic layers were dried over magnesium sulfate, filtered and concentrated in vacuo. The residue was purified by column chromatography (EtOAc/n-heptane 1:1) to give 0.3 g of a 1:2 mixture of [cyclopropyl-(4-trifluoromethoxy-benzoyl)-amino]-acetic acid ethyl ester and 2-[cyclopropyl-(4-trifluoromethoxy-benzoyl)-amino]-3-furan-2-yl-3-oxo-propionic acid ethyl ester. This mixture (0.30 g, max. 0.47 mmol) and 0.368 g (2.81 mmol) of ammoniumtrifluoroacetate were stirred for 10 min in 5 ml EtOH at room temperature; then, the solvent was evaporated and the brown oil was heated at 110° C. over night. The reaction mixture was cooled to RT and partitioned between $CH_2Cl_2$ and sat. $NaHCO_3$ solution, the aqueous phase was extracted with $CH_2Cl_2$. The organic layers were dried over magnesium sulfate, evaporated and chromatographed (silica gel, EtOAc/n-heptane 1:4) to afford 0.098 g (49%) of the title compound as white powder. MS: 407.2 ($MH^+$).

B) 3-Cyclopropyl-5-furan-2-yl-2-(4-trifluoromethoxy-phenyl)-3H-imidazole-4-carboxylic acid A solution of 0.076 g (1.87 mmol) of 3-cyclopropyl-5-furan-2-yl-2-(4-trifluoromethoxy-phenyl)-3H-imidazole-4-carboxylic acid ethyl ester and 0.013 g (5.42 mmol) of LiOH in 4 ml of THF, 2 ml of MeOH and 2 ml of $H_2O$ was stirred at 80° C. for 4.5 hours. The reaction mixture was then cooled to RT, diluted with EtOAc and washed with 10% $KHSO_4$ solution and brine. The aqueous phases were extracted twice with EtOAc. The organic layers were dried over magnesium sulfate, filtered and concentrated in vacuo to give 69 mg (96%) of the title compound as white powder. MS: 377.1 ($MH^+$).

Intermediate 17

5-Methoxy-3-methyl-2-(3-trifluoromethoxy-phenyl)-3H-imidazole-4-carboxylic acid

A) 5-Bromo-3-methyl-2-(3-trifluoromethoxy-phenyl)-3H-imidazole-4-carboxylic acid methyl ester A stirred solution of 1.826 g (5.0 mmol) of 5-bromo-3-methyl-2-(3-trifluoromethoxy-phenyl)-3H-imidazole-4-carboxylic acid (example 72) in 20 ml of DMF was treated at RT with 2.073 g (15.0 mmol) of potassium carbonate, followed by addition of 0.62 ml=1.42 g (10.0 mmol) of iodomethane. After 70 hours, the reaction mixture was poured into crashed ice and extracted twice with $Et_2O$; the organic phases were washed with water, dried over magnesium sulfate, filtered and evaporated. The residue was purified by flash column chromatography (n-heptane/$CH_2Cl_2$ 1:0 to 0:1) to give 1.77 g (93%) of the title compound as light yellow oil. MS: 379.0 ($MH^+$, 1Br).

B) [5-Bromo-3-methyl-2-(3-trifluoromethoxy-phenyl)-3H-imidazol-4-yl]-methanol

A solution of 5.62 ml (5.6 mmol) of lithium aluminium hydride (1 molar in THF) was slowly added to a solution of 3.55 g (9.4 mmol) of 5-bromo-3-methyl-2-(3-trifluoromethoxy-phenyl)-3H-imidazole-4-carboxylic acid methyl ester in 100 ml of THF cooled down to −70° C. The reaction mixture was warmed up to 0° C. and after 30 min cooled down to −50° C. and hydrolyzed with i) EtOAc, ii) $H_2O$ and iii) HCl (1N); after warming up to RT, it was extracted twice with EtOAc; the organic phases were washed with water, dried over magnesium sulfate, filtered and evaporated. The residue was purified by flash column chromatography (n-heptane/EtOAc 9:1 to 1:1) to give 3.25 g (99%) of the title compound as colorless solid. MS: 351.0 ($MH^+$, 1Br).

C) 5-Bromo-3-methyl-2-(3-trifluoromethoxy-phenyl)-3H-imidazole-4-carbaldehyde

A solution of 2.80 g (8.0 mmol) of [5-bromo-3-methyl-2-(3-trifluoromethoxy-phenyl)-3H-imidazol-4-yl]-methanol in 120 ml of EtOAc was treated in small portions with 4.85 g (55.8 mmol) of manganese(IV) oxide; the reaction mixture was stirred at RT for 2 hours and at 50° C. for 5 hours, it was then cooled down to RT and filtered (with the aid of dicalite) and the solvents were evaporated to give 2.813 g (quant.) of the title compound as colorless oil. MS: 349.0 ($MH^+$, 1Br).

D) 5-Methoxy-3-methyl-2-(3-trifluoromethoxy-phenyl)-3H-imidazole-4-carbaldehyde

A solution of 1.00 g (2.9 mmol) of 5-bromo-3-methyl-2-(3-trifluoromethoxy-phenyl)-3H-imidazole-4-carbaldehyde in 25 ml of MeOH was treated with 3.20 ml (17.3 mmol) sodium methoxide-solution (5.4 molar in MeOH) and then stirred at reflux for 48 hours. After cooling down to RT, the solvent was evaporated, cold water and EtOAc were added and the mixture then extracted twice with EtOAc; the organic phases were washed with water, dried over magnesium sulfate, filtered and evaporated. The residue was purified by flash column chromatography (n-heptane/EtOAc 4:1 to 1:1) to give 0.926 g (quant.) of the title compound as light yellow solid. MS: 301.1 ($MH^+$).

E) 5-Methoxy-3-methyl-2-(3-trifluoromethoxy-phenyl)-3H-imidazole-4-carboxylic acid methyl ester A stirred solution of 0.300 g (1.0 mmol) of 5-methoxy-3-methyl-2-(3-trifluoromethoxy-phenyl)-3H-imidazole-4-carbaldehyde in 40 ml of MeOH was treated with 0.25 g (5.0 mmol) of sodium cyanide and 0.09 ml=0.096 g (1.6 mmol) of AcOH followed by 2.03 g (21 mmol) of manganese(IV) oxide. The reaction mixture was stirred at reflux for 8 hours, then cooled down to RT and filtered; the solvents were removed by evaporation and cold water and EtOAc were added to the residue. The mixture was extracted twice with EtOAc; the organic phases were washed with water, dried over magnesium sulfate, filtered and evaporated. The residue was purified by flash column chromatography (n-heptane/EtOAc 9:1 to 4:1) to give 0.29 g of an about 1:1 mixture of 5-methoxy-3-methyl-2-(3-trifluoromethoxy-phenyl)-3H-imidazole-4-carbaldehyde and 5-methoxy-3-methyl-2-(3-trifluoromethoxy-phenyl)-3H-imidazole-4-carboxylic acid methyl ester [MS: 331.3 ($MH^+$)].

F) 5-Methoxy-3-methyl-2-(3-trifluoromethoxy-phenyl)-3H-imidazole-4-carboxylic acid A stirred solution of 0.27 g of a mixture of 5-methoxy-3-methyl-2-(3-trifluoromethoxy-phenyl)-3H-imidazole-4-carbaldehyde and 5-methoxy-3-methyl-2-(3-trifluoromethoxy-phenyl)-3H-imidazole-4-carboxylic acid methyl ester (ca. 1:1) in 10 ml of THF/MeOH 1:1 was treated with 0.49 ml (0.5 mmol) of a LiOH solution (1.0 molar in $H_2O$) and the mixture was stirred for 34 days at RT. It was then poured into crashed ice, acidified with HCl (1.0 N) and extracted twice with $MeCl_2$; the organic phases were washed with water, dried over magnesium sulfate, filtered and evaporated. The residue was purified by flash column chromatography ($CH_2Cl_2$/

MeOH 1:0 to 4:1) to give 0.056 g (ca. 22% over two steps) of the title compound, which has been used without further characterization.

Example 1

(rac)-(3-Diethylamino-pyrrolidin-1-yl)-[2-(3-hexyl-phenyl)-5-iodo-3-methyl-3H-imidazol-4-yl]-methanone

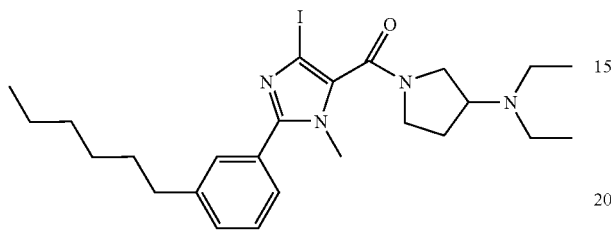

A solution of 0.41 g (1.0 mmol) of 2-(3-hexyl-phenyl)-5-iodo-3-methyl-3H-imidazol-4-carboxylic acid (intermediate 1) in 10 ml of MeCN was treated with 0.192 g (1.1 mmol) of 2-chloro-4,6-dimethoxy-[1,3,5]triazine and cooled down to 0° C. 0.33 ml=0.30 g (3.0 mmol) of N-methylmorpholine was added and stirring continued at 0° C. for another 2 hours. Then, a solution of 0.159 g (1.1 mmol) of (rac)-diethyl-pyrrolidin-3-yl-amine in 5 ml of MeCN was added and the reaction mixture was allowed the reach RT. After stirring at RT for 18 hours, it was poured into crashed ice and extracted twice with EtOAc; the organic phases were washed with water, dried over magnesium sulfate, filtered and evaporated. The residue was purified by flash column chromatography ($CH_2Cl_2$/MeOH 1:0 to 4:1) to give 0.39 g (73%) of the title compound as light brown oil. MS: 537.3 ($MH^+$).

Example 2

[2-(3-Hexyl-phenyl)-5-iodo-3-methyl-3H-imidazol-4-yl]-(4-pyrrolidin-1-yl-piperidin-1-yl)-methanone

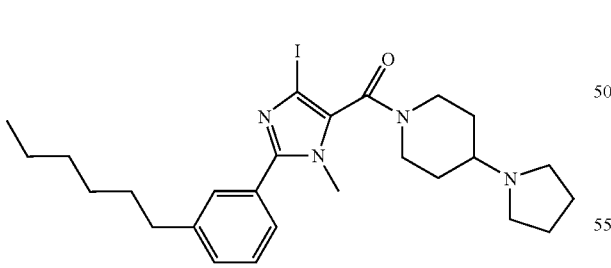

7.20 g (17.5 mmol) of 2-(3-hexyl-phenyl)-5-iodo-3-methyl-3H-imidazole-4-carboxylic acid (intermediate 1) were dissolved in 290 ml of DMF and treated with 6.846 g (17.5 mmol) of HATU. 7.30 ml=5.30 g (52.4 mmol) of $Et_3N$ were added and after 30 min, a solution of 2.72 g (17.5 mmol) of 4-pyrrolidin-1-yl-piperidine in 70 ml of DMF was added. After 16 hours, the reaction mixture was poured into crashed ice and extracted three times with $Et_2O$; the organic phases were washed with water, dried over magnesium sulfate, filtered and evaporated. The residue was purified by flash column chromatography ($CH_2Cl_2$/MeOH 1:0 to 9:1) to give 8.65 g (90%) of the title compound as light brown foam. MS: 549.3 ($MH^+$).

Example 3

[2-(3-Hexyl-phenyl)-5-iodo-3-methyl-3H-imidazol-4-yl]-[4-(2-hydroxy-ethyl)-[1,4]diazepan-1-yl]-methanone

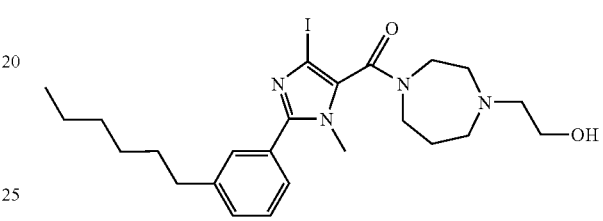

In analogy to the procedure described for example 1, 2-(3-hexyl-phenyl)-5-iodo-3-methyl-3H-imidazole-4-carboxylic acid (intermediate 1) and 2-[1,4]diazepan-1-yl-ethanol gave the title compound as light yellow oil. MS: 539.3 ($MH^+$).

Example 4

(rac)-(3-Diethylamino-pyrrolidin-1-yl)-[2-(3-hexyl-phenyl)-3-methyl-3H-imidazol-4-yl]-methanone

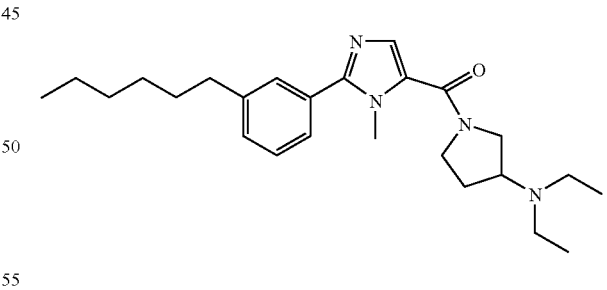

A solution of 0.230 g (0.43 mmol) of (rac)-(3-diethylamino-pyrrolidin-1-yl)-[2-(3-hexyl-phenyl)-5-iodo-3-methyl-3H-imidazol-4-yl]-methanone (example 1) in 10 ml of MeOH was treated with 0.091 g (0.1 mmol) of Pd—C (10%) and the reaction mixture was then hydrogenated with $H_2$ (1 bar) at RT for 2 hours. After removal the catalyst by filtration, the solvent was evaporated completely to give 0.17 g (96%) of the title compound as light yellow oil. MS: 411.2 ($MH^+$).

Example 5

[2-(3-Hexyl-phenyl)-3-methyl-3H-imidazol-4-yl]-(4-pyrrolidin-1-yl-piperidin-1-yl)-methanone

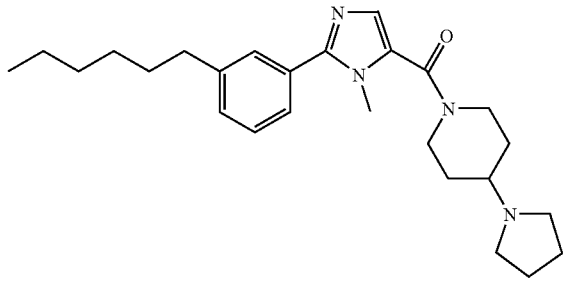

In analogy to the procedure described for example 4, [2-(3-hexyl-phenyl)-5-iodo-3-methyl-3H-imidazol-4-yl]-(4-pyrrolidin-1-yl-piperidin-1-yl)-methanone (example 2) was hydrogenated to give the title compound as light yellow gum. MS: 423.4 (MH$^+$).

Example 6

[2-(3-Hexyl-phenyl)-3-methyl-3H-imidazol-4-yl]-[4-(2-hydroxy-ethyl)-[1,4]diazepan-1-yl]-methanone

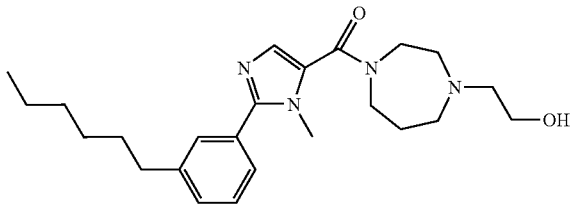

In analogy to the procedure described for example 4, [2-(3-hexyl-phenyl)-5-iodo-3-methyl-3H-imidazol-4-yl]-[4-(2-hydroxy-ethyl)-[1,4]diazepan-1-yl]-methanone (example 3) was hydrogenated to give the title compound as light brown gum. MS: 413.4 (MH$^+$).

Example 7

[5-(4-Fluoro-phenyl)-2-(3-hexyl-phenyl)-3-methyl-3H-imidazol-4-yl]-(4-pyrrolidin-1-yl-piperidin-1-yl)-methanone

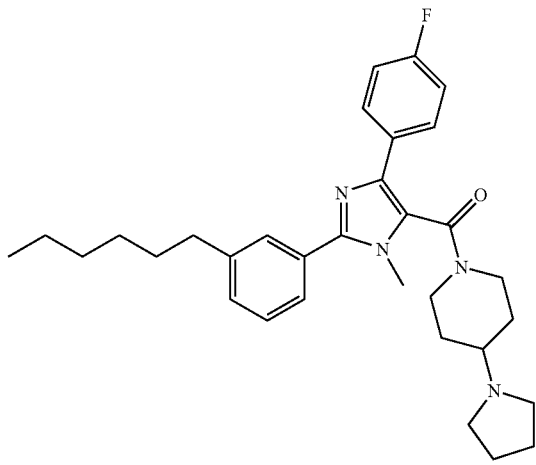

To a solution of 0.275 g (0.50 mmol) of [2-(3-hexyl-phenyl)-5-iodo-3-methyl-3H-imidazol-4-yl]-(4-pyrrolidin-1-yl-piperidin-1-yl)-methanone (example 2) and 0.140 g (1.0 mmol) of 4-fluorophenyl boronic acid in 10 ml of DMF was added drop by drop 2.50 ml of tribasic potassium phosphate (2 M in water), followed by 0.029 g (0.025 mmol) of tetrakis-(triphenylphosphine)-palladium. This reaction mixture was stirred at 80° C. for two hours and subsequently cooled down to RT, then poured into crashed ice and extracted three times with CH$_2$Cl$_2$; the organic phases were washed with water, dried over magnesium sulfate, filtered and evaporated. The residue was purified by flash column chromatography (CH$_2$Cl$_2$/MeOH 1:0 to 9:1) to give 0.20 g (76%) of the title compound as light yellow oil. MS: 517.4 (MH$^+$).

Example 8

[2-(3-Hexyl-phenyl)-3-methyl-5-pyridin-3-yl-3H-imidazol-4-yl]-(4-pyrrolidin-1-yl-piperidin-1-yl)-methanone

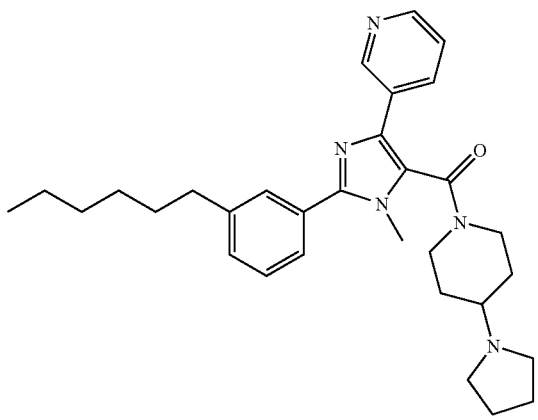

In analogy to the procedure described for example 7, [2-(3-hexyl-phenyl)-5-iodo-3-methyl-3H-imidazol-4-yl]-(4-pyrrolidin-1-yl-piperidin-1-yl)-methanone (example 2) was reacted with pyridin-3-yl-boronic acid to give the title compound as light yellow oil. MS: 500.3 (MH$^+$).

Example 9

[2-(3-Hexyl-phenyl)-3-methyl-5-pyridin-4-yl-3H-imidazol-4-yl]-(4-pyrrolidin-1-yl-piperidin-1-yl)-methanone

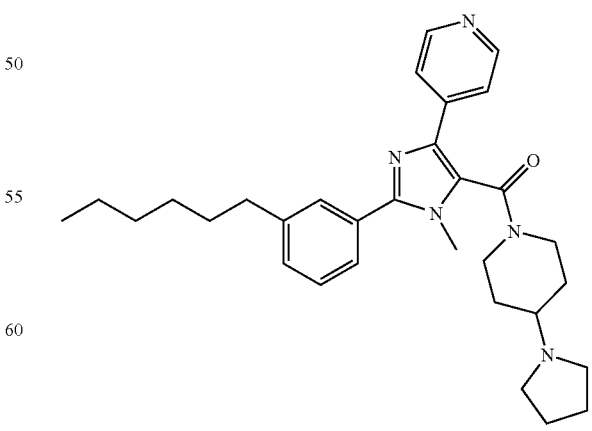

In analogy to the procedure described for example 7, [2-(3-hexyl-phenyl)-5-iodo-3-methyl-3H-imidazol-4-yl]-(4-pyrrolidin-1-yl-piperidin-1-yl)-methanone (example 2) was reacted with pyridin-4-yl-boronic acid to give the title compound as light yellow oil. MS: 500.3 (MH⁺).

Example 10

4-[2-(3-Hexyl-phenyl)-1-methyl-5-(4-pyrrolidin-1-yl-piperidine-1-carbonyl)-1H-imidazol-4-yl]-benzoic acid methyl ester

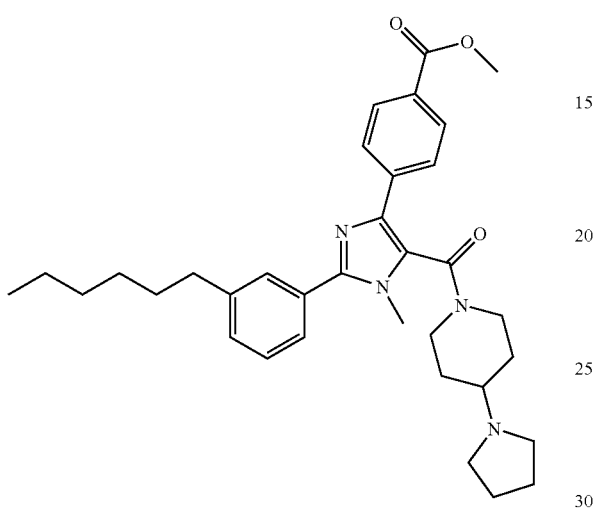

In analogy to the procedure described for example 7, [2-(3-hexyl-phenyl)-5-iodo-3-methyl-3H-imidazol-4-yl]-(4-pyrrolidin-1-yl-piperidin-1-yl)-methanone (example 2) was reacted with (4-methoxycarbonylphenyl)boronic acid to give the title compound as light brown oil. MS: 557.3 (MH⁺).

Example 11

4-[2-(3-Hexyl-phenyl)-1-methyl-5-(4-pyrrolidin-1-yl-piperidine-1-carbonyl)-1H-imidazol-4-yl]-benzoic acid

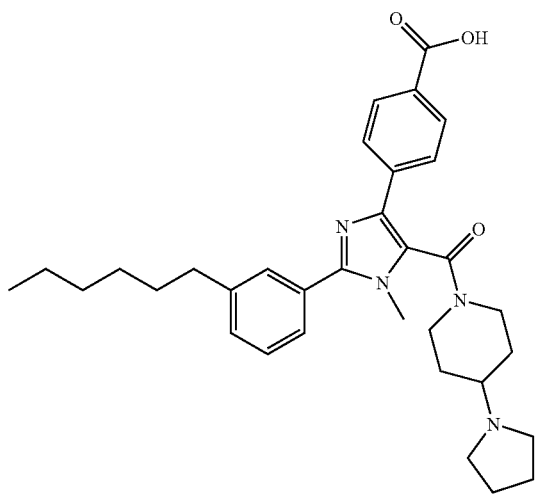

To a solution of 0.15 g (0.27 mmol) of 4-[2-(3-hexyl-phenyl)-1-methyl-5-(4-pyrrolidin-1-yl-piperidine-1-carbonyl)-1H-imidazol-4-yl]-benzoic acid methyl ester (example 10) in 10 ml of THF/MeOH 1:1 was added drop by drop 0.67 ml (0.67 mmol) of lithium hydroxide solution (1 molar in water) and the reaction mixture was heated up to 50° C. After 10 hours, the solvents were evaporated and the residue poured into crashed ice, acidified with HCl (25% in water) and extracted twice with CH₂Cl₂/2-propanol 4:1; the organic phases were dried over magnesium sulfate, filtered and evaporated. The residue was purified by flash column chromatography (CH₂Cl₂/MeOH 1:0 to 9:1) to give 0.13 g (89%) of the title compound as light brown solid. MS: 541.2 ([M-H]⁻).

Example 12

[2-(3-Hexyl-phenyl)-3-methyl-5-trimethylsilanyl-ethynyl-3H-imidazol-4-yl]-(4-pyrrolidin-1-yl-piperidin-1-yl)-methanone

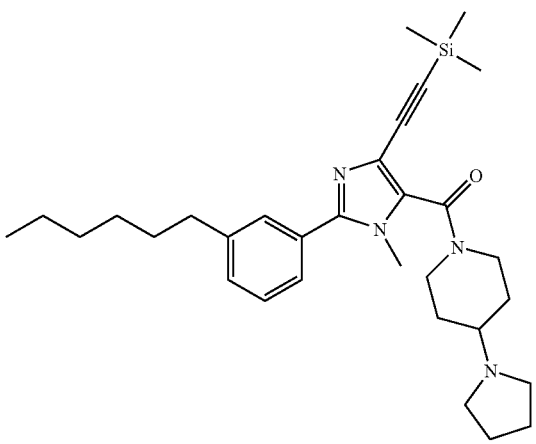

To a suspension of 0.55 g (1.00 mmol) of [2-(3-hexyl-phenyl)-5-iodo-3-methyl-3H-imidazol-4-yl]-(4-pyrrolidin-1-yl-piperidin-1-yl)-methanone (example 2), 0.057 g (0.3 mmol) of copper(I) iodide, 0.117 g (0.1 mmol) of tetrakis-(triphenylphosphine)-palladium and 1.134 g (3.00 mmol) of tetrabutylammoniumiodide in 10 ml of DMF were added 2.027 ml=1.471 g (14.5 mmol) of Et₃N. After stirring at RT for 30 min, 0.57 ml=0.394 g (4.0 mmol) of trimethylsilylacetylene were added and the reaction was heated up to 70° C. for 1 hour and subsequently cooled down to RT. The reaction mixture was then poured into crashed ice and extracted twice with EtOAc; the organic phases were washed with water, dried over magnesium sulfate, filtered and evaporated. The residue was purified by flash column chromatography (CH$_2$Cl$_2$/MeOH 1:0 to 9:1) to give 0.52 (100%) of the title compound as brown oil. MS: 519.4 (MH$^+$).

Example 13

[5-Ethynyl-2-(3-hexyl-phenyl)-3-methyl-3H-imidazol-4-yl]-(4-pyrrolidin-1-yl-piperidin-1-yl)-methanone

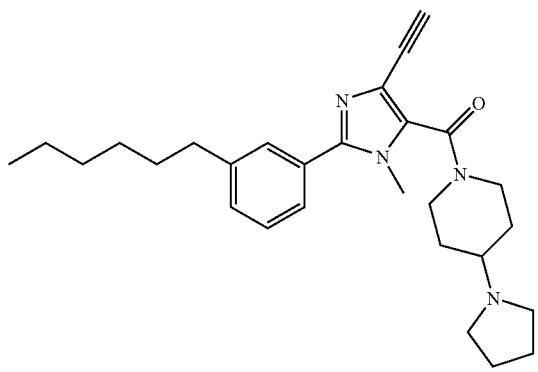

To a solution of 0.52 g (1.00 mmol) of [2-(3-hexyl-phenyl)-3-methyl-5-trimethylsilanylethynyl-3H-imidazol-4-yl]-(4-pyrrolidin-1-yl-piperidin-1-yl)-methanone (example 12) in 10 ml EtOH:THF 5:1 was added 0.277 g (2.0 mmol) of solid potassium carbonate and the reaction mixture was stirred at RT for 18 hours. It was then poured into crashed ice, acidified with HCl (25% in water) and extracted twice with CH$_2$Cl$_2$; the organic phases were washed with water, dried over magnesium sulfate, filtered and evaporated. The residue was purified by flash column chromatography (CH$_2$Cl$_2$/MeOH 1:0 to 9:1) to give 0.27 g (60%) of the title compound as light brown solid. MS: 447.4 (MH$^+$).

Example 14

[5-Ethyl-2-(3-hexyl-phenyl)-3-methyl-3H-imidazol-4-yl]-(4-pyrrolidin-1-yl-piperidin-1-yl)-methanone

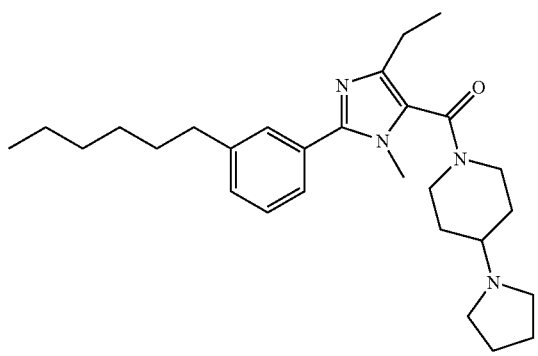

A solution of 0.13 g (0.29 mmol) of [5-ethynyl-2-(3-hexyl-phenyl)-3-methyl-3H-imidazol-4-yl]-(4-pyrrolidin-1-yl-piperidin-1-yl)-methanone (example 13) in 5 ml of MeOH was treated with 0.031 g (0.03 mmol) of Pd—C (10%) and the reaction mixture was then hydrogenated with H$_2$ (1 bar) at RT for 2 hours. After removal the catalyst by filtration, the solvent was evaporated. The residue was purified by flash column chromatography (CH$_2$Cl$_2$/MeOH 1:0 to 4:1) to give 0.12 g (92%) of the title compound as light yellow oil. MS: 451.1 (MH$^+$).

Example 15

[5-Cyclopropyl-2-(3-hexyl-phenyl)-3-methyl-3H-imidazol-4-yl]-(4-pyrrolidin-1-yl-piperidin-1-yl)-methanone

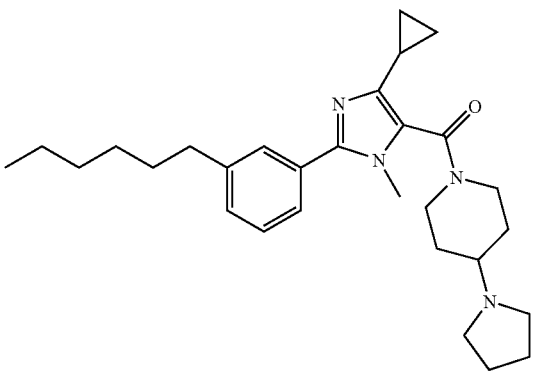

A suspension of 0.275 g (0.50 mmol) of [2-(3-hexyl-phenyl)-5-iodo-3-methyl-3H-imidazol-4-yl]-(4-pyrrolidin-1-yl-piperidin-1-yl)-methanone (example 2), 0.086 g (1.0 mmol) of cyclopropyl boronic acid and 0.573 g (2.7 mmol) of tribasic potassium phosphate in 10 ml of toluene was treated with 0.30 ml of water, followed by 0.031 g (0.11 mmol) of tricyclohexylphosphine and 0.012 g (0.055 mmol) of palladium (II)acetate. This reaction mixture was heated up to 100° C., stirred for 18 hours at this temperature and subsequently cooled down to RT. The reaction mixture was then poured into crashed ice and extracted twice with EtOAc; the organic phases were washed with water, dried over magnesium sulfate, filtered and evaporated. The residue was purified by flash column chromatography (CH$_2$Cl$_2$/MeOH 1:0 to 4:1) to give 0.077 g (33%) of the title compound as light yellow oil. MS: 463.4 (MH$^+$).

Example 16

[2-(3-Hexyl-phenyl)-3-methyl-5-pyrimidin-5-yl-3H-imidazol-4-yl]-(4-pyrrolidin-1-yl-piperidin-1-yl)-methanone

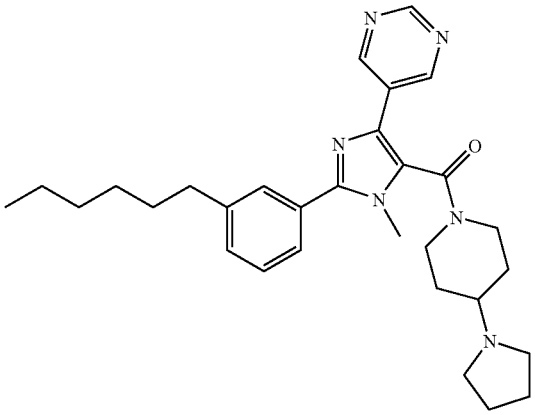

In analogy to the procedure described for example 7, [2-(3-hexyl-phenyl)-5-iodo-3-methyl-3H-imidazol-4-yl]-(4-pyrrolidin-1-yl-piperidin-1-yl)-methanone (example 2) was

Example 17

[2-(3-Hexyl-phenyl)-3-methyl-5-pyridin-2-yl-3H-imidazol-4-yl]-(4-pyrrolidin-1-yl-piperidin-1-yl)-methanone

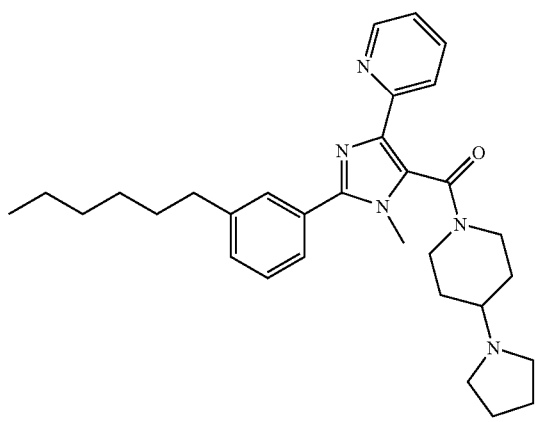

In analogy to the procedure described for example 7, [2-(3-hexyl-phenyl)-5-iodo-3-methyl-3H-imidazol-4-yl]-(4-pyrrolidin-1-yl-piperidin-1-yl)-methanone (example 2) was reacted with pyridin-2-yl-boronic acid to give the title compound as yellow solid. MS: 500.0 (MH$^+$).

Example 18

2-(3-Hexyl-phenyl)-1-methyl-5-(4-pyrrolidin-1-yl-piperidine-1-carbonyl)-1H-imidazole-4-carbonitrile

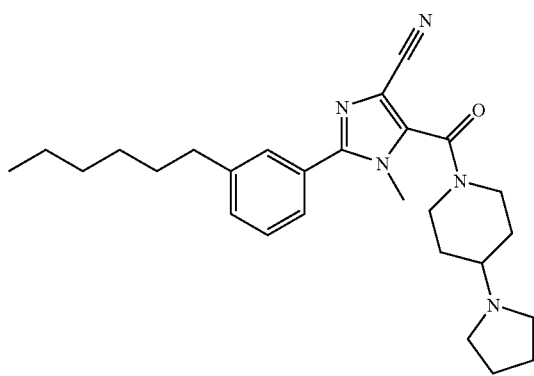

A solution of 0.275 g (0.50 mmol) of [2-(3-hexyl-phenyl)-5-iodo-3-methyl-3H-imidazol-4-yl]-(4-pyrrolidin-1-yl-piperidin-1-yl)-methanone (example 2) in 10 ml of DMF was treated with 0.118 g (1.0 mmol) of zinc cyanide and 0.058 g (0.05 mmol) of tetrakis-(triphenylphosphine)-palladium. This reaction mixture was heated up to 150° C., stirred for 8 hours at this temperature and subsequently cooled down to RT. Then, it was poured into crashed ice and extracted three times with CH$_2$Cl$_2$; the organic phases were washed with water, dried over magnesium sulfate, filtered and evaporated. The residue was purified by flash column chromatography (CH$_2$Cl$_2$/MeOH 1:0 to 9:1) to give 0.18 g (81%) of the title compound as light yellow oil. MS: 448.2 (MH$^+$).

Example 19

[5-Iodo-3-methyl-2-(3-trifluoromethoxy-phenyl)-3H-imidazol-4-yl]-(4-pyrrolidin-1-yl-piperidin-1-yl)-methanone

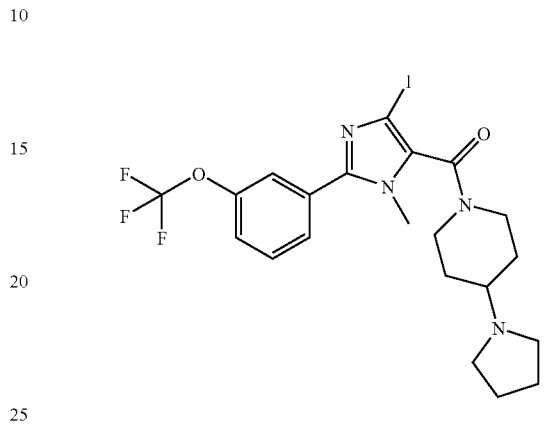

In analogy to the procedures described for intermediates 1B, 1D-F and to the procedure described for example 2, the title compound has been obtained by i) transformation of 3-trifluoromethoxy-benzaldehyde into 2-(3-trifluoromethoxy-phenyl)-1H-imidazole; ii) iodination of 2-(3-trifluoromethoxy-phenyl)-1H-imidazole to give 4,5-diiodo-2-(3-trifluoromethoxy-phenyl)-1H-imidazole; iii) methylation of 4,5-diiodo-2-(3-trifluoromethoxy-phenyl)-1H-imidazole to give 4,5-diiodo-1-methyl-2-(3-trifluoromethoxy-phenyl)-1H-imidazole; iv) carboxylation of 4,5-diiodo-1-methyl-2-(3-trifluoromethoxy-phenyl)-1H-imidazole to give 5-iodo-3-methyl-2-(3-trifluoromethoxy-phenyl)-3H-imidazole-4-carboxylic acid; v) coupling of 5-iodo-3-methyl-2-(3-trifluoromethoxy-phenyl)-3H-imidazole-4-carboxylic acid with 4-pyrrolidin-1-yl-piperidine to give the title compound as light yellow foam. MS: 549.1 (MH$^+$).

Example 20

[3-Methyl-2-(3-trifluoromethoxy-phenyl)-3H-imidazol-4-yl]-(4-pyrrolidin-1-yl-piperidin-1-yl)-methanone

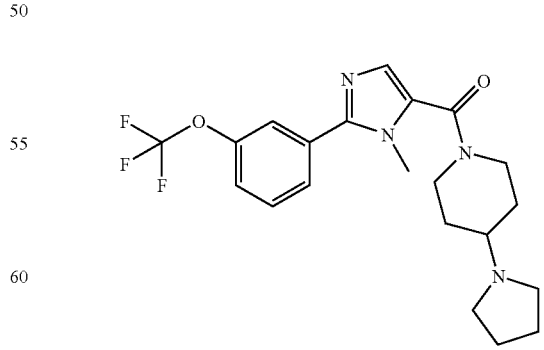

In analogy to the procedure described for example 4, [5-iodo-3-methyl-2-(3-trifluoromethoxy-phenyl)-3H-imidazol-4-yl]-(4-pyrrolidin-1-yl-piperidin-1-yl)-methanone (example 19) was hydrogenated to give the title compound as off-white foam. MS: 423.2 (MH+).

Example 21

[3-Methyl-5-pyridin-3-yl-2-(3-trifluoromethoxy-phenyl)-3H-imidazol-4-yl]-(4-pyrrolidin-1-yl-piperidin-1-yl)-methanone

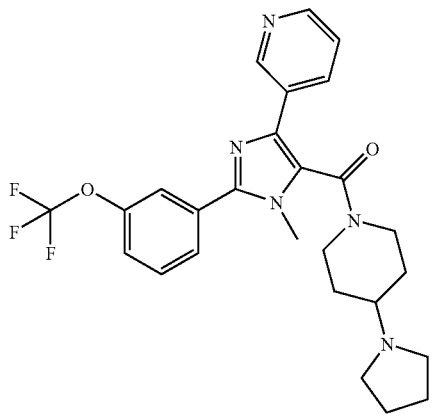

In analogy to the procedure described for example 7, [5-iodo-3-methyl-2-(3-trifluoromethoxy-phenyl)-3H-imidazol-4-yl]-(4-pyrrolidin-1-yl-piperidin-1-yl)-methanone (example 19) was reacted with pyridine-3-yl-boronic acid to give the title compound as colorless foam. MS: 500.1 (MH+).

Example 22

[3-Methyl-5-pyrimidin-5-yl-2-(3-trifluoromethoxy-phenyl)-3H-imidazol-4-yl]-(4-pyrrolidin-1-yl-piperidin-1-yl)-methanone

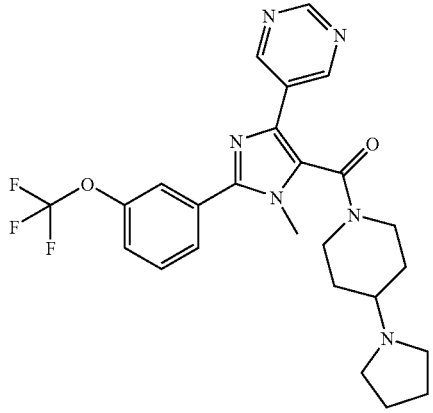

In analogy to the procedure described for example 7, [5-iodo-3-methyl-2-(3-trifluoromethoxy-phenyl)-3H-imidazol-4-yl]-(4-pyrrolidin-1-yl-piperidin-1-yl)-methanone (example 19) was reacted with pyrimidine-5-yl-boronic acid to give the title compound as colorless foam. MS: 501.1 (MH+).

Example 23

[3-Methyl-2-(3-trifluoromethoxy-phenyl)-5-trimethylsilanylethynyl-3H-imidazol-4-yl]-(4-pyrrolidin-1-yl-piperidin-1-yl)-methanone

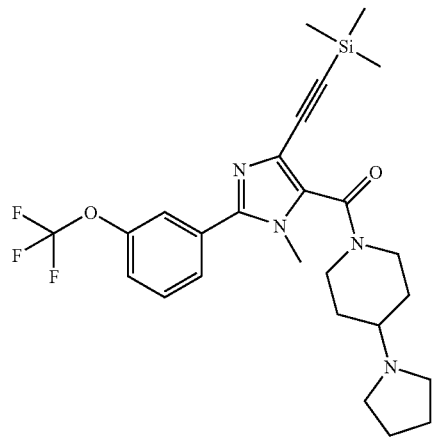

In analogy to the procedure described for example 12, [5-iodo-3-methyl-2-(3-trifluoromethoxy-phenyl)-3H-imidazol-4-yl]-(4-pyrrolidin-1-yl-piperidin-1-yl)-methanone (example 19) was reacted with trimethylsilylacetylene to give the title compound as dark brown gum. MS: 519.2 (MH+).

Example 24

[5-Ethynyl-3-methyl-2-(3-trifluoromethoxy-phenyl)-3H-imidazol-4-yl]-(4-pyrrolidin-1-yl-piperidin-1-yl)-methanone

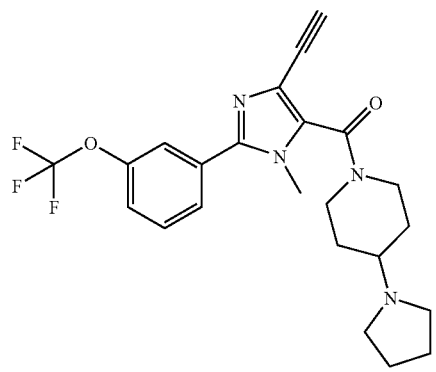

In analogy to the procedure described for example 13, [3-methyl-2-(3-trifluoromethoxy-phenyl)-5-trimethylsilanylethynyl-3H-imidazol-4-yl]-(4-pyrrolidin-1-yl-piperidin- 1-yl)-methanone (example 23) was reacted with potassium carbonate to give the title compound as colorless foam. MS: 447.2 (MH⁺).

Example 25

[5-Ethyl-3-methyl-2-(3-trifluoromethoxy-phenyl)-3H-imidazol-4-yl]-(4-pyrrolidin-1-yl-piperidin-1-yl)-methanone

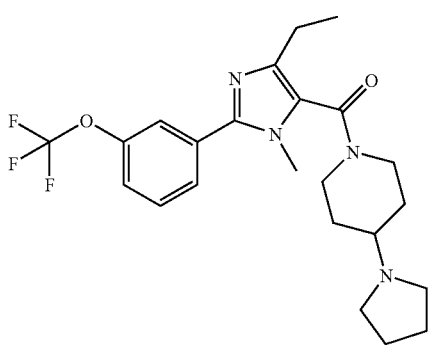

In analogy to the procedure described for example 14, [5-ethynyl-3-methyl-2-(3-trifluoromethoxy-phenyl)-3H-imidazol-4-yl]-(4-pyrrolidin-1-yl-piperidin-1-yl)-methanone (example 24) was hydrogenated to give the title compound as light yellow foam. MS: 451.2 (MH⁺).

Example 26

[5-(6-Chloro-pyridin-3-yl)-2-(3-hexyl-phenyl)-3-methyl-3H-imidazol-4-yl]-(4-pyrrolidin-1-yl-piperidin-1-yl)-methanone

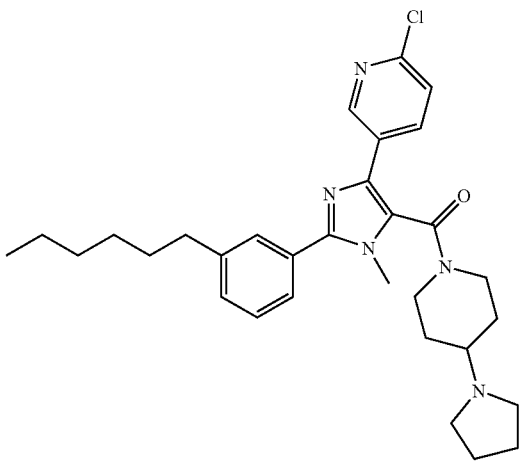

In analogy to the procedure described for example 7, [2-(3-hexyl-phenyl)-5-iodo-3-methyl-3H-imidazol-4-yl]-(4-pyrrolidin-1-yl-piperidin-1-yl)-methanone (example 2) was reacted with 6-chloro-pyridin-3-yl-boronic acid to give the title compound as light yellow gum. MS: 534.3 (MH⁺, 1Cl).

Example 27

[2-(3-Hexyl-phenyl)-5-(2-methoxy-pyridin-4-yl)-3-methyl-3H-imidazol-4-yl]-(4-pyrrolidin-1-yl-piperidin-1-yl)-methanone

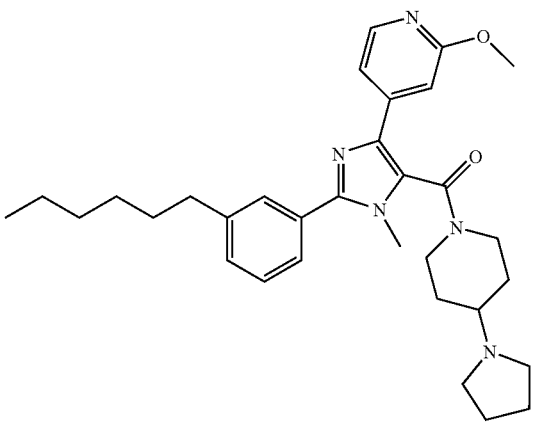

In analogy to the procedure described for example 7, [2-(3-hexyl-phenyl)-5-iodo-3-methyl-3H-imidazol-4-yl]-(4-pyrrolidin-1-yl-piperidin-1-yl)-methanone (example 2) was reacted with 2-methoxy-pyridin-4-yl-boronic acid to give the title compound as light yellow gum. MS: 530.3 (MH⁺).

Example 28

[5-(2-Chloro-pyridin-4-yl)-2-(3-hexyl-phenyl)-3-methyl-3H-imidazol-4-yl]-(4-pyrrolidin-1-yl-piperidin-1-yl)-methanone

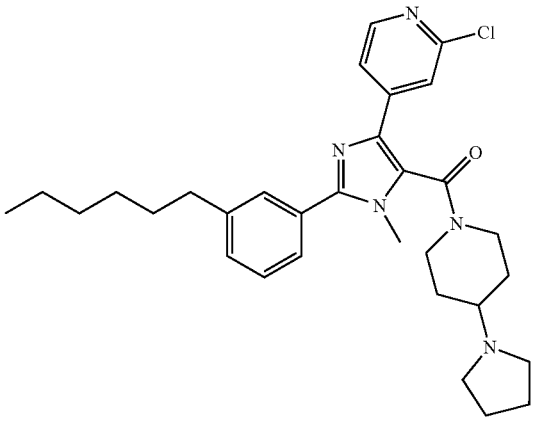

In analogy to the procedure described for example 7, [2-(3-hexyl-phenyl)-5-iodo-3-methyl-3H-imidazol-4-yl]-(4-pyrrolidin-1-yl-piperidin-1-yl)-methanone (example 2) was reacted with 2-chloro-pyridin-4-yl-boronic acid to give the title compound as light yellow gum. MS: 534.3 (MH+, 1Cl).

Example 29

[2-(3-Hexyl-phenyl)-5-(6-methoxy-pyridin-3-yl)-3-methyl-3H-imidazol-4-yl]-(4-pyrrolidin-1-yl-piperidin-1-yl)-methanone

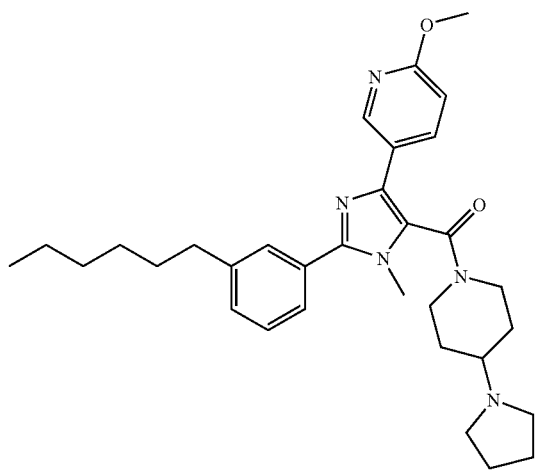

In analogy to the procedure described for example 7, [2-(3-hexyl-phenyl)-5-iodo-3-methyl-3H-imidazol-4-yl]-(4-pyrrolidin-1-yl-piperidin-1-yl)-methanone (example 2) was reacted with 6-methoxy-pyridin-3-yl-boronic acid to give the title compound as light yellow oil. MS: 530.3 (MH+).

Example 30

[2-(3-Hexyl-phenyl)-5-(2-methoxy-pyrimidin-5-yl)-3-methyl-3H-imidazol-4-yl]-(4-pyrrolidin-1-yl-piperidin-1-yl)-methanone

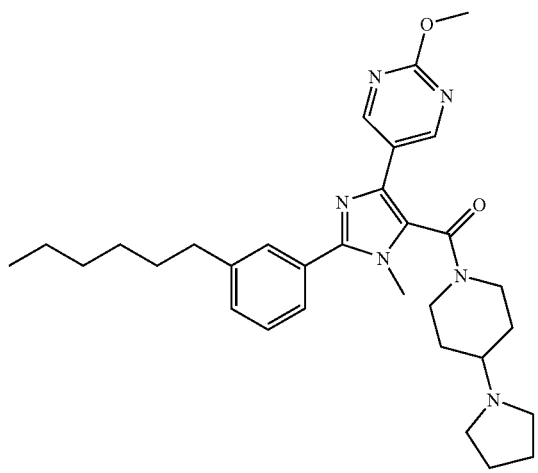

In analogy to the procedure described for example 7, [2-(3-hexyl-phenyl)-5-iodo-3-methyl-3H-imidazol-4-yl]-(4-pyrrolidin-1-yl-piperidin-1-yl)-methanone (example 2) was reacted with 2-methoxy-pyrimidin-5-yl-boronic acid to give the title compound as yellow oil. MS: 531.5 (MH+).

Example 31

[2-(3-Hexyl-phenyl)-5-(3-hydroxy-prop-1-ynyl)-3-methyl-3H-imidazol-4-yl]-(4-pyrrolidin-1-yl-piperidin-1-yl)-methanone

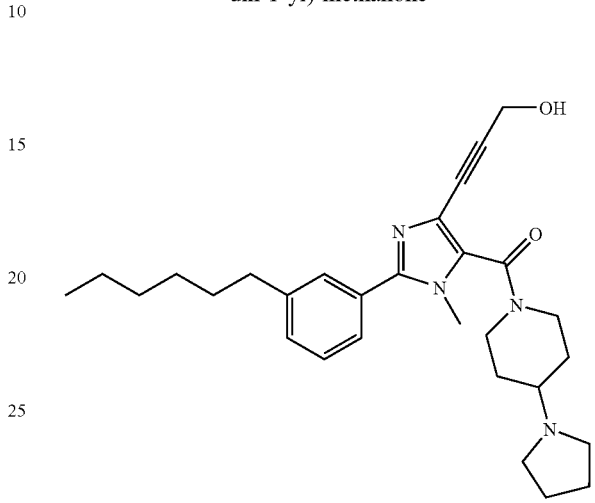

In analogy to the procedure described for example 12, [2-(3-hexyl-phenyl)-5-iodo-3-methyl-3H-imidazol-4-yl]-(4-pyrrolidin-1-yl-piperidin-1-yl)-methanone (example 2) was reacted with prop-2-yn-1-ol to give the title compound as light brown oil. MS: 477.3 (MH+).

Example 32

[2-(3-Hexyl-phenyl)-5-(3-methoxy-prop-1-ynyl)-3-methyl-3H-imidazol-4-yl]-(4-pyrrolidin-1-yl-piperidin-1-yl)-methanone

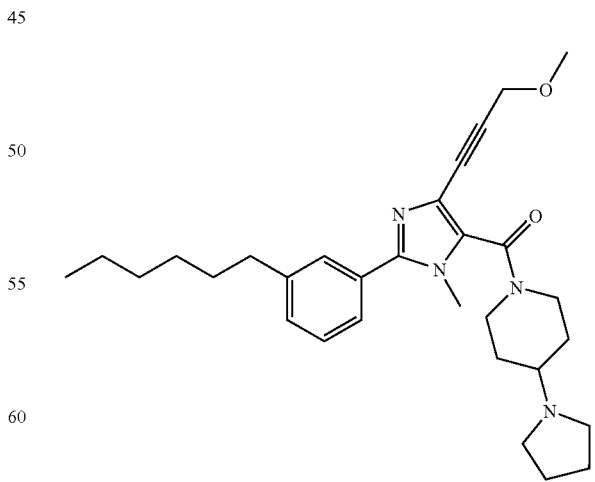

In analogy to the procedure described for example 12, [2-(3-hexyl-phenyl)-5-iodo-3-methyl-3H-imidazol-4-yl]-(4-pyrrolidin-1-yl-piperidin-1-yl)-methanone (example 2) was reacted with 3-methoxy-propyne to give the title compound as yellow oil. MS: 491.4 (MH+).

Example 33

[2-(3-Hexyl-phenyl)-5-(3-hydroxy-propyl)-3-methyl-3H-imidazol-4-yl]-(4-pyrrolidin-1-yl-piperidin-1-yl)-methanone

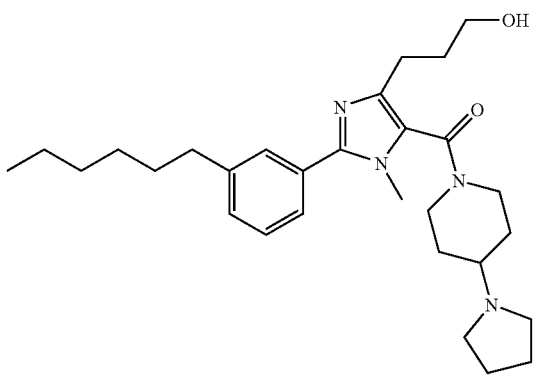

In analogy to the procedure described for example 14, [2-(3-hexyl-phenyl)-5-(3-hydroxy-prop-1-ynyl)-3-methyl-3H-imidazol-4-yl]-(4-pyrrolidin-1-yl-piperidin-1-yl)-methanone (example 31) was hydrogenated using platinum oxide as catalyst to give the title compound as yellow oil. MS: 481.4 (MH+).

Example 34

[2-(3-Hexyl-phenyl)-5-(3-methoxy-propyl)-3-methyl-3H-imidazol-4-yl]-(4-pyrrolidin-1-yl-piperidin-1-yl)-methanone

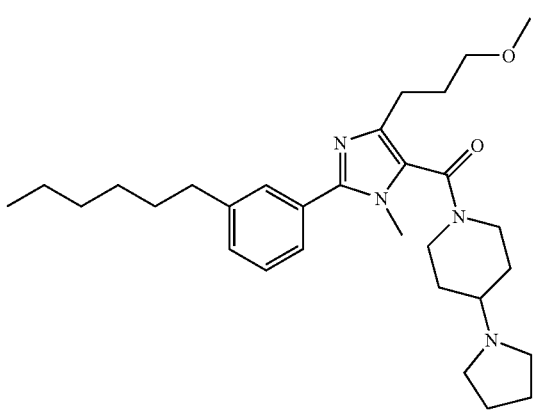

In analogy to the procedure described for example 14, [2-(3-hexyl-phenyl)-5-(3-methoxy-prop-1-ynyl)-3-methyl-3H-imidazol-4-yl]-(4-pyrrolidin-1-yl-piperidin-1-yl)-methanone (example 32) was hydrogenated using platinum oxide as catalyst to give the title compound as light yellow oil. MS: 495.4 (MH+).

Example 35

[5-[3-(4-Fluoro-benzyloxy)-propyl]-2-(3-hexyl-phenyl)-3-methyl-3H-imidazol-4-yl]-(4-pyrrolidin-1-yl-piperidin-1-yl)-methanone

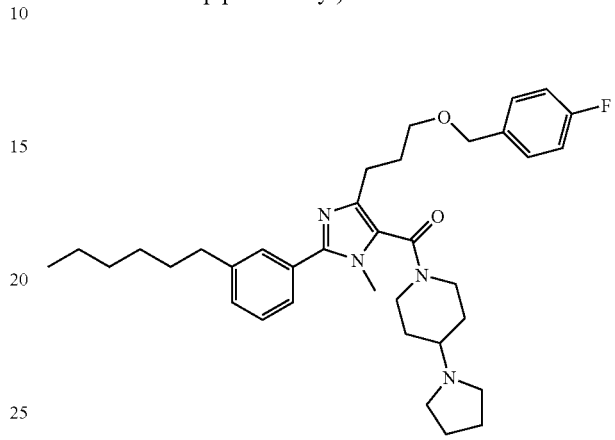

A solution of 0.200 g (0.42 mmol) of [2-(3-hexyl-phenyl)-5-(3-hydroxy-propyl)-3-methyl-3H-imidazol-4-yl]-(4-pyrrolidin-1-yl-piperidin-1-yl)-methanone (example 33) and 0.107 ml=0.162 g (0.83 mmol) of 4-fluorobenzylbromide in 5.0 ml of DMF was treated with 0.036 g (0.83 mmol) of sodium hydride (55% dispersion in mineral oil) at RT. After stirring for 125 hours, the reaction mixture was poured into crashed ice and extracted twice with $CH_2Cl_2$; the organic phases were washed with water, dried over magnesium sulfate, filtered and evaporated. The residue was purified by flash column chromatography ($CH_2Cl_2$/MeOH 98:2 to 4:1) to give 0.063 g (26%) of the title compound as light yellow oil. MS: 589.0 (MH+).

Example 36

[5-Iodo-3-methyl-2-(3-trifluoromethyl-phenyl)-3H-imidazol-4-yl]-(4-pyrrolidin-1-yl-piperidin-1-yl)-methanone

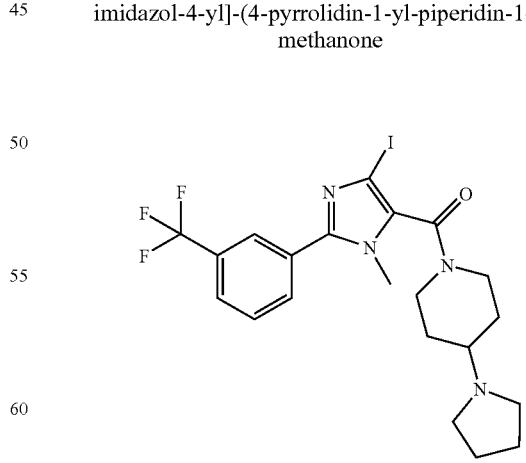

In analogy to the procedures described for intermediates 1B, 1D-F and to the procedure described for example 2, the title compound has been obtained by i) transformation of 3-trifluoromethyl-benzaldehyde into 2-(3-trifluoromethylphenyl)-1H-imidazole; ii) iodination of 2-(3-trifluoromethyl-phenyl)-1H-imidazole to give 4,5-diiodo-2-(3-trifluoromethyl-phenyl)-1H-imidazole; iii) methylation of 4,5-diiodo-2-(3-trifluoromethyl-phenyl)-1H-imidazole to give 4,5-diiodo-1-methyl-2-(3-trifluoromethyl-phenyl)-1H-imidazole; iv) carboxylation of 4,5-diiodo-1-methyl-2-(3-trifluoromethyl-phenyl)-1H-imidazole to give 5-iodo-3-methyl-2-(3-trifluoromethyl-phenyl)-3H-imidazole-4-carboxylic acid; v) coupling of 5-iodo-3-methyl-2-(3-trifluoromethyl-phenyl)-3H-imidazole-4-carboxylic acid with 4-pyrrolidin-1-yl-piperidine to give the title compound as light yellow foam. MS: 533.1 (MH+).

Example 37

[3-Methyl-2-(3-trifluoromethyl-phenyl)-3H-imidazol-4-yl]-(4-pyrrolidin-1-yl-piperidin-1-yl)-methanone

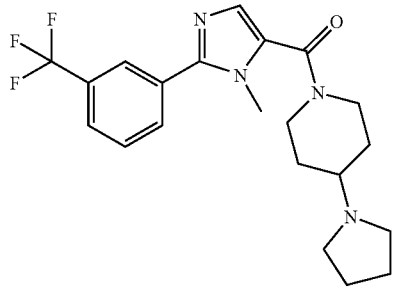

In analogy to the procedure described for example 4, [5-iodo-3-methyl-2-(3-trifluoromethyl-phenyl)-3H-imidazol-4-yl]-(4-pyrrolidin-1-yl-piperidin-1-yl)-methanone (example 36) was hydrogenated to give the title compound as light yellow oil. MS: 407.3 (MH+).

Example 38

[3-Methyl-5-pyridin-3-yl-2-(3-trifluoromethyl-phenyl)-3H-imidazol-4-yl]-(4-pyrrolidin-1-yl-piperidin-1-yl)-methanone

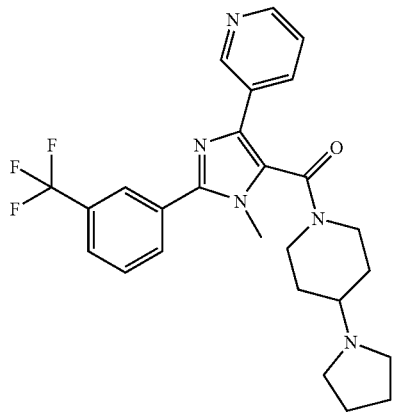

In analogy to the procedure described for example 7, [5-iodo-3-methyl-2-(3-trifluoromethyl-phenyl)-3H-imidazol-4-yl]-(4-pyrrolidin-1-yl-piperidin-1-yl)-methanone (example 36) was reacted with pyridine-3-yl-boronic acid to give the title compound as colorless oil. MS: 484.4 (MH+).

Example 39

[3-Methyl-5-pyrimidin-5-yl-2-(3-trifluoromethyl-phenyl)-3H-imidazol-4-yl]-(4-pyrrolidin-1-yl-piperidin-1-yl)-methanone

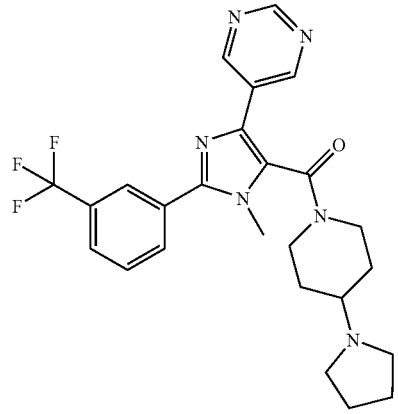

In analogy to the procedure described for example 7, [5-iodo-3-methyl-2-(3-trifluoromethyl-phenyl)-3H-imidazol-4-yl]-(4-pyrrolidin-1-yl-piperidin-1-yl)-methanone (example 36) was reacted with pyrimidine-5-yl-boronic acid to give the title compound as yellow solid. MS: 485.3 (MH+).

Example 40

[3-Methyl-2-(3-trifluoromethyl-phenyl)-5-trimethylsilanylethynyl-3H-imidazol-4-yl]-(4-pyrrolidin-1-yl-piperidin-1-yl)-methanone

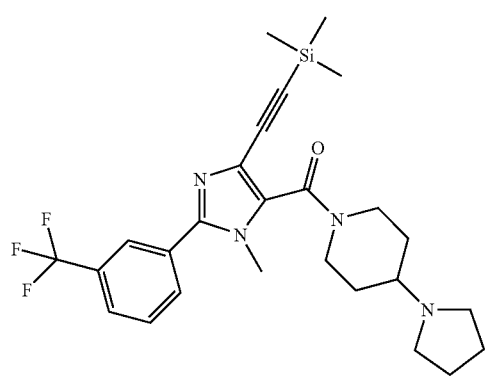

In analogy to the procedure described for example 12, [5-iodo-3-methyl-2-(3-trifluoromethyl-phenyl)-3H-imidazol-4-yl]-(4-pyrrolidin-1-yl-piperidin-1-yl)-methanone (example 36) was reacted with trimethylsilylacetylene to give the title compound as brown oil. MS: 503.3 (MH⁺).

Example 41

[5-Ethynyl-3-methyl-2-(3-trifluoromethyl-phenyl)-3H-imidazol-4-yl]-(4-pyrrolidin-1-yl-piperidin-1-yl)-methanone

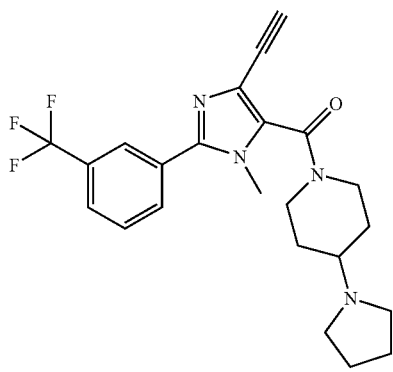

In analogy to the procedure described for example 13, [3-methyl-2-(3-trifluoromethyl-phenyl)-5-trimethylsilanyl-ethynyl-3H-imidazol-4-yl]-(4-pyrrolidin-1-yl-piperidin-1-yl)-methanone (example 40) was reacted with potassium carbonate to give the title compound as yellow oil. MS: 431.4 (MH⁺).

Example 42

[5-Ethyl-3-methyl-2-(3-trifluoromethyl-phenyl)-3H-imidazol-4-yl]-(4-pyrrolidin-1-yl-piperidin-1-yl)-methanone

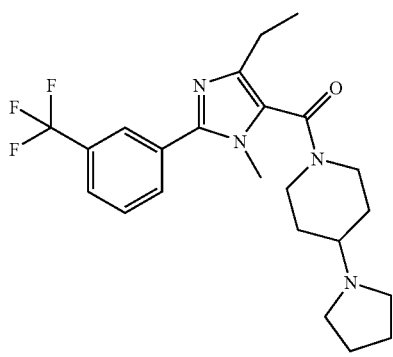

In analogy to the procedure described for example 14, [5-ethynyl-3-methyl-2-(3-trifluoromethyl-phenyl)-3H-imidazol-4-yl]-(4-pyrrolidin-1-yl-piperidin-1-yl)-methanone (example 41) was hydrogenated using platinum oxide as catalyst to give the title compound as yellow foam. MS: 435.3 (MH⁺).

Example 43

1-Methyl-5-(4-pyrrolidin-1-yl-piperidine-1-carbonyl)-2-(3-trifluoromethoxy-phenyl)-1H-imidazole-4-carbonitrile

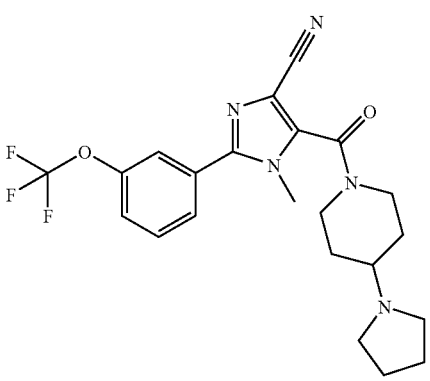

In analogy to the procedure described for example 18, [5-iodo-3-methyl-2-(3-trifluoromethoxy-phenyl)-3H-imidazol-4-yl]-(4-pyrrolidin-1-yl-piperidin-1-yl)-methanone (example 19) was reacted with zinc cyanide and tetrakis-(triphenylphosphine)-palladium in DMF to give the title compound as colorless foam. MS: 448.2 (MH⁺).

Example 44

[3-Methyl-5-pyridin-4-yl-2-(3-trifluoromethoxy-phenyl)-3H-imidazol-4-yl]-(4-pyrrolidin-1-yl-piperidin-1-yl)-methanone

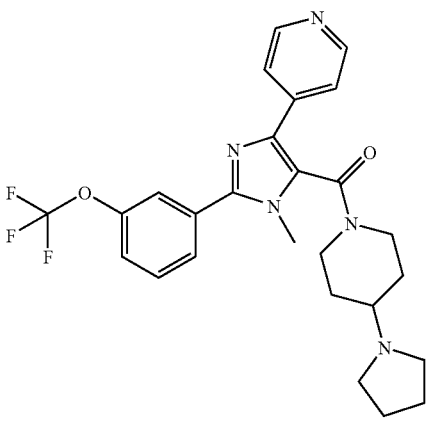

In analogy to the procedure described for example 7, [5-iodo-3-methyl-2-(3-trifluoromethoxy-phenyl)-3H-imidazol-4-yl]-(4-pyrrolidin-1-yl-piperidin-1-yl)-methanone (example 19) was reacted with pyridin-4-yl-boronic acid to give the title compound as colorless oil. MS: 500.2 (MH+).

Example 45

[2-(3-Hexyl-phenyl)-5-iodo-3-methyl-3H-imidazol-4-yl]-[4-((R)-2-hydroxymethyl-pyrrolidin-1-yl)-piperidin-1-yl]-methanone

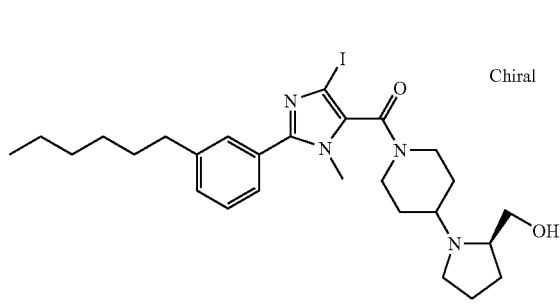

In analogy to the procedure described for example 2, 2-(3-hexyl-phenyl)-5-iodo-3-methyl-3H-imidazole-4-carboxylic acid (intermediate 1) and ((R)-1-piperidin-4-yl-pyrrolidin-2-yl)-methanol di-hydrochloride (intermediate 2) gave the title compound as light red amorphous solid. MS: 579.3 (MH+).

Example 46

[4-((R)-2-Hydroxymethyl-pyrrolidin-1-yl)-piperidin-1-yl]-[5-iodo-3-methyl-2-(3-trifluoromethoxy-phenyl)-3H-imidazol-4-yl]-methanone

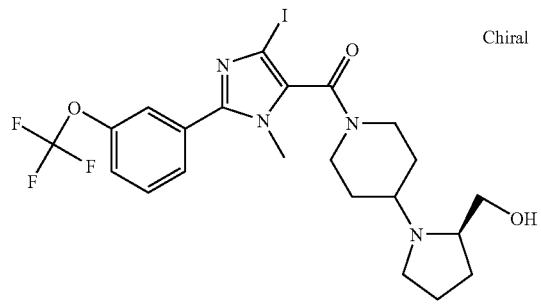

In analogy to the procedure described for example 2, 5-iodo-3-methyl-2-(3-trifluoromethoxy-phenyl)-3H-imidazole-4-carboxylic acid (example 19) and ((R)-1-piperidin-4-yl-pyrrolidin-2-yl)-methanol di-hydrochloride (intermediate 2) gave the title compound as light red amorphous solid. MS: 579.3 (MH+).

Example 47

[4-((R)-2-Hydroxymethyl-pyrrolidin-1-yl)-piperidin-1-yl]-[3-methyl-5-pyrimidin-5-yl-2-(3-trifluoromethoxy-phenyl)-3H-imidazol-4-yl]-methanone

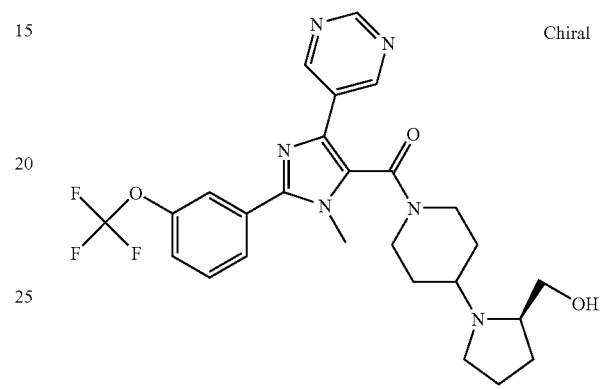

In analogy to the procedure described for example 7, [4-((R)-2-hydroxymethyl-pyrrolidin-1-yl)-piperidin-1-yl]-[5-iodo-3-methyl-2-(3-trifluoromethoxy-phenyl)-3H-imidazol-4-yl]-methanone (example 46) was reacted with pyrimidine-5-yl-boronic acid to give the title compound as light yellow oil. MS: 531.3 (MH+).

Example 48

[4-((R)-2-Hydroxymethyl-pyrrolidin-1-yl)-piperidin-1-yl]-[3-methyl-5-pyridin-4-yl-2-(3-trifluoromethoxy-phenyl)-3H-imidazol-4-yl]-methanone

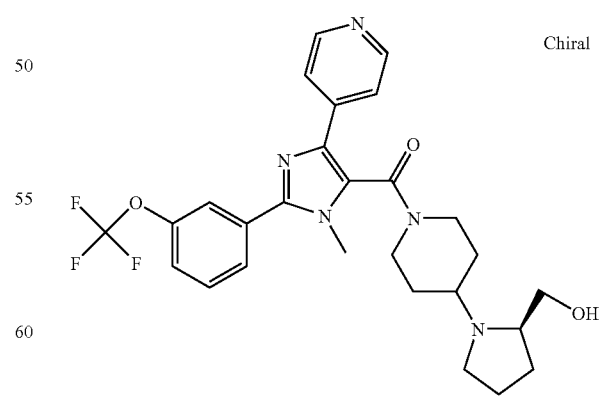

In analogy to the procedure described for example 7, [4-((R)-2-hydroxymethyl-pyrrolidin-1-yl)-piperidin-1-yl]-[5-iodo-3-methyl-2-(3-trifluoromethoxy-phenyl)-3H-imidazol- 4-yl]-methanone (example 46) was reacted with pyridin-4-yl-boronic acid to give the title compound as light yellow oil. MS: 530.2 (MH⁺).

Example 49

[4-((R)-2-Hydroxymethyl-pyrrolidin-1-yl)-piperidin-1-yl]-[3-methyl-5-pyridin-3-yl-2-(3-trifluoromethoxy-phenyl)-3H-imidazol-4-yl]-methanone

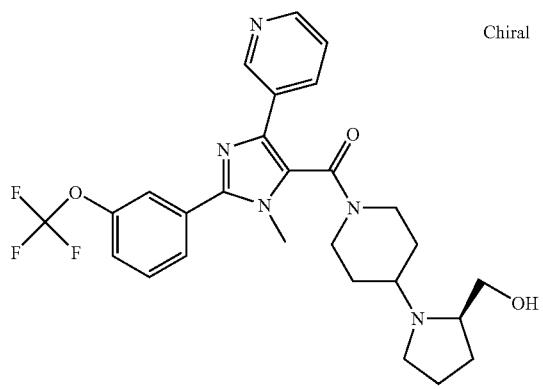

In analogy to the procedure described for example 7, [4-((R)-2-hydroxymethyl-pyrrolidin-1-yl)-piperidin-1-yl]-[5-iodo-3-methyl-2-(3-trifluoromethoxy-phenyl)-3H-imidazol-4-yl]-methanone (example 46) was reacted with pyridin-3-yl-boronic acid to give the title compound as off-white foam. MS: 530.3 (MH⁺).

Example 50

[2-(3-Hexyl-phenyl)-3-methyl-5-pyrimidin-5-yl-3H-imidazol-4-yl]-[4-((R)-2-hydroxymethyl-pyrrolidin-1-yl)-piperidin-1-yl]-methanone

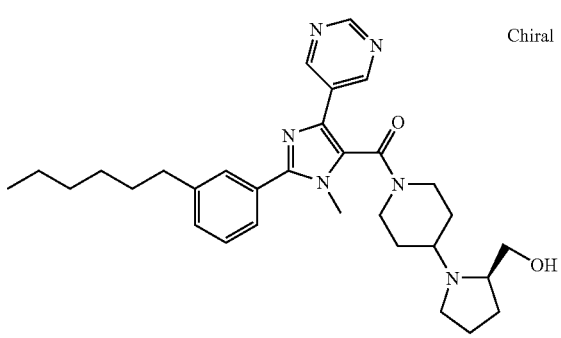

In analogy to the procedure described for example 7, [2-(3-hexyl-phenyl)-5-iodo-3-methyl-3H-imidazol-4-yl]-[4-((R)-2-hydroxymethyl-pyrrolidin-1-yl)-piperidin-1-yl]-methanone (example 45) was reacted with pyrimidine-5-yl-boronic acid to give the title compound as light yellow oil. MS: 531.3 (MH⁺).

Example 51

[2-(3-Hexyl-phenyl)-3-methyl-5-pyridin-4-yl-3H-imidazol-4-yl]-[4-((R)-2-hydroxymethyl-pyrrolidin-1-yl)-piperidin-1-yl]-methanone

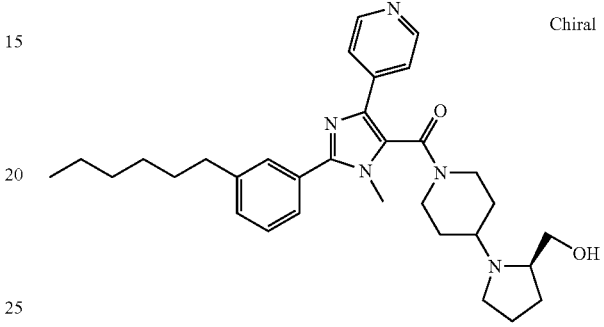

In analogy to the procedure described for example 7, [2-(3-hexyl-phenyl)-5-iodo-3-methyl-3H-imidazol-4-yl]-[4-((R)-2-hydroxymethyl-pyrrolidin-1-yl)-piperidin-1-yl]-methanone (example 45) was reacted with pyridin-4-yl-boronic acid to give the title compound as light yellow oil. MS: 530.2 (MH⁺).

Example 52

[2-(3-Hexyl-phenyl)-3-methyl-5-pyridin-3-yl-3H-imidazol-4-yl]-[4-((R)-2-hydroxymethyl-pyrrolidin-1-yl)-piperidin-1-yl]-methanone

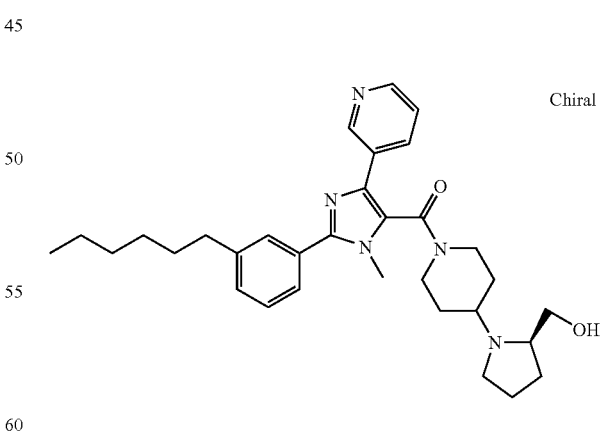

In analogy to the procedure described for example 7, [2-(3-hexyl-phenyl)-5-iodo-3-methyl-3H-imidazol-4-yl]-[4-((R)-2-hydroxymethyl-pyrrolidin-1-yl)-piperidin-1-yl]- methanone (example 45) was reacted with pyridin-3-yl-boronic acid to give the title compound as light brown oil. MS: 530.3 (MH+).

Example 53

[4-((S)-2-Hydroxymethyl-pyrrolidin-1-yl)-piperidin-1-yl]-[5-iodo-3-methyl-2-(3-trifluoromethoxy-phenyl)-3H-imidazol-4-yl]-methanone

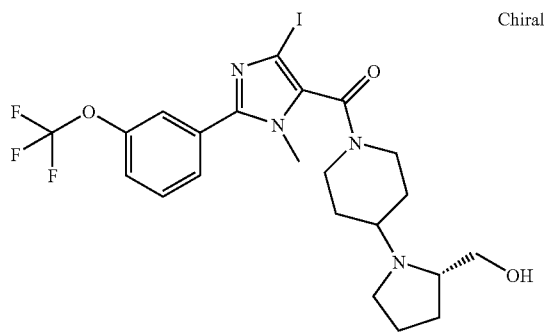

In analogy to the procedure described for example 2, 5-iodo-3-methyl-2-(3-trifluoromethoxy-phenyl)-3H-imidazole-4-carboxylic acid (example 19) and ((S)-1-piperidin-4-yl-pyrrolidin-2-yl)-methanol di-hydrochloride [prepared as described for ((R)-1-piperidin-4-yl-pyrrolidin-2-yl)-methanol di-hydrochloride (intermediate 2), but starting from (S)-(−)-pyrrolidin-2-yl-methanol] gave the title compound as brown amorphous solid. MS: 579.1 (MH+).

Example 54

[4-((S)-2-Hydroxymethyl-pyrrolidin-1-yl)-piperidin-1-yl]-[3-methyl-5-pyridin-4-yl-2-(3-trifluoromethoxy-phenyl)-3H-imidazol-4-yl]-methanone

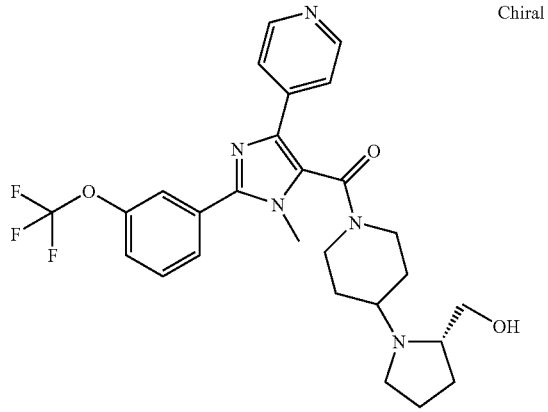

In analogy to the procedure described for example 7, [4-((S)-2-hydroxymethyl-pyrrolidin-1-yl)-piperidin-1-yl]-[5-iodo-3-methyl-2-(3-trifluoromethoxy-phenyl)-3H-imidazol-4-yl]-methanone (example 53) was reacted with pyridin-4-yl-boronic acid to give the title compound as colorless foam. MS: 530.1 (MH+).

Example 55

[4-((S)-2-Hydroxymethyl-pyrrolidin-1-yl)-piperidin-1-yl]-[3-methyl-5-pyrimidin-5-yl-2-(3-trifluoromethoxy-phenyl)-3H-imidazol-4-yl]-methanone

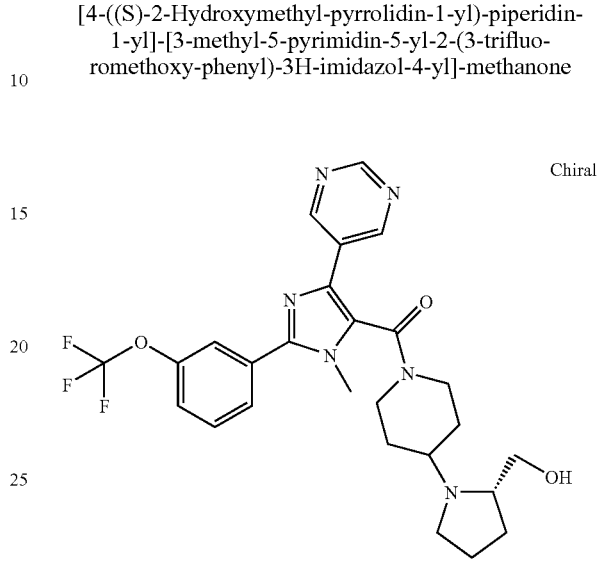

In analogy to the procedure described for example 7, [4-((S)-2-hydroxymethyl-pyrrolidin-1-yl)-piperidin-1-yl]-[5-iodo-3-methyl-2-(3-trifluoromethoxy-phenyl)-3H-imidazole-4-yl]-methanone (example 53) was reacted with pyrimidine-5-yl-boronic acid to give the title compound light brown oil. MS: 531.1 (MH+).

Example 56

[3-Cyclopropylmethyl-5-iodo-2-(3-trifluoromethyl-phenyl)-3H-imidazol-4-yl]-(4-pyrrolidin-1-yl-piperidin-1-yl)-methanone

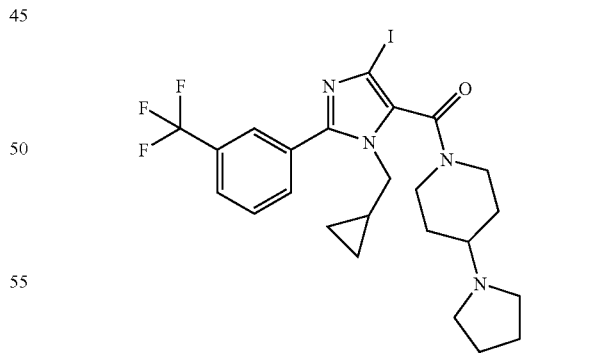

In analogy to the procedure described for intermediate 1F and to the procedure described for example 2, the title compound has been obtained by i) carboxylation of 1-cyclopropylmethyl-4,5-diiodo-2-(3-trifluoromethyl-phenyl)-1H-imidazole (intermediate 3) to give 3-cyclopropylmethyl-5-iodo-2-(3-trifluoromethyl-phenyl)-3H-imidazole-4-carboxylic acid; ii) coupling of 3-cyclopropylmethyl-5-iodo-2-(3-trifluoromethyl-phenyl)-3H-imidazole-4-carboxylic acid with 4-pyrrolidin-1-yl-piperidine to give the title compound as light yellow solid. MS: 573.2 (MH+).

Example 57

[3-Cyclopropylmethyl-5-pyridin-4-yl-2-(3-trifluoromethyl-phenyl)-3H-imidazol-4-yl]-(4-pyrrolidin-1-yl-piperidin-1-yl)-methanone

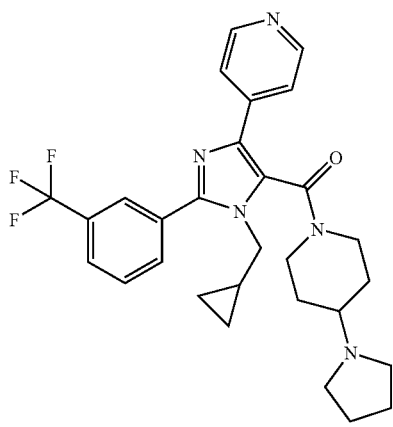

In analogy to the procedure described for example 7, [3-cyclopropylmethyl-5-iodo-2-(3-trifluoromethyl-phenyl)-3H-imidazol-4-yl]-(4-pyrrolidin-1-yl-piperidin-1-yl)-methanone (example 56) was reacted with pyridin-4-yl-boronic acid to give the title compound light yellow amorphous solid. MS: 524.5 (MH+).

Example 58

(4-Hydroxy-[1,4']bipiperidinyl-1'-yl)-[5-iodo-3-methyl-2-(3-trifluoromethyl-phenyl)-3H-imidazol-4-yl]-methanone

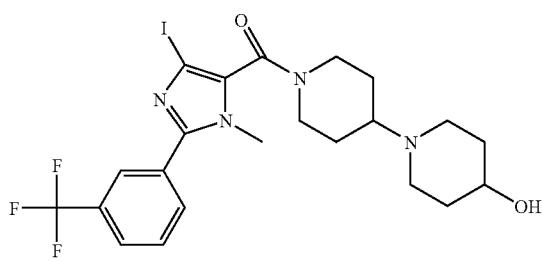

In analogy to the procedure described for example 2, 5-iodo-3-methyl-2-(3-trifluoromethyl-phenyl)-3H-imidazole-4-carboxylic acid (example 36) was coupled with [1,4']bipiperidinyl-4-ol to give the title compound as light red solid. MS: 563.2 (MH+).

Example 59

(rac)-(3-Hydroxy-[1,4']bipiperidinyl-1'-yl)-[5-iodo-3-methyl-2-(3-trifluoromethyl-phenyl)-3H-imidazol-4-yl]-methanone

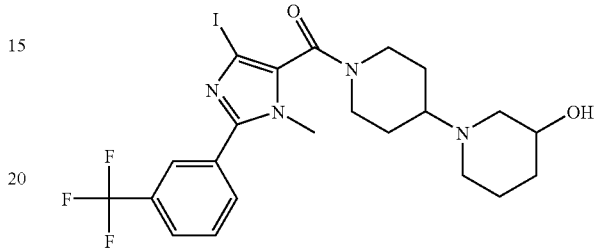

In analogy to the procedure described for example 2, 5-iodo-3-methyl-2-(3-trifluoromethyl-phenyl)-3H-imidazole-4-carboxylic acid (example 36) was coupled with (rac)-[1,4']bipiperidinyl-3-ol to give the title compound as off-white solid. MS: 563.2 (MH+).

Example 60

[2-(3,5-Bis-trifluoromethyl-phenyl)-5-iodo-3-methyl-3H-imidazol-4-yl]-(4-pyrrolidin-1-yl-piperidin-1-yl)-methanone

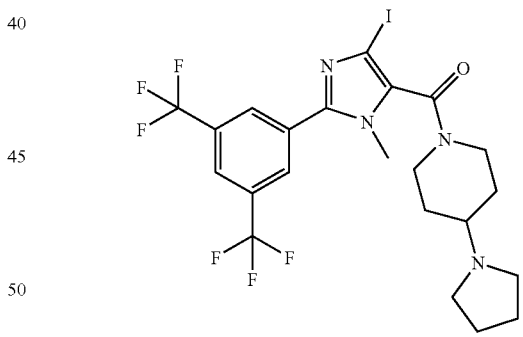

In analogy to the procedures described for intermediates 1B, 1D-F and to the procedure described for example 2, the title compound has been obtained by i) transformation of 3,5-bis-trifluoromethyl-benzaldehyde into 2-(3,5-bis-trifluoromethyl-phenyl)-1H-imidazole; ii) iodination of 2-(3,5-bis-trifluoromethyl-phenyl)-1H-imidazole to 2-(3,5-bis-trifluoromethyl-phenyl)-4,5-diiodo-1H-imidazole; iii) methylation of 2-(3,5-bis-trifluoromethyl-phenyl)-4,5-diiodo-1H-imidazole to give 2-(3,5-bis-trifluoromethyl-phenyl)-4,5-diiodo-1-methyl-1H-imidazole; iv) carboxylation of 2-(3,5-bis-trifluoromethyl-phenyl)-4,5-diiodo-1-methyl-1H-imidazole to give 2-(3,5-bis-trifluoromethyl-phenyl)-5-iodo-3-methyl-3H-imidazole-4-carboxylic acid; v) coupling of 2-(3,5-bis-trifluoromethyl-phenyl)-5-iodo-3-methyl-3H-imidazole-4-car-

Example 61

[2-(3,5-Bis-trifluoromethyl-phenyl)-3-methyl-5-pyridin-4-yl-3H-imidazol-4-yl]-(4-pyrrolidin-1-yl-piperidin-1-yl)-methanone

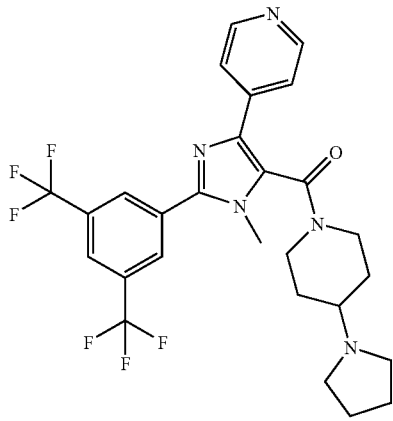

In analogy to the procedure described for example 7, [2-(3,5-bis-trifluoromethyl-phenyl)-5-iodo-3-methyl-3H-imidazol-4-yl]-(4-pyrrolidin-1-yl-piperidin-1-yl)-methanone (example 60) was reacted with pyridine-4-yl-boronic acid to give the title compound as yellow amorphous solid. MS: 552.1 (MH⁺).

Example 62

[2-(3,5-Bis-trifluoromethyl-phenyl)-3-methyl-5-pyrimidin-5-yl-3H-imidazol-4-yl]-(4-pyrrolidin-1-yl-piperidin-1-yl)-methanone

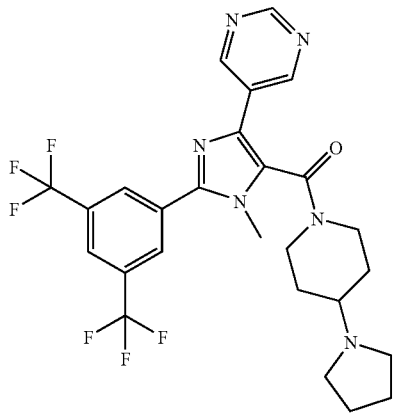

In analogy to the procedure described for example 7, [2-(3,5-bis-trifluoromethyl-phenyl)-5-iodo-3-methyl-3H-imidazol-4-yl]-(4-pyrrolidin-1-yl-piperidin-1-yl)-methanone (example 60) was reacted with pyrimidine-5-yl-boronic acid to give the title compound as yellow solid. MS: 553.1 (MH⁺).

Example 63

[3-Cyclopropyl-5-iodo-2-(3-trifluoromethyl-phenyl)-3H-imidazol-4-yl]-(4-pyrrolidin-1-yl-piperidin-1-yl)-methanone

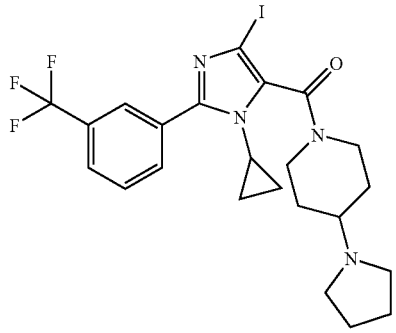

In analogy to the procedure described for intermediate 1F and to the procedure described for example 2, the title compound has been obtained by i) carboxylation of 1-cyclopropyl-4,5-diiodo-2-(3-trifluoromethyl-phenyl)-1H-imidazole (intermediate 4) to give 3-cyclopropyl-5-iodo-2-(3-trifluoromethyl-phenyl)-3H-imidazole-4-carboxylic acid; ii) coupling of 3-cyclopropyl-5-iodo-2-(3-trifluoromethyl-phenyl)-3H-imidazole-4-carboxylic acid with 4-pyrrolidin-1-yl-piperidine to give the title compound as yellow amorphous solid. MS: 559.2 (MH⁺).

Example 64

[3-Cyclopropyl-5-pyridin-4-yl-2-(3-trifluoromethyl-phenyl)-3H-imidazol-4-yl]-(4-pyrrolidin-1-yl-piperidin-1-yl)-methanone

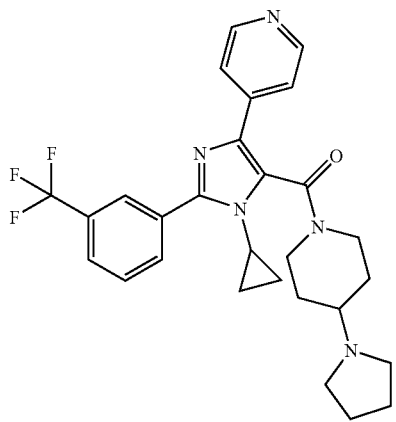

In analogy to the procedure described for example 7, [3-cyclopropyl-5-iodo-2-(3-trifluoromethyl-phenyl)-3H-imidazol-4-yl]-(4-pyrrolidin-1-yl-piperidin-1-yl)-methanone (example 63) was reacted with pyridine-4-yl-boronic acid to give the title compound as light brown oil. MS: 510.3 (MH+).

Example 65

[3-Cyclopropyl-5-pyrimidin-5-yl-2-(3-trifluoromethyl-phenyl)-3H-imidazol-4-yl]-(4-pyrrolidin-1-yl-piperidin-1-yl)-methanone

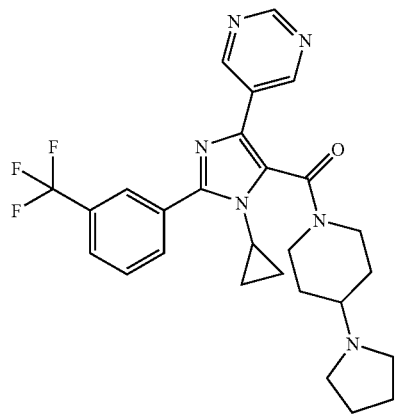

In analogy to the procedure described for example 7, [3-cyclopropyl-5-iodo-2-(3-trifluoromethyl-phenyl)-3H-imidazol-4-yl]-(4-pyrrolidin-1-yl-piperidin-1-yl)-methanone (example 63) was reacted with pyrimidine-5-yl-boronic acid to give the title compound as yellow amorphous solid. MS: 511.2 (MH+).

Example 66

[5-Iodo-3-methyl-2-(4-trifluoromethoxy-phenyl)-3H-imidazol-4-yl]-(4-pyrrolidin-1-yl-piperidin-1-yl)-methanone

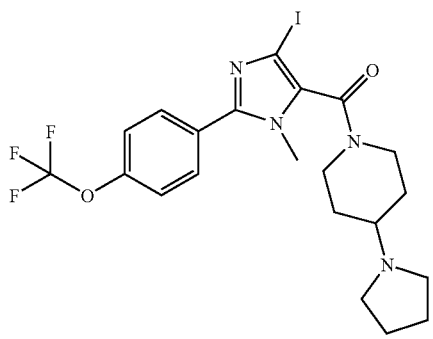

In analogy to the procedures described for intermediates 1B, 1D-F and to the procedure described for example 2, the title compound has been obtained by i) transformation of 4-trifluoromethoxy-benzaldehyde into 2-(4-trifluoromethoxy-phenyl)-1H-imidazole; ii) iodination of 2-(4-trifluoromethoxy-phenyl)-1H-imidazole to 4,5-diiodo-2-(4-trifluoromethoxy-phenyl)-1H-imidazole; iii) methylation of 4,5-diiodo-2-(4-trifluoromethoxy-phenyl)-1H-imidazole to give 4,5-diiodo-1-methyl-2-(4-trifluoromethoxy-phenyl)-1H-imidazole; iv) carboxylation of 4,5-diiodo-1-methyl-2-(4-trifluoromethoxy-phenyl)-1H-imidazole to give 5-iodo-3-methyl-2-(4-trifluoromethoxy-phenyl)-3H-imidazole-4-carboxylic acid; v) coupling of 5-iodo-3-methyl-2-(4-trifluoromethoxy-phenyl)-3H-imidazole-4-carboxylic acid with 4-pyrrolidin-1-yl-piperidine to give the title compound as yellow amorphous solid. MS: 549.3 (MH+).

Example 67

[3-Methyl-5-pyridin-4-yl-2-(4-trifluoromethoxy-phenyl)-3H-imidazol-4-yl]-(4-pyrrolidin-1-yl-piperidin-1-yl)-methanone

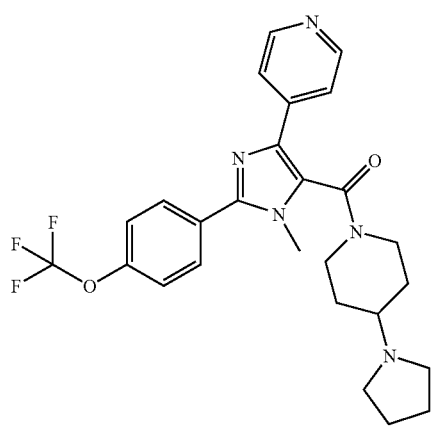

In analogy to the procedure described for example 7, [5-iodo-3-methyl-2-(4-trifluoromethoxy-phenyl)-3H-imidazol-4-yl]-(4-pyrrolidin-1-yl-piperidin-1-yl)-methanone (example 66) was reacted with pyridine-4-yl-boronic acid to give the title compound as light brown solid. MS: 500.2 (MH+).

Example 68

[3-Methyl-5-pyrimidin-5-yl-2-(4-trifluoromethoxy-phenyl)-3H-imidazol-4-yl]-(4-pyrrolidin-1-yl-piperidin-1-yl)-methanone

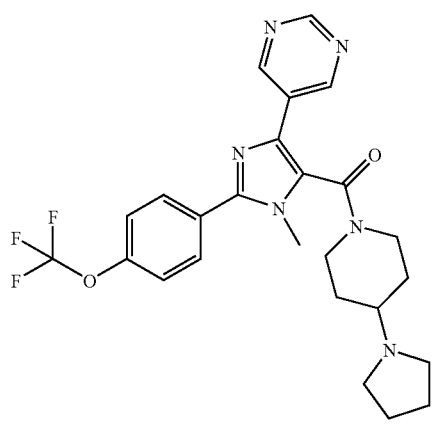

In analogy to the procedure described for example 7, [5-iodo-3-methyl-2-(4-trifluoromethoxy-phenyl)-3H-imidazol-4-yl]-(4-pyrrolidin-1-yl-piperidin-1-yl)-methanone (example 66) was reacted with pyrimidine-5-yl-boronic acid to give the title compound as colorless amorphous solid. MS: 501.1 (MH+).

Example 69

[3-Ethyl-5-iodo-2-(3-trifluoromethyl-phenyl)-3H-imidazol-4-yl]-(4-pyrrolidin-1-yl-piperidin-1-yl)-methanone

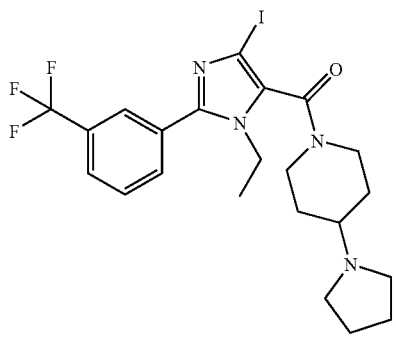

In analogy to the procedures described for intermediate 3, intermediate 1F and to the procedure described for example 2, the title compound has been obtained by i) alkylation of 4,5-diiodo-2-(3-trifluoromethyl-phenyl)-1H-imidazole to give 1-ethyl-4,5-diiodo-2-(3-trifluoromethyl-phenyl)-1H-imidazole; ii) carboxylation of 1-ethyl-4,5-diiodo-2-(3-trifluoromethyl-phenyl)-1H-imidazole to give 3-ethyl-5-iodo-2-(3-trifluoromethyl-phenyl)-3H-imidazole-4-carboxylic acid; iii) coupling of 3-ethyl-5-iodo-2-(3-trifluoromethyl-phenyl)-3H-imidazole-4-carboxylic acid with 4-pyrrolidin-1-yl-piperidine to give the title compound as off-white amorphous solid. MS: 547.1 (MH+).

Example 70

[3-Ethyl-5-pyridin-4-yl-2-(3-trifluoromethyl-phenyl)-3H-imidazol-4-yl]-(4-pyrrolidin-1-yl-piperidin-1-yl)-methanone

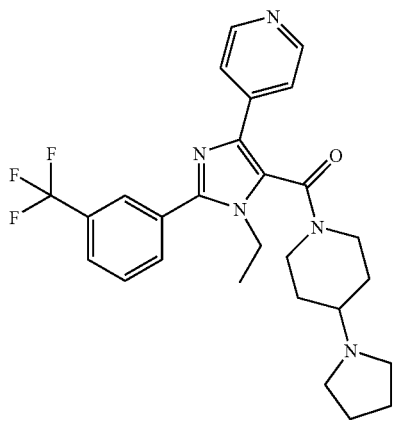

In analogy to the procedure described for example 7, [3-ethyl-5-iodo-2-(3-trifluoromethyl-phenyl)-3H-imidazol-4-yl]-(4-pyrrolidin-1-yl-piperidin-1-yl)-methanone (ex- ample 69) was reacted with pyridine-4-yl-boronic acid to give the title compound as light yellow solid. MS: 498.1 (MH+).

Example 71

[3-Ethyl-5-pyrimidin-5-yl-2-(3-trifluoromethyl-phenyl)-3H-imidazol-4-yl]-(4-pyrrolidin-1-yl-piperidin-1-yl)-methanone

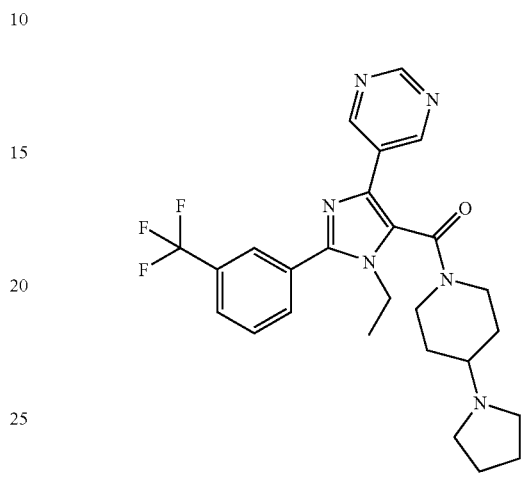

In analogy to the procedure described for example 7, [3-ethyl-5-iodo-2-(3-trifluoromethyl-phenyl)-3H-imidazol-4-yl]-(4-pyrrolidin-1-yl-piperidin-1-yl)-methanone (example 69) was reacted with pyrimidine-5-yl-boronic acid to give the title compound as light yellow solid. MS: 499.2 (MH+).

Example 72

[5-Bromo-3-methyl-2-(3-trifluoromethoxy-phenyl)-3H-imidazol-4-yl]-(4-pyrrolidin-1-yl-piperidin-1-yl)-methanone

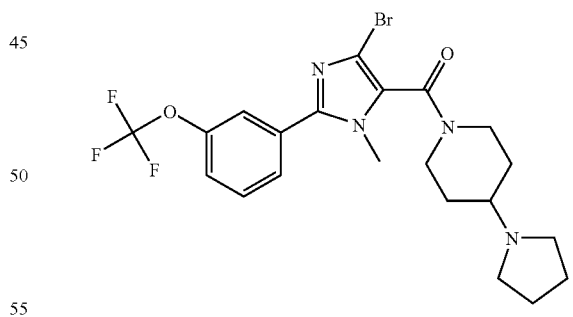

In analogy to the procedures described for intermediates 1E and 1F and to the procedure described for example 2, the title compound has been obtained by i) alkylation of 4,5-dibromo-2-(3-trifluoromethoxy-phenyl)-1H-imidazole (intermediate 5) with methyl iodide to give 4,5-dibromo-1-methyl-2-(3-trifluoromethoxy-phenyl)-1H-imidazole; ii) carboxylation of 4,5-dibromo-1-methyl-2-(3-trifluoromethoxy-phenyl)-1H-imidazole to give 5-bromo-3-methyl-2-(3-trifluoromethoxy-phenyl)-3H-imidazole-4-carboxylic acid; iii) coupling of 5-bromo-3-methyl-2-(3-trifluoromethoxy-phenyl)-3H-imidazole-4-carboxylic acid with 4-pyrrolidin-1-yl-piperidine to give the title compound as light yellow solid. MS: 501.0 (MH+, 1Br).

Example 73

[5-Bromo-3-methyl-2-(3-trifluoromethoxy-phenyl)-3H-imidazol-4-yl]-[4-((S)-2-hydroxymethyl-pyrrolidin-1-yl)-piperidin-1-yl]-methanone

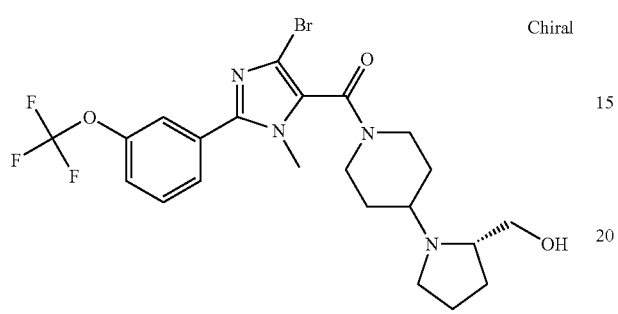

A solution of 0.15 g (0.24 mmol) of benzoic acid (S)-1-{1-[5-bromo-3-methyl-2-(3-trifluoromethoxy-phenyl)-3H-imidazole-4-carbonyl]-piperidin-4-yl}-pyrrolidin-2-ylmethyl ester [prepared in analogy to the procedure described for example 2 from 5-bromo-3-methyl-2-(3-trifluoromethoxy-phenyl)-3H-imidazole-4-carboxylic acid (example 72) and benzoic acid (S)-1-piperidin-4-yl-pyrrolidin-2-ylmethyl ester (intermediate 6C)] in 10 ml of THF/MeOH 1:1 was treated with 0.59 ml (0.59 mmol) of a LiOH solution (1.0 molar in H2O) and the mixture was stirred for 20 hours at RT. It was then poured into crashed ice, acidified with HCl (1.0 N) and extracted twice with EtOAc; the organic phases were washed with water, dried over magnesium sulfate, filtered and evaporated. The residue was purified by flash column chromatography (CH2Cl2/MeOH 98:2 to 4:1) to give 0.128 g (quant.) of the title compound as colorless amorphous solid. MS: 531.0 (MH+, 1Br).

Example 74

[5-Chloro-3-methyl-2-(3-trifluoromethyl-phenyl)-3H-imidazol-4-yl]-(4-pyrrolidin-1-yl-piperidin-1-yl)-methanone

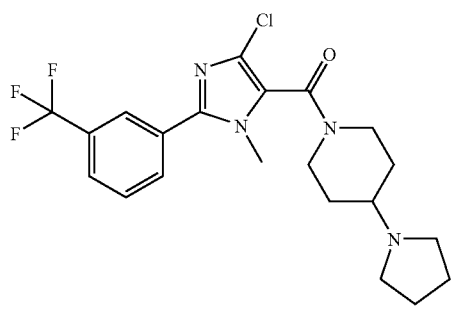

In analogy to the procedures described for example 7, for intermediate 1F and for example 2, the title compound has been obtained by the following reaction sequence: i) Suzuki reaction of 2-bromo-4,5-dichloro-1-methyl-1H-imidazole [Ali, A.; Napolitano, J. M.; Deng, Q.; Lu, Z.; Sinclair, P. J.; Taylor, G. E.; Thompson, Ch. F.; Quraishi, N.; Smith, C. J.; Hunt, J. A.; Dowst, A. A.; Chen, Y-H.; Li, H. PCT Int. Appl. (2006), 288 pp., WO 2006014413 A1] with 3-trifluoromethyl-phenyl boronic acid to give 4,5-dichloro-1-methyl-2-(3-trifluoromethyl-phenyl)-1H-imidazole; ii) carboxylation of 4,5-dichloro-1-methyl-2-(3-trifluoromethyl-phenyl)-1H-imidazole to give 5-chloro-3-methyl-2-(3-trifluoromethyl-phenyl)-3H-imidazole-4-carboxylic acid; iii) coupling of 5-chloro-3-methyl-2-(3-trifluoromethyl-phenyl)-3H-imidazole-4-carboxylic acid with 4-pyrrolidin-1-yl-piperidine to give the title compound as off-white solid. MS: 441.3 (MH+, 1Cl).

Example 75

[5-Chloro-3-methyl-2-(3-trifluoromethyl-phenyl)-3H-imidazol-4-yl]-[4-((S)-2-hydroxymethyl-pyrrolidin-1-yl)-piperidin-1-yl]-methanone

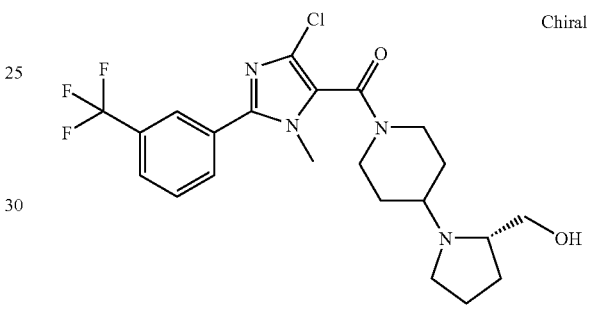

In analogy to the procedure described for example 73, benzoic acid (S)-1-{1-[5-chloro-3-methyl-2-(3-trifluoromethyl-phenyl)-3H-imidazole-4-carbonyl]-piperidin-4-yl}-pyrrolidin-2-ylmethyl ester [prepared in analogy to the procedure described for example 2 from 5-chloro-3-methyl-2-(3-trifluoromethyl-phenyl)-3H-imidazole-4-carboxylic acid (example 74) and benzoic acid (S)-1-piperidin-4-yl-pyrrolidin-2-ylmethyl ester (intermediate 6C)] has been saponified to give the title compound as colorless amorphous solid. MS: 471.2 (MH+, 1Cl).

Example 76

[3-Cyclopropyl-5-methyl-2-(4-trifluoromethoxy-phenyl)-3H-imidazol-4-yl]-(4-pyrrolidin-1-yl-piperidin-yl)-methanone

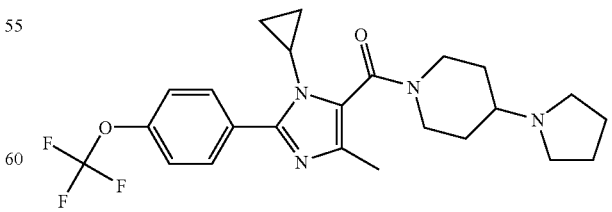

In analogy to the procedure described for example 2, the title compound has been obtained by coupling of 3-cyclopropyl-5-methyl-2-(4-trifluoromethoxy-phenyl)-3H-imidazole-4-carboxylic acid (intermediate 7) with 4-pyrrolidin-1-ylpiperidine to give the title compound as a colorless amorphous solid. MS: 463.3 (MH+).

Example 77

[3-Cyclopropyl-5-methyl-2-(4-trifluoromethoxy-phenyl)-3H-imidazol-4-yl]-[4-((S)-2-hydroxymethyl-pyrrolidin-1-yl)-piperidin-1-yl]-methanone

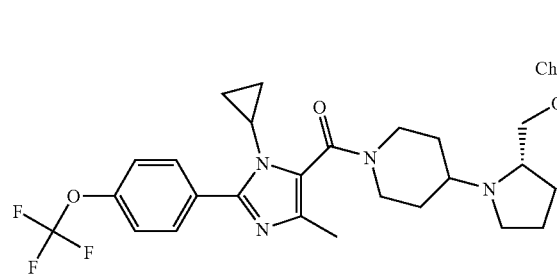

In analogy to the procedure described for example 2, the title compound has been obtained by coupling of 3-cyclopropyl-5-methyl-2-(4-trifluoromethoxy-phenyl)-3H-imidazole-4-carboxylic acid (intermediate 7) with ((S)-1-piperidin-4-yl-pyrrolidin-2-yl)-methanol di-hydrochloride [prepared as described for ((R)-1-piperidin-4-yl-pyrrolidin-2-yl)-methanol di-hydrochloride (intermediate 2), but starting from (S)-(−)-pyrrolidin-2-yl-methanol] to give the title compound as a colorless amorphous solid. MS: 493.3 (MH+).

Example 78

[3-Cyclopropyl-5-methyl-2-(3-trifluoromethoxy-phenyl)-3H-imidazol-4-yl]-(4-pyrrolidin-1-yl-piperidin-1-yl)-methanone

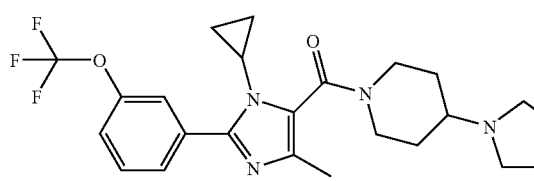

In analogy to the procedure described for example 2, the title compound has been obtained by coupling of 3-cyclopropyl-5-methyl-2-(3-trifluoromethoxy-phenyl)-3H-imidazole-4-carboxylic acid (prepared in analogy to the sequence described for the preparation of intermediate 7, but using 3-trifluoromethoxy-benzoyl chloride instead of 4-trifluoromethoxy-benzoyl chloride in step 7B) with 4-pyrrolidin-1-yl-piperidine to give the title compound as colorless amorphous solid. MS: 463.3 (MH+).

Example 79

[3-Cyclopropyl-5-methyl-2-(3-trifluoromethoxy-phenyl)-3H-imidazol-4-yl]-[4-((S)-2-hydroxymethyl-pyrrolidin-1-yl)-piperidin-1-yl]-methanone

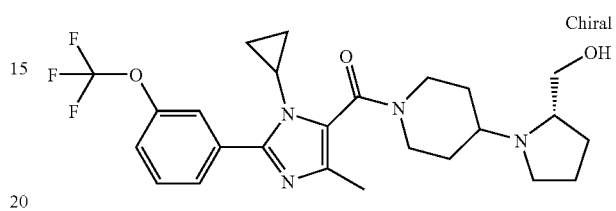

In analogy to the procedure described for example 2, the title compound has been obtained by coupling of 3-cyclopropyl-5-methyl-2-(3-trifluoromethoxy-phenyl)-3H-imidazole-4-carboxylic acid (see example 78) with ((S)-1-piperidin-4-yl-pyrrolidin-2-yl)-methanol di-hydrochloride [prepared as described for ((R)-1-piperidin-4-yl-pyrrolidin-2-yl)-methanol di-hydrochloride (intermediate 2), but starting from (S)-(−)-pyrrolidin-2-yl-methanol] to give the title compound as colorless amorphous solid. MS: 493.3 (MH+).

Example 80

[3-Cyclopropyl-5-pyridin-3-yl-2-(4-trifluoromethoxy-phenyl)-3H-imidazol-4-yl]-(4-pyrrolidin-1-yl-piperidin-1-yl)-methanone

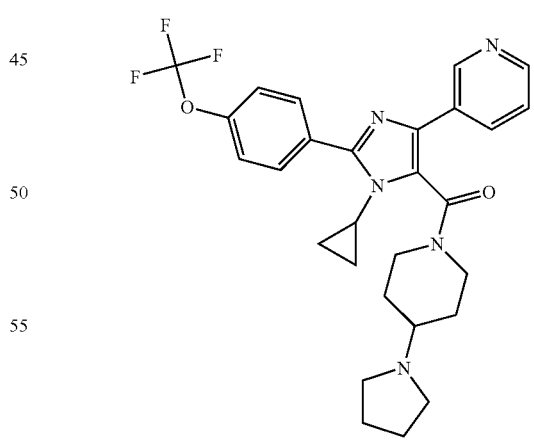

In analogy to the procedure described for example 2, the title compound has been obtained by coupling of 3-cyclopropyl-5-pyridin-3-yl-2-(4-trifluoromethoxy-phenyl)-3H-imidazole-4-carboxylic acid sodium salt (intermediate 8) with

Example 81

[3-Cyclopropyl-5-pyridin-3-yl-2-(4-trifluoromethoxy-phenyl)-3H-imidazol-4-yl]-[4-((S)-2-hydroxymethyl-pyrrolidin-1-yl)-piperidin-1-yl]-methanone

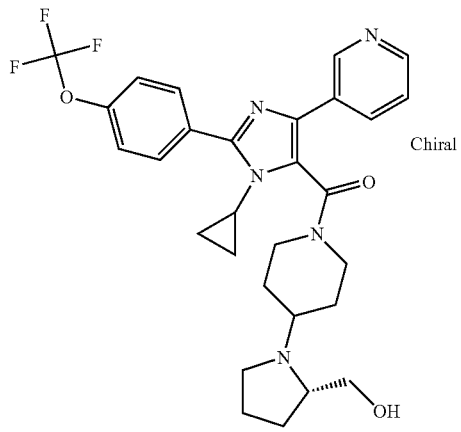

In analogy to the procedure described for example 2, the title compound has been obtained by coupling of 3-cyclopropyl-5-pyridin-3-yl-2-(4-trifluoromethoxy-phenyl)-3H-imidazole-4-carboxylic acid sodium salt (intermediate 8) with ((S)-1-piperidin-4-yl-pyrrolidin-2-yl)-methanol di-hydrochloride [prepared as described for ((R)-1-piperidin-4-yl-pyrrolidin-2-yl)-methanol di-hydrochloride (intermediate 2), but starting from (S)-(−)-pyrrolidin-2-yl-methanol] to give the title compound as a colorless amorphous solid. MS: 556.4 (MH$^+$).

Example 82

[3-Cyclopropyl-5-pyridin-3-yl-2-(3-trifluoromethoxy-phenyl)-3H-imidazol-4-yl]-(4-pyrrolidin-1-yl-piperidin-1-yl)-methanone

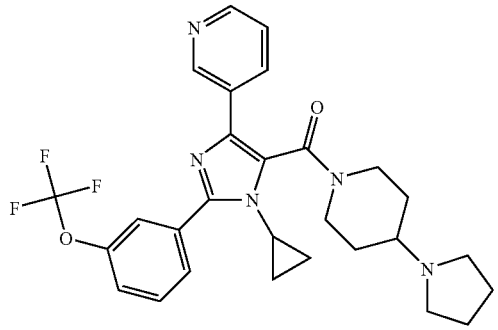

In analogy to the procedure described for example 2, the title compound has been obtained by coupling of 3-cyclopropyl-5-pyridin-3-yl-2-(3-trifluoromethoxy-phenyl)-3H-imidazole-4-carboxylic acid sodium salt (prepared in analogy to the sequence described for the preparation of intermediate 8, but using [cyclopropyl-(3-trifluoromethoxy-benzoyl)-amino]-acetic acid ethyl ester instead of [cyclopropyl-(4-trifluoromethoxy-benzoyl)-amino]-acetic acid ethyl ester in step 8A) with 4-pyrrolidin-1-yl-piperidine to give the title compound as a colorless amorphous solid. MS: 526.4 (MH$^+$).

Example 83

[3-Cyclopropyl-5-pyridin-3-yl-2-(3-trifluoromethoxy-phenyl)-3H-imidazol-4-yl]-[4-((S)-2-hydroxymethyl-pyrrolidin-1-yl)-piperidin-1-yl]-methanone

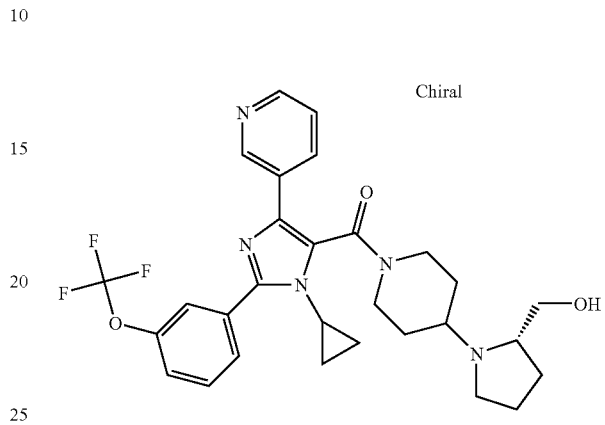

In analogy to the procedure described for example 2, the title compound has been obtained by coupling of 3-cyclopropyl-5-pyridin-3-yl-2-(3-trifluoromethoxy-phenyl)-3H-imidazole-4-carboxylic acid sodium salt (see example 82) with ((S)-1-piperidin-4-yl-pyrrolidin-2-yl)-methanol di-hydrochloride [prepared as described for ((R)-1-piperidin-4-yl-pyrrolidin-2-yl)-methanol di-hydrochloride (intermediate 2), but starting from (S)-(−)-pyrrolidin-2-yl-methanol] to give the title compound as a colorless amorphous solid. MS: 556.4 (MH$^+$).

Example 84

[3-Cyclopropyl-5-(6-hydroxy-pyridin-3-yl)-2-(4-trifluoromethoxy-phenyl)-3H-imidazol-4-yl]-(4-pyrrolidin-1-yl-piperidin-1-yl)-methanone

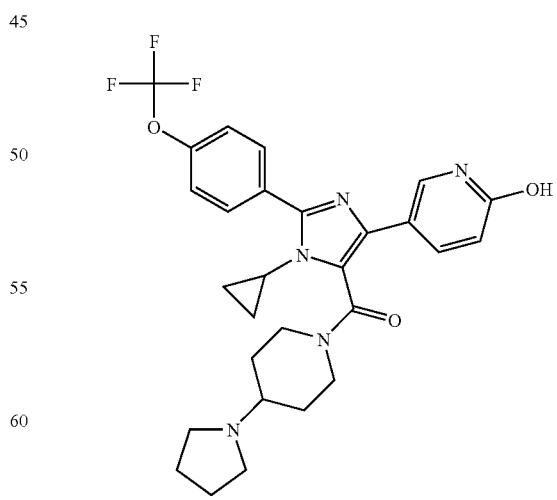

In analogy to the procedure described for example 2, the title compound has been obtained by coupling of 3-cyclopropyl-5-(6-hydroxy-pyridin-3-yl)-2-(4-trifluoromethoxy-phenyl)-3H-imidazole-4-carboxylic acid (intermediate 9) with 4-pyrrolidin-1-yl-piperidine to give the title compound as a colorless amorphous solid. MS: 542.4 (MH⁺).

Example 85

[3-Cyclopropyl-5-(6-hydroxy-pyridin-3-yl)-2-(4-trifluoromethoxy-phenyl)-3H-imidazol-4-yl]-[4-((S)-2-hydroxymethyl-pyrrolidin-1-yl)-piperidin-1-yl]-methanone

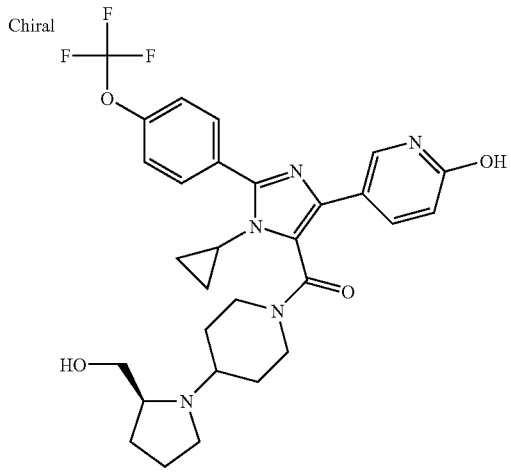

In analogy to the procedure described for example 2, the title compound has been obtained by coupling of 3-cyclopropyl-5-(6-hydroxy-pyridin-3-yl)-2-(4-trifluoromethoxy-phenyl)-3H-imidazole-4-carboxylic acid (intermediate 9) with ((S)-1-piperidin-4-yl-pyrrolidin-2-yl)-methanol di-hydrochloride [prepared as described for ((R)-1-piperidin-4-yl-pyrrolidin-2-yl)-methanol di-hydrochloride (intermediate 2), but starting from (S)-(−)-pyrrolidin-2-yl-methanol] to give the title compound as yellow amorphous solid. MS: 572.4 (MH⁺).

Example 86

[3-Cyclopropyl-5-(6-hydroxy-pyridin-3-yl)-2-(3-trifluoromethoxy-phenyl)-3H-imidazol-4-yl]-(4-pyrrolidin-1-yl-piperidin-1-yl)-methanone

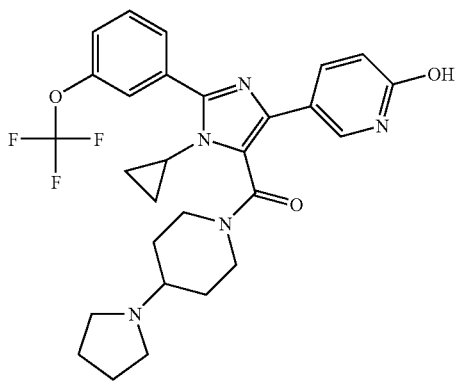

In analogy to the procedure described for example 2, the title compound has been obtained by coupling of 3-cyclopropyl-5-(6-hydroxy-pyridin-3-yl)-2-(3-trifluoromethoxy-phenyl)-3H-imidazole-4-carboxylic acid (prepared in analogy to the sequence described for the preparation of intermediate 9, using [cyclopropyl-(3-trifluoromethoxy-benzoyl)-amino]-acetic acid ethyl ester instead of [cyclopropyl-(4-trifluoromethoxy-benzoyl)-amino]-acetic acid ethyl ester in step 9A) with 4-pyrrolidin-1-yl-piperidine to give the title compound as a colorless amorphous solid. MS: 542.4 (MH⁺).

Example 87

[3-Cyclopropyl-5-(6-hydroxy-pyridin-3-yl)-2-(3-trifluoromethoxy-phenyl)-3H-imidazol-4-yl]-[4-((S)-2-hydroxymethyl-pyrrolidin-1-yl)-piperidin-1-yl]-methanone

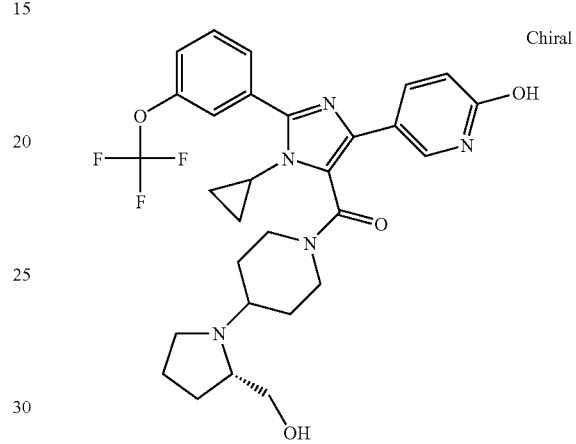

In analogy to the procedure described for example 2, the title compound has been obtained by coupling of 3-cyclopropyl-5-(6-hydroxy-pyridin-3-yl)-2-(3-trifluoromethoxy-phenyl)-3H-imidazole-4-carboxylic acid (see example 86) with ((S)-1-piperidin-4-yl-pyrrolidin-2-yl)-methanol di-hydrochloride [prepared as described for ((R)-1-piperidin-4-yl-pyrrolidin-2-yl)-methanol di-hydrochloride (intermediate 2), but starting from (S)-(−)-pyrrolidin-2-yl-methanol] to give the title compound as a colorless amorphous solid. MS: 572.4 (MH⁺).

Example 88

[3-Cyclopropyl-5-(2-methylsulfanyl-pyrimidin-5-yl)-2-(4-trifluoromethoxy-phenyl)-3H-imidazol-4-yl]-(4-pyrrolidin-1-yl-piperidin-1-yl)-methanone

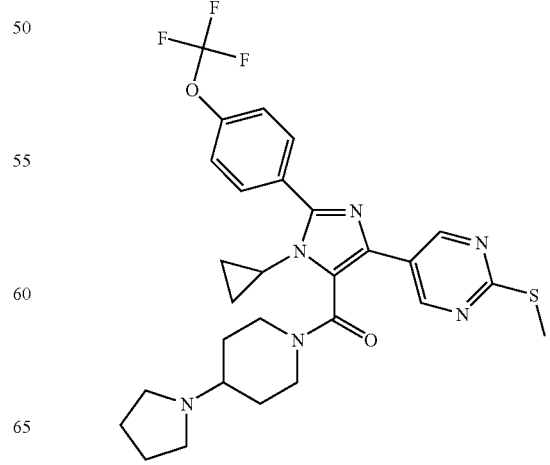

In analogy to the procedure described for example 2, the title compound has been obtained by coupling of 3-cyclopropyl-5-(2-methylsulfanyl-pyrimidin-5-yl)-2-(4-trifluoromethoxy-phenyl)-3H-imidazole-4-carboxylic acid sodium salt (intermediate 10) with 4-pyrrolidin-1-yl-piperidine to give the title compound as yellow amorphous solid. MS: 573.2 (MH⁺).

Example 89

[3-Cyclopropyl-5-(2-methylsulfanyl-pyrimidin-5-yl)-2-(3-trifluoromethoxy-phenyl)-3H-imidazol-4-yl]-(4-pyrrolidin-1-yl-piperidin-1-yl)-methanone

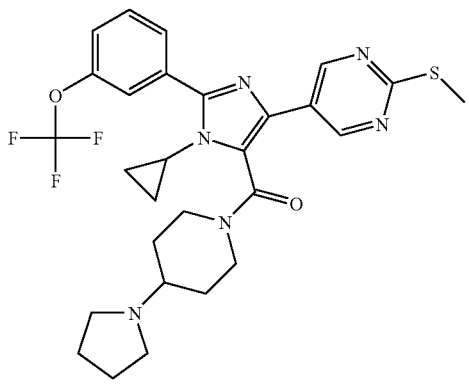

In analogy to the procedure described for example 2, the title compound has been obtained by coupling of 3-cyclopropyl-5-(2-methylsulfanyl-pyrimidin-5-yl)-2-(3-trifluoromethoxy-phenyl)-3H-imidazole-4-carboxylic acid sodium salt (prepared in analogy to the sequence described for the preparation of intermediate 10, but using [cyclopropyl-(3-trifluoromethoxy-benzoyl)-amino]-acetic acid ethyl ester instead of [cyclopropyl-(4-trifluoromethoxy-benzoyl)-amino]-acetic acid ethyl ester in step 10A) with 4-pyrrolidin-1-yl-piperidine to give the title compound as yellow amorphous solid. MS: 573.2 (MH⁺).

Example 90

[3-Cyclopropyl-5-pyrimidin-5-yl-2-(4-trifluoromethoxy-phenyl)-3H-imidazol-4-yl]-(4-pyrrolidin-1-yl-piperidin-1-yl)-methanone

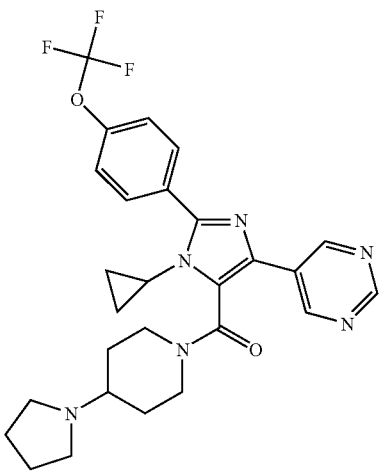

To a solution of 0.08 g (0.14 mmol) of [3-cyclopropyl-5-(2-methylsulfanyl-pyrimidin-5-yl)-2-(4-trifluoromethoxy-phenyl)-3H-imidazol-4-yl]-(4-pyrrolidin-1-yl-piperidin-1-yl)-methanone (example 88) in 1 ml of EtOH was added a generous spatula of Rainey nickel. The mixture was stirred for 15 minutes after which time the reaction was filtered over Hyflo and concentrated. Purification by flash column chromatography [CH₂Cl₂/MeOH 8:2] afforded 0.03 g (38%) of the title compound as a colorless amorphous solid. MS: 527.2 (MH⁺)

Example 91

[3-Cyclopropyl-5-pyrimidin-5-yl-2-(3-trifluoromethoxy-phenyl)-3H-imidazol-4-yl]-(4-pyrrolidin-1-yl-piperidin-1-yl)-methanone

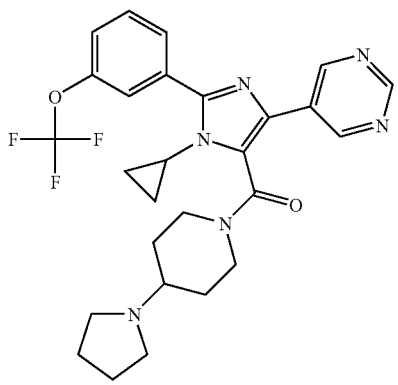

In analogy to the procedure described for example 90, [3-cyclopropyl-5-(2-methylsulfanyl-pyrimidin-5-yl)-2-(3-trifluoromethoxy-phenyl)-3H-imidazol-4-yl]-(4-pyrrolidin-1-yl-piperidin-1-yl)-methanone (example 89) was treated with Raney nickel in ethanol to give the title compound as yellow amorphous solid. MS: 527.2 (MH⁺).

Example 92

[5-(2-Amino-pyrimidin-5-yl)-3-cyclopropyl-2-(4-trifluoromethoxy-phenyl)-3H-imidazol-4-yl]-(4-pyrrolidin-1-yl-piperidin-1-yl)-methanone

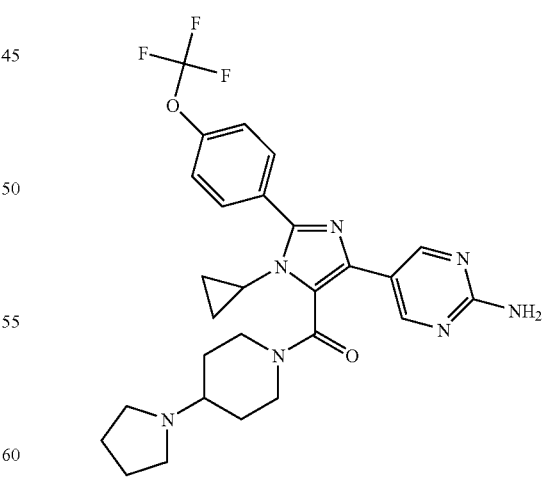

0.06 g (0.1 mmol) of [3-cyclopropyl-5-(2-methylsulfanyl-pyrimidin-5-yl)-2-(4-trifluoromethoxy-phenyl)-3H-imidazol-4-yl]-(4-pyrrolidin-1-yl-piperidin-1-yl)-methanone (example 88) was dissolved in 1 ml of DMA and 0.5 ml of hydrazine monohydrate. The mixture was heated to 100° C.

for 24 h after which time the solvent was evaporated, then it was re-dissolved in EtOH and a generous spatula of Rainey nickel was added. The mixture was stirred for 1 h after which time it was filtered over Hyflo and concentrated. Purification by flash column chromatography [CH$_2$Cl$_2$/MeOH 8:2] afforded 0.01 g (17%) of the title compound as a colorless amorphous solid. MS: 542.2 (MH$^+$).

Example 93

[5-(6-Amino-pyridin-3-yl)-3-cyclopropyl-2-(4-trifluoromethoxy-phenyl)-3H-imidazol-4-yl]-(4-pyrrolidin-1-yl-piperidin-1-yl)-methanone

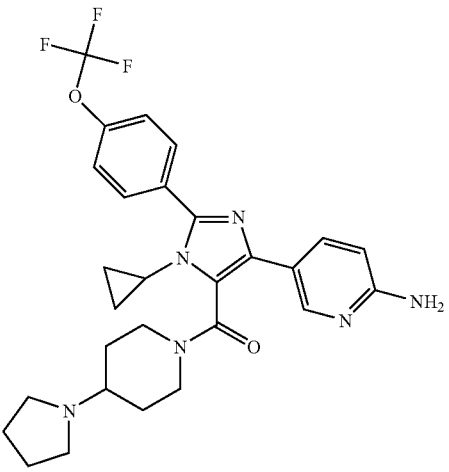

0.2 g (0.2 mmol) of [3-cyclopropyl-5-(6-dibenzylamino-pyridin-3-yl)-2-(4-trifluoromethoxy-phenyl)-3H-imidazol-4-yl]-(4-pyrrolidin-1-yl-piperidin-1-yl)-methanone (intermediate 11) was dissolved in 3 ml of HBr/acetic acid and the mixture heated to 100° C. for 24 h. The solvent was evaporated and the residue taken up in CH$_2$Cl$_2$, washed with saturated sodium hydrogen carbonate solution, dried with sodium sulphate and concentrated. Purification by flash column chromatography [CH$_2$Cl$_2$/MeOH 8:2] afforded 0.05 g (39%) of the title compound as a colorless amorphous solid. MS: 541.2 (MH$^+$)

Example 94

[5-(6-Amino-pyridin-3-yl)-3-cyclopropyl-2-(3-trifluoromethoxy-phenyl)-3H-imidazol-4-yl]-(4-pyrrolidin-1-yl-piperidin-1-yl)-methanone

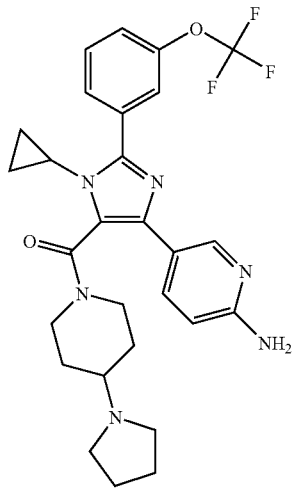

In analogy to the procedure described for example 93, the title compound has been obtained by reaction of [3-cyclopropyl-5-(6-dibenzylamino-pyridin-3-yl)-2-(3-trifluoromethoxy-phenyl)-3H-imidazol-4-yl]-(4-pyrrolidin-1-yl-piperidin-1-yl)-methanone (prepared in analogy to the sequence described for the preparation of intermediate 11, but using [cyclopropyl-(3-trifluoromethoxy-benzoyl)-amino]-acetic acid ethyl ester instead of [cyclopropyl-(4-trifluoromethoxy-benzoyl)-amino]-acetic acid ethyl ester in step 11A) with HBr/acetic acid at 100° C. as yellow amorphous solid. MS: 541.2 (MH$^+$).

Example 95

[3-Cyclopropyl-5-(1H-[1,2,4]triazol-3-yl)-2-(4-trifluoromethoxy-phenyl)-3H-imidazol-4-yl]-(4-pyrrolidin-1-yl-piperidin-1-yl)-methanone

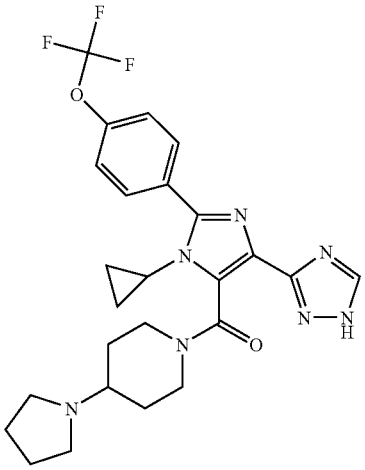

A solution of 0.07 g (0.1 mmol) of [5-(1-benzyl-1H-[1,2,4]triazol-3-yl)-3-cyclopropyl-2-(4-trifluoromethoxy-phenyl)-3H-imidazol-4-yl]-(4-pyrrolidin-1-yl-piperidin-1-yl)-methanone (intermediate 12) and a generous spatula of 10% palladium on activated charcoal in 1 ml of MeOH made acidic by addition of a few drops of 25% HCl was stirred under one atmosphere of hydrogen for 16 h. Then, the mixture was filtered over Hyflo, concentrated and the residue taken up in CH$_2$Cl$_2$. The organic phase was washed with saturated sodium hydrogen carbonate solution, dried with sodium sulphate and concentrated. Purification by flash column chromatography [CH$_2$Cl$_2$/MeOH 9:1 to 8:2] afforded 0.04 g (64%) of the title compound as a colorless amorphous solid. MS: 516.2 (MH$^+$).

Example 96

[3-Cyclopropyl-5-(2-hydroxy-pyrimidin-5-yl)-2-(4-trifluoromethoxy-phenyl)-3H-imidazol-4-yl]-(4-pyrrolidin-1-yl-piperidin-1-yl)-methanone

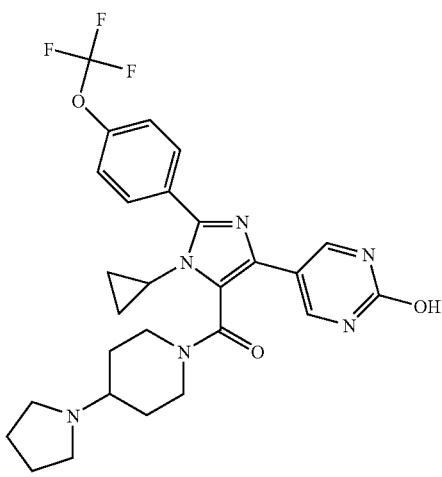

A solution of 0.06 g (0.1 mmol) of [3-cyclopropyl-5-(2-methylsulfanyl-pyrimidin-5-yl)-2-(4-trifluoromethoxy-phenyl)-3H-imidazol-4-yl]-(4-pyrrolidin-1-yl-piperidin-1-yl)-methanone (example 88) and 0.1 ml of 6M sodium hydroxide solution in 0.5 ml of DMSO was heated to 100° C. for 3 h. The DMSO was removed using an Isolute SPE 103 cartridge, and the crude product purified by preparative HPLC affording 0.01 g (22%) of the title compound as a colorless amorphous solid. MS: 543.2 (MH$^+$).

Example 97

[3-Cyclopropyl-5-(1H-pyrazol-4-yl)-2-(4-trifluoromethoxy-phenyl)-3H-imidazol-4-yl]-(4-pyrrolidin-1-yl-piperidin-1-yl)-methanone

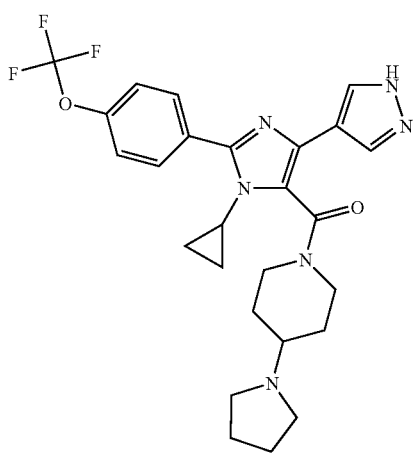

In analogy to the procedure described in example 95, the title compound has been obtained from [5-(1-benzyl-1H-pyrazol-4-yl)-3-cyclopropyl-2-(4-trifluoromethoxy-phenyl)-3H-imidazol-4-yl]-(4-pyrrolidin-1-yl-piperidin-1-yl)-methanone (intermediate 13) by hydrogenation with 10% palladium on charcoal to give the title compound as colorless amorphous solid. MS: 515.2 (MH$^+$).

Example 98

[3-Cyclopropyl-5-(1H-pyrazol-4-yl)-2-(3-trifluoromethoxy-phenyl)-3H-imidazol-4-yl]-(4-pyrrolidin-1-yl-piperidin-1-yl)-methanone

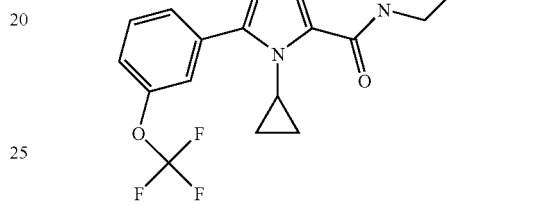

In analogy to the procedure described in example 95, the title compound has been obtained from [5-(1-benzyl-1H-pyrazol-4-yl)-3-cyclopropyl-2-(3-trifluoromethoxy-phenyl)-3H-imidazol-4-yl]-(4-pyrrolidin-1-yl-piperidin-1-yl)-methanone (prepared in analogy to the sequence described for the preparation of intermediate 13, but using [cyclopropyl-(3-trifluoromethoxy-benzoyl)-amino]-acetic acid ethyl ester instead of [cyclopropyl-(4-trifluoromethoxy-benzoyl)-amino]-acetic acid ethyl ester in step 13A) by hydrogenation with 10% palladium on charcoal to give the title compound as colorless amorphous solid. MS: 515.2 (MH$^+$).

Example 99

[3-Cyclopropyl-5-(1H-[1,2,3]triazol-4-yl)-2-(4-trifluoromethoxy-phenyl)-3H-imidazol-4-yl]-(4-pyrrolidin-1-yl-piperidin-1-yl)-methanone

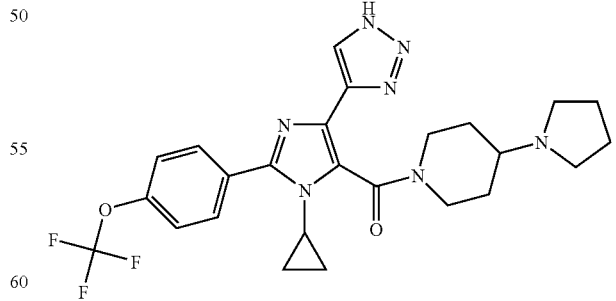

In analogy to the procedure described in example 95, the title compound has been obtained from [5-(1-benzyl-1H-[1,2,3]triazol-4-yl)-3-cyclopropyl-2-(4-trifluoromethoxy-phenyl)-3H-imidazol-4-yl]-(4-pyrrolidin-1-yl-piperidin-1-yl)-methanone (intermediate 14) by hydrogenation with 10%

Example 100

[3-Cyclopropyl-5-(2-hydroxy-pyridin-4-yl)-2-(3-trifluoromethoxy-phenyl)-3H-imidazol-4-yl]-(4-pyrrolidin-1-yl-piperidin-1-yl)-methanone

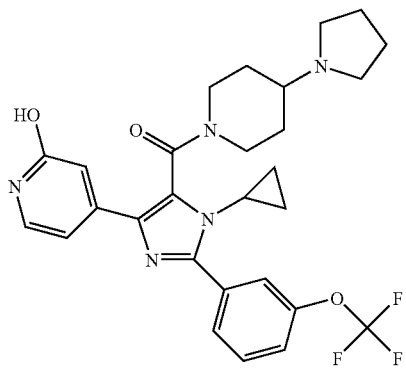

In analogy to the procedure described for example 2, the title compound has been obtained by coupling of 3-cyclopropyl-5-(2-hydroxy-pyridin-4-yl)-2-(3-trifluoromethoxy-phenyl)-3H-imidazole-4-carboxylic acid (prepared in analogy to the sequence described for the preparation of intermediate 9, but using [cyclopropyl-(3-trifluoromethoxy-benzoyl)-amino]-acetic acid ethyl ester instead of [cyclopropyl-(4-trifluoromethoxy-benzoyl)-amino]-acetic acid ethyl ester and 2-benzyloxy-isonicotinic acid instead of 6-benzyloxy-nicotinic acid in step 9A) with 4-pyrrolidin-1-yl-piperidine to give the title compound as yellow amorphous solid. MS: 542.2 (MH+).

Example 101

[3-Cyclopropyl-5-(2-hydroxy-pyridin-4-yl)-2-(4-trifluoromethoxy-phenyl)-3H-imidazol-4-yl]-(4-pyrrolidin-1-yl-piperidin-1-yl)-methanone

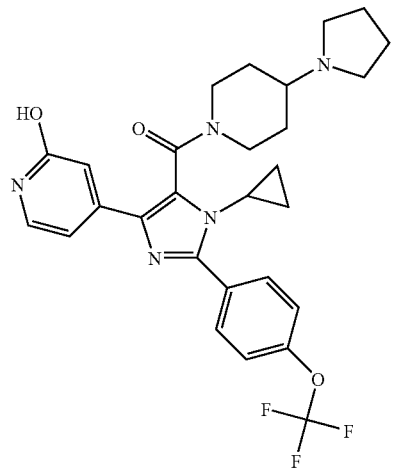

In analogy to the procedure described for example 2, the title compound has been obtained by coupling of 3-cyclopropyl-5-(2-hydroxy-pyridin-4-yl)-2-(4-trifluoromethoxy-phenyl)-3H-imidazole-4-carboxylic acid (prepared in analogy to the sequence described for the preparation of intermediate 9, but using 2-benzyloxy-isonicotinic acid instead of 6-benzyloxy-nicotinic acid in step 9A) with 4-pyrrolidin-1-yl-piperidine to give the title compound as yellow amorphous solid. MS: 542.2 (MH+).

Example 102

[3-Cyclopropyl-5-methyl-2-(3-morpholin-4-yl-5-trifluoromethyl-phenyl)-3H-imidazol-4-yl]-(4-pyrrolidin-1-yl-piperidin-1-yl)-methanone

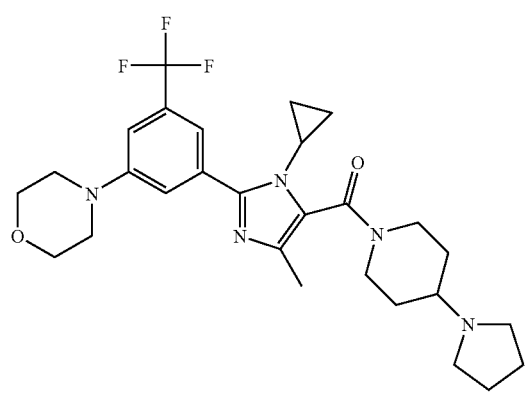

In analogy to the procedure described for example 2, the title compound has been obtained by coupling of 3-cyclopropyl-5-methyl-2-(3-morpholin-4-yl-5-trifluoromethyl-phenyl)-3H-imidazole-4-carboxylic acid (intermediate 15) with 4-pyrrolidin-1-yl-piperidine to give the title compound as yellow amorphous solid. MS: 532.2 (MH+).

Example 103

[3-Cyclopropyl-5-furan-2-yl-2-(4-trifluoromethoxy-phenyl)-3H-imidazol-4-yl]-(4-pyrrolidin-1-yl-piperidin-1-yl)-methanone

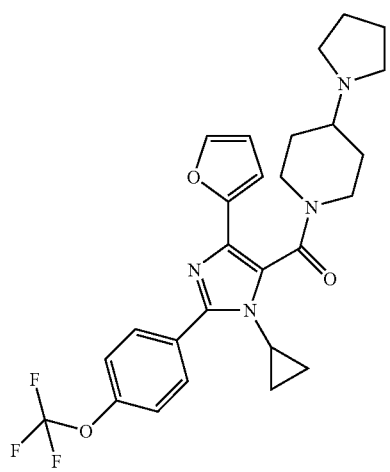

In analogy to the procedure described for example 2, the title compound has been obtained by coupling of 3-cyclopropyl-5-furan-2-yl-2-(4-trifluoromethoxy-phenyl)-3H-imidazole-4-carboxylic acid (intermediate 16) with 4-pyrrolidin-1-yl-piperidine to give the title compound light brown oil. MS: 515.3 (MH+).

Example 104

[5-Iodo-3-methyl-2-(4-trifluoromethyl-phenyl)-3H-imidazol-4-yl]-(4-pyrrolidin-1-yl-piperidin-1-yl)-methanone

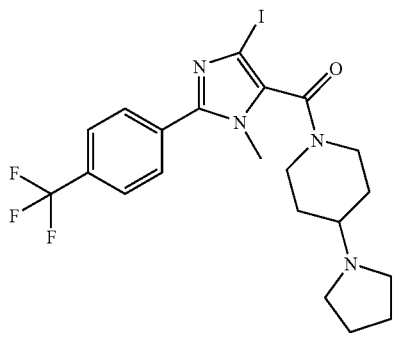

In analogy to the procedures described for intermediates 1B, 1D-F and to the procedure described for example 2, the title compound has been obtained by i) transformation of 4-trifluoromethyl-benzaldehyde into 2-(4-trifluoromethyl-phenyl)-1H-imidazole; ii) iodination of 2-(4-trifluoromethyl-phenyl)-1H-imidazole to give 4,5-diiodo-2-(4-trifluoromethyl-phenyl)-1H-imidazole; iii) methylation of 4,5-diiodo-2-(4-trifluoromethyl-phenyl)-1H-imidazole to give 4,5-diiodo-1-methyl-2-(4-trifluoromethyl-phenyl)-1H-imidazole; iv) carboxylation of 4,5-diiodo-1-methyl-2-(4-trifluoromethyl-phenyl)-1H-imidazole to give 5-iodo-3-methyl-2-(4-trifluoromethyl-phenyl)-3H-imidazole-4-carboxylic acid; v) coupling of 5-iodo-3-methyl-2-(4-trifluoromethyl-phenyl)-3H-imidazole-4-carboxylic acid with 4-pyrrolidin-1-yl-piperidine to give the title compound as yellow amorphous solid. MS: 533.2 (MH+).

Example 105

[2-(3,4-Dichloro-phenyl)-5-iodo-3-methyl-3H-imidazol-4-yl]-(4-pyrrolidin-1-yl-piperidin-1-yl)-methanone

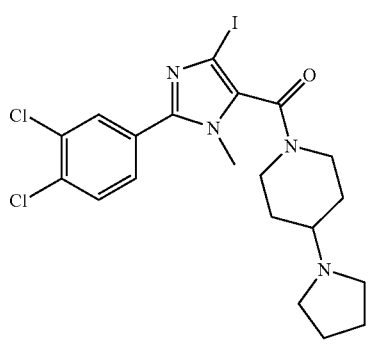

In analogy to the procedures described for intermediates 1B, 1D-F and to the procedure described for example 2, the title compound has been obtained by i) transformation of 3,4-dichloro-benzaldehyde into 2-(3,4-dichloro-phenyl)-1H-imidazole; ii) iodination of 2-(3,4-dichloro-phenyl)-1H-imidazole to give 2-(3,4-dichloro-phenyl)-4,5-diiodo-1H-imidazole; iii) methylation of 2-(3,4-dichloro-phenyl)-4,5-diiodo-1H-imidazole to give 2-(3,4-dichloro-phenyl)-4,5-diiodo-1-methyl-1H-imidazole; iv) carboxylation of 2-(3,4-dichloro-phenyl)-4,5-diiodo-1-methyl-1H-imidazole to give 2-(3,4-dichloro-phenyl)-5-iodo-3-methyl-3H-imidazole-4-carboxylic acid; v) coupling of 2-(3,4-dichloro-phenyl)-5-iodo-3-methyl-3H-imidazole-4-carboxylic acid with 4-pyrrolidin-1-yl-piperidine to give the title compound as light brown amorphous solid. MS: 533.1 (MH+, 2Cl).

Example 106

[5-Methoxy-3-methyl-2-(3-trifluoromethoxy-phenyl)-3H-imidazol-4-yl]-(4-pyrrolidin-1-yl-piperidin-1-yl)-methanone

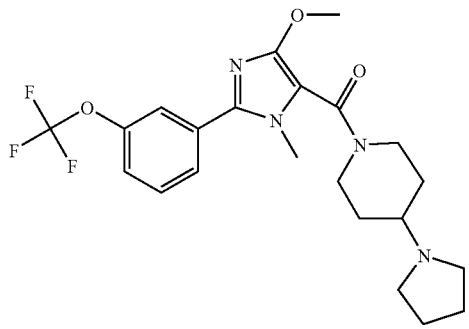

In analogy to the procedure described for example 2, the title compound has been obtained by coupling of 5-methoxy-3-methyl-2-(3-trifluoromethoxy-phenyl)-3H-imidazole-4-carboxylic acid (intermediate 17) with 4-pyrrolidin-1-yl-piperidine to give the title compound as light brown oil. MS: 453.3 (MH+).

Example 107

[3-Methyl-5-pyrimidin-5-yl-2-(4-trifluoromethyl-phenyl)-3H-imidazol-4-yl]-(4-pyrrolidin-1-yl-piperidin-1-yl)-methanone

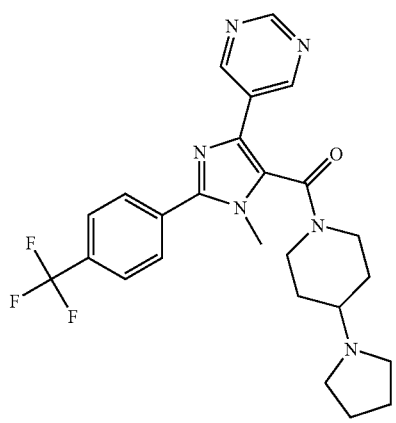

In analogy to the procedure described for example 7, [5-iodo-3-methyl-2-(4-trifluoromethyl-phenyl)-3H-imidazol-4-yl]-(4-pyrrolidin-1-yl-piperidin-1-yl)-methanone (example 104) was reacted with pyrimidine-5-yl-boronic acid to give the title compound as colorless amorphous solid. MS: 485.3 (MH+).

Example 108

[2-(3,4-Dichloro-phenyl)-3-methyl-5-pyrimidin-5-yl-3H-imidazol-4-yl]-(4-pyrrolidin-1-yl-piperidin-1-yl)-methanone

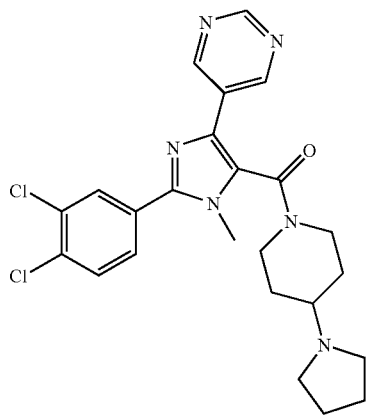

In analogy to the procedure described for example 7, [2-(3,4-dichloro-phenyl)-5-iodo-3-methyl-3H-imidazol-4-yl]-(4-pyrrolidin-1-yl-piperidin-1-yl)-methanone (example 105) was reacted with pyrimidine-5-yl-boronic acid to give the title compound as colorless amorphous solid. MS: 485.3 (MH+, 2Cl).

Example 109

[3-Methyl-5-pyridin-3-yl-2-(4-trifluoromethyl-phenyl)-3H-imidazol-4-yl]-(4-pyrrolidin-1-yl-piperidin-1-yl)-methanone

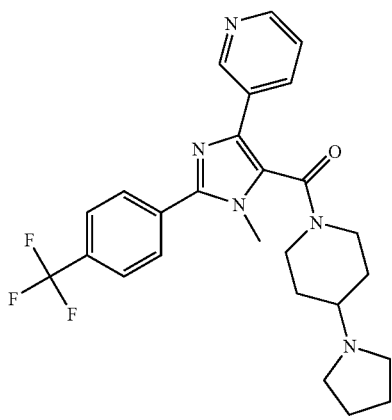

In analogy to the procedure described for example 7, [5-iodo-3-methyl-2-(4-trifluoromethyl-phenyl)-3H-imidazol-4-yl]-(4-pyrrolidin-1-yl-piperidin-1-yl)-methanone (example 104) was reacted with pyridine-3-yl-boronic acid to give the title compound as light yellow amorphous solid. MS: 484.3 (MH+).

Example 110

[2-(3,4-Dichloro-phenyl)-3-methyl-5-pyridin-3-yl-3H-imidazol-4-yl]-(4-pyrrolidin-1-yl-piperidin-1-yl)-methanone

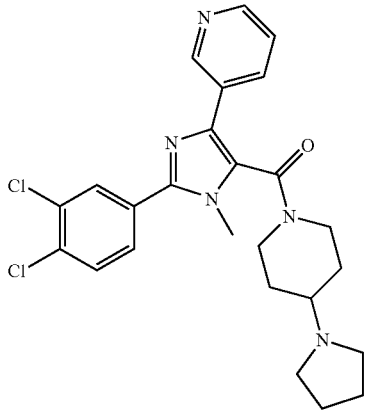

In analogy to the procedure described for example 7, [2-(3,4-dichloro-phenyl)-5-iodo-3-methyl-3H-imidazol-4-yl]-(4-pyrrolidin-1-yl-piperidin-1-yl)-methanone (example 105) was reacted with pyridine-3-yl-boronic acid to give the title compound as colorless amorphous solid. MS: 484.3 (MH+, 2Cl).

Example 111

[5-(2-Amino-pyrimidin-5-yl)-3-methyl-2-(4-trifluoromethyl-phenyl)-3H-imidazol-4-yl]-(4-pyrrolidin-1-yl-piperidin-1-yl)-methanone

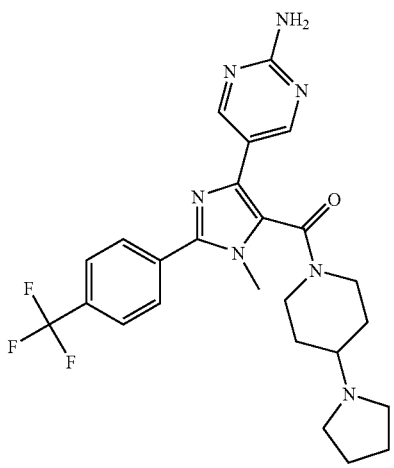

In analogy to the procedure described for example 7, [5-iodo-3-methyl-2-(4-trifluoromethyl-phenyl)-3H-imidazol-4-yl]-(4-pyrrolidin-1-yl-piperidin-1-yl)-methanone (example 104) was reacted with 2-amino-pyrimidin-5-yl-boronic acid to give the title compound as colorless solid. MS: 499.7 (MH+).

Example 112

[5-(6-Amino-pyridin-3-yl)-3-methyl-2-(4-trifluoromethyl-phenyl)-3H-imidazol-4-yl]-(4-pyrrolidin-1-yl-piperidin-1-yl)-methanone

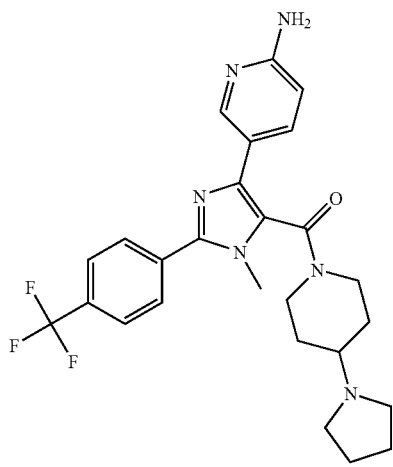

In analogy to the procedure described for example 7, [5-iodo-3-methyl-2-(4-trifluoromethyl-phenyl)-3H-imidazol-4-yl]-(4-pyrrolidin-1-yl-piperidin-1-yl)-methanone (example 104) was reacted with 6-amino-pyridin-3-yl-boronic acid to give the title compound as off-white solid. MS: 499.2 (MH+).

Example 113

[5-(6-Hydroxy-pyridin-3-yl)-3-methyl-2-(4-trifluoromethyl-phenyl)-3H-imidazol-4-yl]-(4-pyrrolidin-1-yl-piperidin-1-yl)-methanone

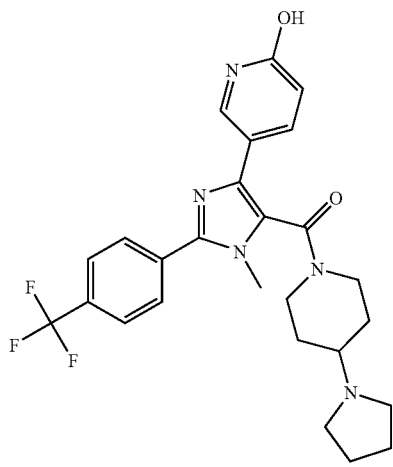

In analogy to the procedure described for example 7, [5-iodo-3-methyl-2-(4-trifluoromethyl-phenyl)-3H-imidazol-4-yl]-(4-pyrrolidin-1-yl-piperidin-1-yl)-methanone (example 104) was reacted with 6-hydroxy-pyridin-3-yl-boronic acid pinacol ester to give the title compound as off-white solid. MS: 500.2 (MH+).

Example 114

[5-(2-Methoxy-pyrimidin-5-yl)-3-methyl-2-(4-trifluoromethyl-phenyl)-3H-imidazol-4-yl]-(4-pyrrolidin-1-yl-piperidin-1-yl)-methanone

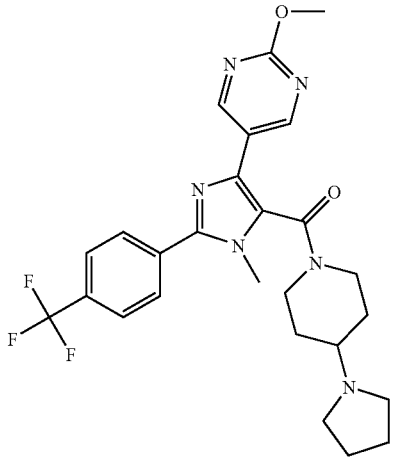

In analogy to the procedure described for example 7, [5-iodo-3-methyl-2-(4-trifluoromethyl-phenyl)-3H-imidazol-4-yl]-(4-pyrrolidin-1-yl-piperidin-1-yl)-methanone (example 104) was reacted with 2-methoxy-pyrimidin-5-yl-boronic acid to give the title compound as light yellow solid. MS: 515.3 (MH+).

Example 115

[5-(2-Hydroxy-pyrimidin-5-yl)-3-methyl-2-(4-trifluoromethyl-phenyl)-3H-imidazol-4-yl]-(4-pyrrolidin-1-yl-piperidin-1-yl)-methanone

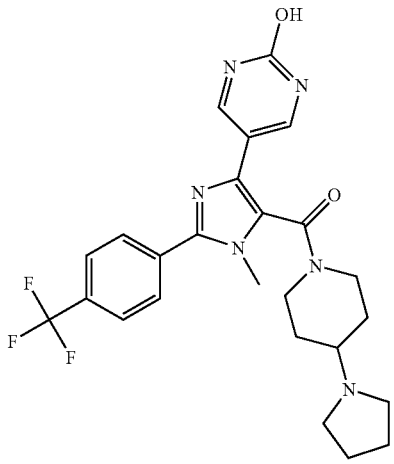

A solution of 0.25 g (0.49 mmol) of [5-(2-methoxy-pyrimidin-5-yl)-3-methyl-2-(4-trifluoromethyl-phenyl)-3H-imidazol-4-yl]-(4-pyrrolidin-1-yl-piperidin-1-yl)-methanone (example 114) in 10 ml of MeCl$_2$ was cooled down to 0° C.; then, 0.97 ml (1.0 mMol) of a boron tribromide solution (1.0 molar in MeCl$_2$) were added and the reaction mixture was warmed up to RT. After 3 hours, it was poured into crashed ice, neutralized with an aqueous sodium hydrogen carbonate solution, then extracted twice with MeCl$_2$; the organic phases were washed with water, dried over magnesium sulfate, filtered and evaporated to give 0.089 g (37%) of the title compound as yellow solid. MS: 501.2 (MH$^+$).

Example 116

[5-Iodo-3-methyl-2-(6-trifluoromethyl-pyridin-3-yl)-3H-imidazol-4-yl]-(4-pyrrolidin-1-yl-piperidin-1-yl)-methanone

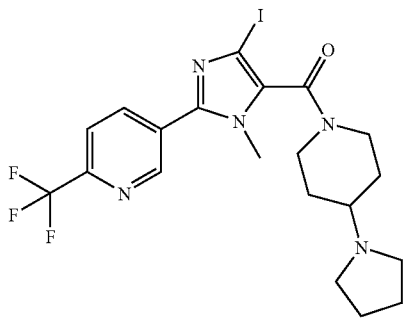

In analogy to the procedures described for intermediates 1B, 1D-F and to the procedure described for example 2, the title compound has been obtained by i) transformation of 6-trifluoromethyl-pyridine-3-carbaldehyde into 5-(1H-imidazol-2-yl)-2-trifluoromethyl-pyridine; ii) iodination of 5-(1H-imidazol-2-yl)-2-trifluoromethyl-pyridine to give 5-(4,5-diiodo-1H-imidazol-2-yl)-2-trifluoromethyl-pyridine; iii) methylation of 5-(4,5-diiodo-1H-imidazol-2-yl)-2-trifluoromethyl-pyridine to give 5-(4,5-diiodo-1-methyl-1H-imidazol-2-yl)-2-trifluoromethyl-pyridine; iv) carboxylation of 5-(4,5-diiodo-1-methyl-1H-imidazol-2-yl)-2-trifluoromethyl-pyridine to give 5-iodo-3-methyl-2-(6-trifluoromethyl-pyridin-3-yl)-3H-imidazole-4-carboxylic acid; v) coupling of 5-iodo-3-methyl-2-(6-trifluoromethyl-pyridin-3-yl)-3H-imidazole-4-carboxylic acid with 4-pyrrolidin-1-yl-piperidine to give the title compound as off-white amorphous solid. MS: 534.1 (MH$^+$).

Example 117

[3-Methyl-5-pyridin-3-yl-2-(6-trifluoromethyl-pyridin-3-yl)-3H-imidazol-4-yl]-(4-pyrrolidin-1-yl-piperidin-1-yl)-methanone

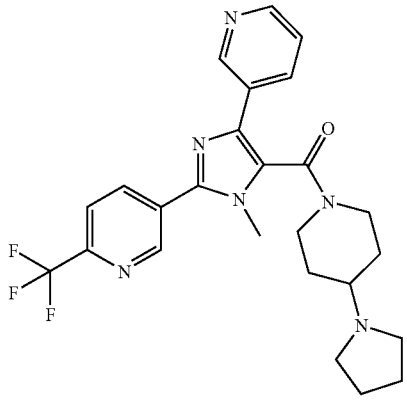

In analogy to the procedure described for example 7, [5-iodo-3-methyl-2-(6-trifluoromethyl-pyridin-3-yl)-3H-imidazol-4-yl]-(4-pyrrolidin-1-yl-piperidin-1-yl)-methanone (example 116) was reacted with pyridine-3-yl-boronic acid to give the title compound as colorless amorphous solid. MS: 485.4 (MH$^+$).

Example 118

[3-Methyl-5-pyrimidin-5-yl-2-(6-trifluoromethyl-pyridin-3-yl)-3H-imidazol-4-yl]-(4-pyrrolidin-1-yl-piperidin-1-yl)-methanone

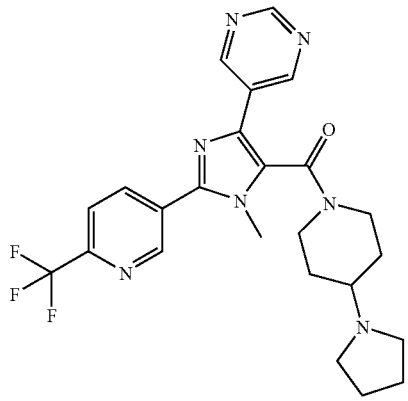

In analogy to the procedure described for example 7, [5-iodo-3-methyl-2-(6-trifluoromethyl-pyridin-3-yl)-3H-imidazol-4-yl]-(4-pyrrolidin-1-yl-piperidin-1-yl)-methanone (example 116) was reacted with pyrimidine-5-yl-boronic acid to give the title compound as colorless amorphous solid. MS: 486.3 (MH$^+$).

Example 119

[3-Cyclopropyl-5-pyrimidin-5-yl-2-(4-trifluoromethoxy-phenyl)-3H-imidazol-4-yl]-[4-((S)-2-hydroxymethyl-pyrrolidin-1-yl)-piperidin-1-yl]-methanone

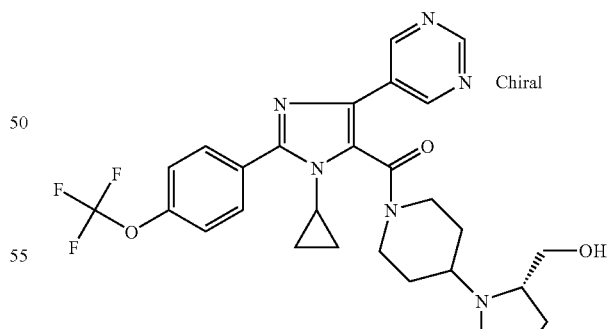

In analogy to the procedures described for example 90, intermediate 9C and to the procedure described for example 2, the title compound has been obtained by i) treatment of 3-cyclopropyl-5-(2-methylsulfanyl-pyrimidin-5-yl)-2-(4-trifluoromethoxy-phenyl)-3H-imidazole-4-carboxylic acid ethyl ester (intermediate 10B) with Raney nickel in ethanol to give 3-cyclopropyl-5-pyrimidin-5-yl-2-(4-trifluoromethoxyphenyl)-3H-imidazole-4-carboxylic acid ethyl ester; ii) saponification of 3-cyclopropyl-5-pyrimidin-5-yl-2-(4-trifluoromethoxy-phenyl)-3H-imidazole-4-carboxylic acid ethyl ester to give 3-cyclopropyl-5-pyrimidin-5-yl-2-(4-trifluoromethoxy-phenyl)-3H-imidazole-4-carboxylic acid; iii) coupling of 3-cyclopropyl-5-pyrimidin-5-yl-2-(4-trifluoromethoxy-phenyl)-3H-imidazole-4-carboxylic acid with ((S)-1-piperidin-4-yl-pyrrolidin-2-yl)-methanol di-hydrochloride [prepared as described for ((R)-1-piperidin-4-yl-pyrrolidin-2-yl)-methanol di-hydrochloride (intermediate 2), but starting from (S)-(−)-pyrrolidin-2-yl-methanol] to give the title compound as a light yellow solid. MS: 557.2 (MH$^+$).

Example A

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcristalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
| --- | --- |
| Compound of formula (I) | 3.0 mg |
| Polyethylene Glycol 400 | 150.0 mg |
| Acetic Acid | q.s. ad pH 5.0 |
| Water for injection solutions | Ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
| --- | --- |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
| --- | --- |
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavouring additives and filled into sachets.

What is claimed:

1. A compound of the formula (I)

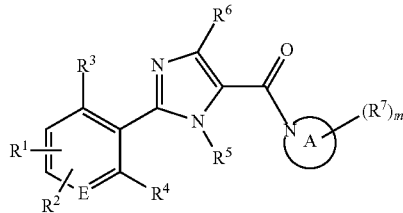

wherein

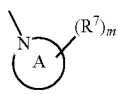

is 4-pyrrolidin-1-yl-piperidin-1-yl or 4-(2-hydroxymethyl-pyrrolidin-1-yl)-piperidin-1-yl;

E is N or CH, provided that $R^1$ or $R^2$ can attach to C, by replacing H;

$R^1$ and $R^2$ are independently hydrogen, halogen, $C_{1-6}$ alkoxy, $C_{1-6}$ alkyl, halo $C_{1-6}$ alkyl, halo $C_{1-6}$ alkoxy or optionally substituted heterocyclyl;

provided that one of $R^1$ and $R^2$ is not hydrogen;

$R^3$ and $R^4$ are independently hydrogen, $C_{1-6}$ alkoxy, halo $C_{1-6}$ alkyl, halo $C_{1-6}$ alkoxy or halogen;

$R^5$ is $C_{1-6}$ alkyl, halo $C_{1-6}$ alkyl, $C_{3-7}$ cycloalkyl or $C_{3-7}$ cycloalkyl $C_{1-6}$ alkyl;

$R^6$ is hydrogen, $C_{1-6}$ alkyl, halo $C_{1-6}$ alkyl, trimethylsilanyl $C_{1-6}$ alkyl, heteroalkyl, $C_{2-6}$ alkenyl, $C_{2-6}$ alkynyl, hydroxy $C_{2-6}$ alkenyl, hydroxy $C_{2-6}$ alkynyl, $C_{1-6}$ alkoxy $C_{2-6}$ alkenyl, $C_{1-6}$ alkoxy $C_{2-6}$ alkynyl, trimethylsilanyl $C_{2-6}$ alkenyl, trimethylsilanyl $C_{2-6}$ alkynyl, $C_{1-6}$ alkoxy, halo $C_{1-6}$ alkoxy, heteroalkoxy, optionally substituted $C_{3-7}$ cycloalkyl, optionally substituted $C_{3-7}$ cycloalkyl $C_{1-6}$ alkyl, halogen, cyano, optionally substituted phenyl, optionally substituted heteroaryl, optionally substituted heterocyclyl or optionally substituted phenyl-methoxy-$C_{1-6}$ alkyl;

or pharmaceutically acceptable salt thereof.

2. The compound of claim 1, wherein E is CH, provided that $R^1$ or $R^2$ can attach to C, by replacing H, and $R^1$ and $R^2$ are independently hydrogen, halogen, $C_{1-6}$ alkoxy, $C_{1-6}$ alkyl, halo $C_{1-6}$ alkyl or halo $C_{1-6}$ alkoxy.

3. The compound of claim 1, wherein one of $R^1$ and $R^2$ is hydrogen, $C_{1-6}$ alkyl, halo $C_{1-6}$ alkyl or halo $C_{1-6}$ alkoxy and the other is $C_{1-6}$ alkyl, halo $C_{1-6}$ alkyl or halo $C_{1-6}$ alkoxy.

4. The compound of claim 3, wherein one of $R^1$ and $R^2$ is hydrogen and the other is n-hexyl, trifluoromethyl or trifluoromethoxy.

5. The compound of claim 4, wherein $R^3$ and $R^4$ are independently hydrogen or $C_{1-6}$ alkoxy.

6. The compound of claim 5, wherein $R^3$ and $R^4$ are hydrogen.

7. The compound of claim 6, wherein $R^5$ is $C_{1-6}$ alkyl or $C_{3-7}$ cycloalkyl.

8. The compound of claim 7, wherein $R^5$ is methyl.

9. The compound of claim 8, wherein $R^6$ is hydrogen, $C_{1-6}$ alkyl, trimethylsilanyl $C_{1-6}$ alkyl, heteroalkyl, $C_{2-6}$ alkenyl, $C_{2-6}$ alkynyl, hydroxy $C_{2-6}$ alkenyl, hydroxy $C_{2-6}$ alkynyl, $C_{1-6}$ alkoxy $C_{2-6}$ alkenyl, $C_{1-6}$ alkoxy $C_{2-6}$ alkynyl, trimethylsilanyl $C_{2-6}$ alkenyl, trimethylsilanyl $C_{2-6}$ alkynyl, optionally substituted $C_{3-7}$ cycloalkyl, optionally substituted $C_{3-7}$ cycloalkyl-$C_{1-6}$ alkyl, halogen, cyano, optionally substituted phenyl, optionally substituted heteroaryl, optionally substituted heterocyclyl or optionally substituted phenyl-methoxy-$C_{1-6}$ alkyl.

10. The compound of claim 9, wherein $R^6$ is hydrogen, $C_{1-6}$ alkyl, heteroalkyl, $C_{2-6}$ alkynyl, hydroxy $C_{2-6}$ alkynyl, $C_{1-6}$ alkoxy $C_{2-6}$ alkynyl, trimethylsilanyl $C_{2-6}$ alkynyl, optionally substituted $C_{3-7}$ cycloalkyl, halogen, cyano, optionally substituted phenyl, optionally substituted heteroaryl or optionally substituted phenyl-$C_{1-6}$ methoxy-$C_{1-6}$ alkyl.

11. The compound of claim 10, wherein $R^6$ is $C_{2-6}$ alkynyl, halogen, cyano or optionally substituted heteroaryl.

12. The compound of claim 11, wherein $R^6$ is pyridinyl, pyrimidinyl, iodo, ethynyl or cyano.

13. A compound of claim 1 selected from the group consisting of

[2-(3-Hexyl-phenyl)-3-methyl-5-pyrimidin-5-yl-3H-imidazol-4-yl]-(4-pyrrolidin-1-yl-piperidin-1-yl)-methanone,

[5-Iodo-3-methyl-2-(3-trifluoromethoxy-phenyl)-3H-imidazol-4-yl]-(4-pyrrolidin-1-yl-piperidin-1-yl)-methanone,

[3-Methyl-5-pyrimidin-5-yl-2-(3-trifluoromethoxy-phenyl)-3H-imidazol-4-yl]-(4-pyrrolidin-1-yl-piperidin-1-yl)-methanone,

[3-Methyl-5-pyrimidin-5-yl-2-(3-trifluoromethyl-phenyl)-3H-imidazol-4-yl]-(4-pyrrolidin-1-yl-piperidin-1-yl)-methanone,

[5-Ethynyl-3-methyl-2-(3-trifluoromethyl-phenyl)-3H-imidazol-4-yl]-(4-pyrrolidin-1-yl-piperidin-1-yl)-methanone, 1-Methyl-5-(4-pyrrolidin-1-yl-piperidine-1-carbonyl)-2-(3-trifluoromethoxy-phenyl)-1H-imidazole-4-carbonitrile,

[3-Methyl-5-pyridin-4-yl-2-(3-trifluoromethoxy-phenyl)-3H-imidazol-4-yl]-(4-pyrrolidin-1-yl-piperidin-1-yl)-methanone,

[2-(3-Hexyl-phenyl)-5-iodo-3-methyl-3H-imidazol-4-yl]-[4-(2-hydroxymethyl-pyrrolidin-1-yl)-piperidin-1-yl]-methanone,

[4-(2-Hydroxymethyl-pyrrolidin-1-yl)-piperidin-1-yl]-[5-iodo-3-methyl-2-(3-trifluoromethoxy-phenyl)-3H-imidazol-4-yl]-methanone,

[4-(2-Hydroxymethyl-pyrrolidin-1-yl)-piperidin-1-yl]-[3-methyl-5-pyrimidin-5-yl-2-(3-trifluoromethoxy-phenyl)-3H-imidazol-4-yl]-methanone,

[4-(2-Hydroxymethyl-pyrrolidin-1-yl)-piperidin-1-yl]-[3-methyl-5-pyridin-4-yl-2-(3-trifluoromethoxy-phenyl)-3H-imidazol-4-yl]-methanone,

[3-Cyclopropyl-5-pyrimidin-5-yl-2-(3-trifluoromethyl-phenyl)-3H-imidazol-4-yl]-(4-pyrrolidin-1-yl-piperidin-1-yl)-methanone,

[3-Methyl-5-pyrimidin-5-yl-2-(4-trifluoromethoxy-phenyl)-3H-imidazol-4-yl]-(4-pyrrolidin-1-yl-piperidin-1-yl)-methanone,

[3-Cyclopropyl-5-pyridin-3-yl-2-(4-trifluoromethoxy-phenyl)-3H-imidazol-4-yl]-(4-pyrrolidin-1-yl-piperidin-1-yl)-methanone,

[3-Cyclopropyl-5-pyridin-3-yl-2-(4-trifluoromethoxy-phenyl)-3H-imidazol-4-yl]-[4-((S)-2-hydroxymethyl-pyrrolidin-1-yl)-piperidin-1-yl]-methanone,

[3-Cyclopropyl-5-pyrimidin-5-yl-2-(4-trifluoromethoxy-phenyl)-3H-imidazol-4-yl]-(4-pyrrolidin-1-yl-piperidin-1-yl)-methanone,

[5-(2-Amino-pyrimidin-5-yl)-3-cyclopropyl-2-(4-trifluoromethoxy-phenyl)-3H-imidazol-4-yl]-(4-pyrrolidin-1-yl-piperidin-1-yl)-methanone,

[5-(6-Amino-pyridin-3-yl)-3-cyclopropyl-2-(4-trifluoromethoxy-phenyl)-3H-imidazol-4-yl]-(4-pyrrolidin-1-yl-piperidin-1-yl)-methanone,

[3-Cyclopropyl-5-(1H-[1,2,4]triazol-3-yl)-2-(4-trifluoromethoxy-phenyl)-3H-imidazol-4-yl]-(4-pyrrolidin-1-yl-piperidin-1-yl)-methanone,

[3-Cyclopropyl-5-(1H-pyrazol-4-yl)-2-(4-trifluoromethoxy-phenyl)-3H-imidazol-4-yl]-(4-pyrrolidin-1-yl-piperidin-1-yl)-methanone,

[3-Cyclopropyl-5-(1H-[1,2,3]triazol-4-yl)-2-(4-trifluoromethoxy-phenyl)-3H-imidazol-4-yl]-(4-pyrrolidin-1-yl-piperidin-1-yl)-methanone,

[3-Cyclopropyl-5-(2-hydroxy-pyridin-4-yl)-2-(4-trifluoromethoxy-phenyl)-3H-imidazol-4-yl]-(4-pyrrolidin-1-yl-piperidin-1-yl)-methanone and

[3-Cyclopropyl-5-pyrimidin-5-yl-2-(4-trifluoromethoxy-phenyl)-3H-imidazol-4-yl]-[4-((S)-2-hydroxymethyl-pyrrolidin-1-yl)-piperidin-1-yl]-methanone.

14. A pharmaceutical composition comprising a compound of claim 1 and a pharmaceutically acceptable excipient.

* * * * *